US009410123B2

(12) United States Patent
Lanza et al.

(10) Patent No.: US 9,410,123 B2
(45) Date of Patent: *Aug. 9, 2016

(54) HEMANGIO COLONY FORMING CELLS AND NON-ENGRAFTING HEMANGIO CELLS

(75) Inventors: Robert Lanza, Clinton, MA (US); Shi-Jiang Lu, Shrewsbury, MA (US)

(73) Assignee: Ocata Therapeutics, Inc., Marlborough, MA (US)

( * ) Notice: Subject to any disclaimer, the term of this patent is extended or adjusted under 35 U.S.C. 154(b) by 130 days.

This patent is subject to a terminal disclaimer.

(21) Appl. No.: 12/991,096

(22) PCT Filed: May 6, 2009

(86) PCT No.: PCT/US2009/043043
§ 371 (c)(1),
(2), (4) Date: Nov. 4, 2010

(87) PCT Pub. No.: WO2009/137624
PCT Pub. Date: Nov. 12, 2009

(65) Prior Publication Data
US 2011/0064705 A1 Mar. 17, 2011

Related U.S. Application Data

(60) Provisional application No. 61/126,802, filed on May 6, 2008, provisional application No. 61/190,282, filed on Aug. 26, 2008.

(51) Int. Cl.
C12N 5/00 (2006.01)
C12N 5/0789 (2010.01)

(52) U.S. Cl.
CPC .......... C12N 5/0647 (2013.01); C12N 2500/90 (2013.01); C12N 2501/115 (2013.01); C12N 2501/125 (2013.01); C12N 2501/145 (2013.01); C12N 2501/155 (2013.01); C12N 2501/165 (2013.01); C12N 2501/26 (2013.01); C12N 2506/02 (2013.01); C12N 2506/45 (2013.01)

(58) Field of Classification Search
None
See application file for complete search history.

(56) References Cited

U.S. PATENT DOCUMENTS

| 5,128,259 | A | 7/1992 | Morgan et al. |
| 5,599,705 | A | 2/1997 | Cameron |
| 5,914,268 | A | 6/1999 | Keller et al. |
| 6,602,711 | B1 | 8/2003 | Thomson et al. |
| 7,220,584 | B2 | 5/2007 | Thomson et al. |
| 7,374,934 | B2 | 5/2008 | Keller et al. |
| 8,017,393 | B2 * | 9/2011 | Lanza et al. ............... 435/377 |
| 2002/0035735 | A1 | 3/2002 | Schatten et al. |
| 2003/0175954 | A1 | 9/2003 | Shamblott et al. |
| 2004/0052771 | A1 | 3/2004 | Lim |
| 2004/0229350 | A1 | 11/2004 | Strelchenko et al. |
| 2005/0153443 | A1 | 7/2005 | Lanza et al. |
| 2005/0221482 | A1 | 10/2005 | Burt |
| 2005/0221487 | A1 | 10/2005 | Zon et al. |
| 2007/0141703 | A1 | 6/2007 | Stanley et al. |
| 2007/0218552 | A1 | 9/2007 | Giarratana et al. |
| 2007/0298496 | A1 | 12/2007 | Kuo et al. |
| 2008/0003674 | A1 | 1/2008 | Slukvin et al. |
| 2008/0014180 | A1 | 1/2008 | Lanza et al. |
| 2008/0057041 | A1 | 3/2008 | Chung et al. |
| 2008/0108044 | A1 | 5/2008 | Rajesh et al. |
| 2009/0304646 | A1 | 12/2009 | Sakurada et al. |
| 2011/0086424 | A1 | 4/2011 | Lanza et al. |
| 2012/0027731 | A1 | 2/2012 | Lanza et al. |

FOREIGN PATENT DOCUMENTS

| CN | 102660495 | 9/2002 |
| CN | 101045914 | 10/2007 |
| CN | 101528915 | 9/2009 |
| CN | 102083960 | 6/2011 |
| CN | 102083963 | 6/2011 |
| CN | ZL 200980125862 | 12/2014 |
| EP | 2013331 | 1/2009 |

(Continued)

OTHER PUBLICATIONS

Springer et al. VEGF Gene Delivery to Muscle: Potential Role for Vasculogenesis in Adults. Molecular Cell (1998) 2: 549-558.*
Kennedy et al. (Development of the hemangioblast defines the onset of hematopoiesis in human ES cell differentiation cultures. Blood (2007) 109:2679-2687).*
Kennedy et al. (Development of the hemangioblast defines the onset of hematopoiesis in human ES cell differentiation cultures. Blood. Prepublished online Blood First Edition Paper, Dec. 5, 2006).*
Life Technologies (Guidelines for Maintaining Cultured Cells, copyright 2014).*
International Preliminary Report on Patentability for PCT/US2009/043043.

(Continued)

Primary Examiner — Karen Cochrane Carlson
Assistant Examiner — Natalie Moss
(74) Attorney, Agent, or Firm — Nixon Peabody LLP; Stephen W. Chen

(57) ABSTRACT

Methods of generating and expanding human hemangio-colony forming cells and non-engrafting hemangio cells in vitro and methods of expanding and using such cells are disclosed. The methods permit the production of large numbers of hemangio-colony forming cells, non-engrafting hemangio cells as well as derivative cells, such as hematopoietic and endothelial cells. The cells obtained by the methods disclosed may be used for a variety of research, clinical, and therapeutic applications. Human non-engrafting hemangio cells are a novel progenitor cell population that is related to but distinct from the hemangioblast and human hemangio-colony forming cells. The invention also provides compositions, preparations, and solutions comprising hemangio-colony forming cells, non-engrafting hemangio cells or cells differentiated therefrom. The compositions, preparations, and solutions include cryopreserved preparations and substantially purified preparations, as well as mixed compositions formulated in combination with related hemangioblast progenitor cell types that can engraft into the bone marrow.

14 Claims, 12 Drawing Sheets

(56) References Cited

FOREIGN PATENT DOCUMENTS

| EP | 2288690 | 3/2011 |
|---|---|---|
| EP | 2291513 | 3/2011 |
| EP | 2377923 | 10/2011 |
| EP | 2377924 | 10/2011 |
| EP | 2377925 | 10/2011 |
| EP | 2426197 | 3/2012 |
| EP | 2712921 A1 | 4/2014 |
| HK | 1127087 A | 9/2009 |
| HK | 1151064 A | 1/2012 |
| HK | 1153774 A | 4/2012 |
| JP | 2004-504834 | 2/2004 |
| JP | 2004-531262 | 10/2004 |
| JP | 2005-511084 | 4/2005 |
| JP | 2009-533059 | 9/2009 |
| JP | 2011-519576 | 7/2011 |
| JP | 2011-519577 | 7/2011 |
| JP | 2013126423 | 6/2013 |
| NZ | 518191 | 1/2004 |
| NZ | 572841 | 1/2012 |
| WO | WO 9517500 | 6/1995 |
| WO | WO 9967360 | 12/1999 |
| WO | WO 03050251 | 6/2003 |
| WO | WO 2004029231 | 4/2004 |
| WO | 2005078073 A2 | 8/2005 |
| WO | WO 2005118780 | 12/2005 |
| WO | WO 2006050330 | 5/2006 |
| WO | WO 2006130651 | 12/2006 |
| WO | WO 2007095064 | 8/2007 |
| WO | WO 2007120811 | 10/2007 |
| WO | WO 2008151386 | 12/2008 |
| WO | WO 2009104825 | 8/2009 |
| WO | WO 2009137629 | 11/2009 |

OTHER PUBLICATIONS

International Preliminary Report on Patentability for PCT/US2009/043050.
PCT/US2007/009106 with Int'l Search Report.
PCT/US2007/009106 IPRP.
Australian Examination Report dated Mar. 6, 2012 for 2007238660.
Chinese Examination Report dated Jul. 30, 2010 for 200780021822.6.
Chinese Examination Report dated Dec. 16, 2011 for 200780021822.6.
Chinese Rejection Decision dated Jul. 30, 2012 for 200780021822.6.
EP Examination Report dated Mar. 2, 2009 for 07755391.5.
EP Examination Report dated Jul. 5, 2010 for 07755391.5.
EP Examination Report dated Apr. 1, 2011 for 07755391.5.
EP Official Notification Telephone Conference dated Sep. 26, 2011 for 07755391.5.
EP Search Report dated Sep. 19, 2011 for 11155399.6.
EP Search Report dated Feb. 6, 2012 for 11155482.0.
EP Search Report dated Sep. 19, 2011 for 11155495.2.
EP Search Report dated Sep. 19, 2011 for 11155500.9.
Japanese Office Action dated Sep. 28, 2012 for 2009-505494.
New Zealand Examination Report dated May 31, 2010 for 572842.
New Zealand Examination Report dated Jun. 24, 2011 for 572842.
New Zealand Examination Report dated Oct. 17, 2011 for 572842.
New Zealand Examination Report dated Nov. 3, 2011 for 572842.
New Zealand Notice of Allowance dated Jan. 12, 2012 for 572842.
New Zealand Examination Report dated Dec. 7, 2011 for 596761.
US Restriction Requirement dated May 4, 2010 for U.S. Appl. No. 11/787,262.
US Non-Final Office Action dated Oct. 2, 2009 for U.S. Appl. No. 11/787,262.
US Non-Final Office Action dated Sep. 2, 2010 for U.S. Appl. No. 11/787,262.
US Notice of Allowance for U.S. Appl. No. 11/787,262 dated Apr. 27, 2011.
Chinese Office Action dated Jan. 17, 2012 for 200980125860.5.
European Search Report dated Jan. 26, 2012 for 09743610.9.
Mexican Office Action dated Mar. 1, 2012 for MX/a/2010/012088.
Mexican Office Action dated Jul. 19, 2012 for MX/a/2010/012088.
PCT/US2009/043050 Int'l Search Report.
Chinese Office Action dated Dec. 31, 2011 for 200980125862.4.
Chinese 2nd Office Action dated Aug. 9, 2012 for 200980125862.4.
European Search Report dated Jan. 26, 2012 for 09743615.8.
Mexican Office Action stamped Mar. 1, 2012 for MX/a/2010/012089.
Mexican Office Action stamped Nov. 8, 2012 for MX/a/2010/012089.
US Restriction Requirement dated Dec. 10, 2012 for U.S. Appl. No. 12/991,111.
Baek et al., "Stroma-free mass production of clinical-grade red blood cells (RBCs) by using poloxamer 188 as an RBC survival enhancer," Transfusion, vol. 49, Nov. 2009, pp. 2285-2295.
Bowles et al., "HOXB4 Overexpression Promotes Hematopoietic Development by Human Embryonic Stem Cells," Stem Cells, 2006, 24: 1359-1369.
Chan-Ling et al., "Hematopoietic stem cells provide repair functions after laser-induced Bruch's Membrane Rupture Model of Choroidal Neovascularization," Am. J. Pathology, vol. 168, No. 3, Mar. 2006; 1031-1044.
Choi et al., "A common precursor for hematopoietic and endothelial cells," Development (1998) vol. 125, No. 4, pp. 725-732.
Choi et al., "In vitro development of a hemangioblast from a human embryonic stem cell," SNUhES#3, Life Sciences, 85 (2009); 39-45.
Fujimoto, et al., "Production of functional platelets by differentiated embryonic stem (ES) cells in vitro," Blood, 102 (2003); 4044-4051.
Geens et al., "Human embryonic stem cell lines derived from single blastomeres of two 4-cell stage embryos," Human Reproduction, vol. 24, No. 11, (2009), pp. 2709-2717.
Giarratana et al., "Ex vivo generation of fully mature human red blood cells from hematopoietic stem cells," Nature Biotechnology, vol. 23, No. 1, Jan. 2005; 69-74.
Grant et al., "Adult hematopoietic stem cells provide functional hemangioblast activity during retinal neovascularization," Nature Medicine, vol. 8, No. 6, Jun. 2002; 607-612.
Irina Klimanskaya and Jill McMahon, "Approaches for Derivation and Maintenance of Human ES Cells: Detailed Procedures and Alternatives," Reference 6 from Specification-Klimanskaya and McMahon Book Chapter Stem Cells vol. 1.
Loges Sonja et al., "Identification of the adult human hemangioblast", Stem Cells and Development, Elsevier, NL, vol. 13, No. 3, Jun. 1, 2004, pp. 229-242.
Lu et al., "Robust generation of hemangioblastic progenitors from human embryonic stem cells," Regen. Med.(2008), 3(5), pp. 693-704.
Lu S J et al., "Generation of functional hemangioblasts from human embryonic stem cells," Nature Methods, Nature Publishing Group, GB, vol. 4, No. 6, Jun. 1, 2007, pp. 501-509.
Lu et al., "Biologic properties and enucleation of red blood cells from human embryonic stem cells," Blood, vol. 112, 2008; 1-10.
Lu et al., "Hemangioblasts from human embryonic stem cells generate multilayered blood vessels with functional smooth muscle cells," Regen. Medicine, 4(1), 2009; 37-47.
Lu, Shi-Jiang et al., "Recombinant H0xB4 fusion proteins enhance hematopoietic differentiation of human embryonic stem cells," Stem Cells and Development Aug. 2007, vol. 16, No. 4, pp. 547-559.
Ma et al., "Generation of functional erythrocytes from human embryonic stem cell-derived definitive hematopoiesis," PNAS, vol. 105, No. 35; Sep. 2, 2008; 13087-13092.
Ma et al., "Novel method for efficient production of multipotent hematopoietic progenitors from human embryonic stem cells," International Journal of Hematology, 2007, vol. 85, pp. 371-379.
Matsumoto et al., "Stepwise development of hematopoietic stem cells from embryonic stem cells," PLoS, vol. 4, Issue 3; Mar. 2009; pp. 1-10.
Bhatia, Mickie, "Hematopoiesis from Human Embryonic Stem Cells," New York Academy of Sciences, Annals, Wiley-Blackwell Publishing, Inc. US, vol. 1106, Jan. 1, 2007, pp. 219-222.
Nakamura et al., "In vitro production of transfusable red blood cells," Biotechnology and Genetic Engineering Reviews; vol. 25 (2008); 187-202.

(56) References Cited

OTHER PUBLICATIONS

Neildez-Nguyen et al., "Human erythroid cells produced ex vivo at large scale differentiate into red blood cells in vivo," Nature Biotechnology, vol. 20, May 2002; 467-472.
Olivier et al., "Large-scale production of embryonic red blood cells from human embryonic stem cells," Experimental Hematology, 34 (2006); 1635-1642.
Pearson et al., "The stepwise specification of embryonic stem cells to hematopoietic fate is driven by sequential exposure to Bmp4, activin A, bFGF and VEGF," Development, 135 (2008); 1525-1535.
Pick et al., "Differentiation of human embryonic stem cells in serum-free medium reveals distinct roles for bone morphogenetic protein 4, vascular endothelial growth factor, stem cell factor, and fibroblast growth factor 2 in hematopoiesis," Stem Cells, 2007; 25: 2206-2214.
Pilat et al., "H0XB4 enforces equivalent fates of ES-cell-derived and adult hematopoietic cells," Proceedings of the National Academy of Sciences, vol. 102, No. 34, pp. 12101-12106.
Purpura et al., "Analysis of the temporal and concentration-dependent effects of BMP-4, VEGF, and TPO on development of embryonic stem cell-derived mesoderm and blood progenitors in a defined, serum-free media," Experimental Hematology, 36 (2008); 1186-1198.
Sauvageau, Overexpression of HOXB4 in hempotopoietic cells causes the selective expansion of more primitive populations in vitro and in vivo, Genes & Development, 9:1753-1765, 1995 Cold Spring Harbor Laboratory Press.
Senger, "Pathways to Pregnancy and Parturition. Current Concepts," Inc.: Pullman, 1997. Chapter 13, pp. 221-222.
Seliger et al., "Chemical production of excited states. chemiluminescence of carcinogenic hydorcarbons accompanying their metabolic hydroxylation and a proposal for common active site geometries for hydroxylation,"The Journal of Physical Chemistry, 1976, vol. 80, No. 20, pp. 2296-2306.
Schenke-Layland et al., "Reprogrammed mouse fibroblasts differentiate into cells of the cardiovascular and hematology lineages," Stem Cells Epub, Apr. 2008, vol. 26, pp. 1537-1546.
Stem Cell: Scientific Progress and Future Research Directions. Department of Health and Human Services. Jun. 2001, pp. 1-4.
Svingen and KF Tonissen, "Hox transcription factors and their elusive mammalian gene targets," Heredity (2006), 97; 88-96.
Takayama et al., "Generation of functional platelets from human embryonic stem cells in vitro via ES-sacs, VEGF-promoted structures that concentrate hematopoietic progenitors," Blood, 1 1 1 (2008); 5298-5306.
Hiroyama Takashi et al., "Establishment of mouse embryonic stem cell-derived erythroid progenitor cell lines able to produce functional red blood cells," PLoS ONE 2008, vol. 3, No. 2, Feb. 1, 2008, pp. 1-11.
Tian, et al., "Cytokine requirements differ for stroma and embryoid body-mediated hematopoiesis from human embryonic stem cells," Experimental Hematology, 32 (2004); 1000-1009.
Van De Velde et al., "The four blastomeres of a 4-cell stage human embryo are able to develop individually into blastocysts with inner cell mass and trophectoderm," Human Reproduction, vol. 23, No. 8, pp. 1742-1747.
Vodyanik et al., "Human embryonic stem cell-derived CD34+ cells: efficient production in the coculture with OP9 stromal cells and analysis of lymphohematopoietic potential," Blood, vol. 105, 2005; 617-626.
Verfaillie et al., "Kinetics of engraftment of CD34(−) and CD34(+) cells from mobilized blood differs from that of CD34," Exper Hematol 2000, vol. 28, No. 9, pp. 1071-1079.
Wang et al., "Endothelial and hematopoietic cell fate of human embryonic stem cells originates from primitve endothelium with hemangioblastic properties," Immunity (2004), vol. 21, No. 1, pp. 31-41.
Wang, "Endothelial and hematopoietic cell fate of human embryonic stem cells," Trends Cardiovasc. Med.; vol. 16, No. 3, 2006, pp. 89-94.
Yuan Weiping, "Stem Cell Science on the Rise in China," Stem Cell, Cell 10, Jan. 6, 2012, pp. 12-15.
Xiong et al., "Developmental Dynamics," 2008,vol. 237, pp. 1218-1231.
Zambidis, et al., "Hematopoietic differentiation of human embryonic stem cells progresses through sequential hematoendothelial, primitive, and definitive stages resembling human yolk sac development," Blood, vol. 106, No. 3, Aug. 1, 2005, pp. 860-870.
EP Exam Report dated Nov. 27, 2012 for 07755391.5.
CN Second Exam Report dated Dec. 25, 2012 for 200980125860.5.
CN Third Exam Report dated Jan. 7, 2013 for 200980125862.4.
AU Exam Report dated Jan. 10, 2013 for 2007238660.
Zhao Huiping et al., Effect of different hemopoietic microenvironment on the differentiation of hemopoietic cells from human embryonic stem cells, J. Cent. South Univ. (Med. Sci.), 2007, vol. 32, No. 6 (abstract only).
Guo et al. Hemangioblastic characteristics of fetal bone marrow-derived Flk1(+) CD31(−)CD34(−) cells. Experimental Hematology. (2003). 31(7):650-658.
Hematti et al. Nonhuman primate embryonic stem cells as a preclinical model for hematopoietic and vascular repair. Experimental Hematology. (2005). 33: 980-986.
Life Technologies. Guidelines for Maintaining Cultured Cells. What is Subculture? (2014). Retrieved from http://www.lifetechnologies.com/us/en/home/references/gibco-cell-culture-basics/cell-cult . . . pp. 1-4.
Qiu et al. Globin switches in yolk sac like primitive and fetal-like definitive red blood cells produced from human embryonic stem cells. Blood (2008). 111(4):2400-2408.
Rajesh et al. Differential requirements for hematopoietic commitment between human and rhesus embryonic stem cells. Stem Cells. (2007). 25:490-499.
Zhou et al. Effect of different hemopoietic microenvironment on the differentiation of hemopoietic cells from human embryonic stem cells. J Cent South Univ (Med Sci). (2007). 32(6):992-996. Abstract Translated Only.
Sauvageau Overexpression of HOXB4 in hempotopoietic cells causes the selective expansion of more primitive populations in vitro and in vivo. Genes & Development (1995). 9:1753-1765.
Cerdan et al. Hematopoietic Differentiation. Embryonic Stem Cells (2007). Chap. 5 (J.R. Masters et al (eds) :53-83.
Lu et al. Protocol for culturing, differentiating and expanding hES-BC cells. Supplemental Protocol. Nature Methods (2007). 4:pp. 1-3.
Kaufman et al. Hematopoietic colong-forming cells derived from human embryonic stem cells. PNAS (2001). 98 (19):10716-10721.
Shinoda et al. a4-Integrin + endothelium derived from primate embryonic stem cells generates primitive and definitive hematopoietic cells. Blood (2007). 109(6):2406-2415.
Umeda et al. Development of primitive and definitive hematopoiesis from non-human primate embryonic stem cells in vitro. Development and Disease (2004). 131(8):1869-1879.
Wernig et al. In vitro reprogramming of fibroblasts into a pluripotent ES-cell-like state.Nature (2007). 448:318-325.
Yu et al. Pluripotent stem cell lines. Genes Dev. (2008). 22:1987-1997.
Douay et al. Stem Cells—A source of adult red blood cells for transfusion purposes: present and future. Crit Care Clin (2009). 25:383-398.
EP Application No. 13180755.4 Extended Search Report dated Mar. 3, 2014; 9 pages.
Huangfu et al. Induction of Pluripotent Stem Cells from Primary Human Fibroblasts with only Oct4 and Sox2. Nature Biotechnology (2008). 26(11): 1269-1275.
Park et al. Reprogramming of Human Somatic Cells to Pluripotency with Defined Factors (2008). 45:141-147.

\* cited by examiner

Figure 7

(SEQ ID NO: 2)

```
   1 ggaaaacgag tcaggggtcg gaataaattt tagtatattt tgtgggcaat tcccagaaat
  61 taatggctat gagttctttt ttgatcaact caaactatgt cgacoccaag ttccctccat
 121 gcgaggaata ttcacagagc gattacctac ccagcgacca ctcgcccggg tactacgccg
 181 gcggccagag gcgagagagc agcttccagc cggaggcggg cttcggcgg cgcgcggcgt
 241 gcaccgtgca gcgctacgcg gcctgccggg accctgggcc cccgccgcct ccgccaccac
 301 ccccgccgcc ccgccaccg cccggtctgt ccccctcgggc tcctgcgccg ccacccgccg
 361 gggccctcct cccggagccc ggccagcgct gcgaggcggt cagcagcagc ccccgccgc
 421 ctccctgcgc ccagaacccc ctgcacccca gcccgtccca ctccgcgtgc aaagagcccg
 481 tcgtctaccc ctggatgcgc aaagttcacg tgagcacggt aaacccccaat tacgccggcg
 541 gggagcccaa gcgctctcgg accgcctaca cgcgccagca ggtcttggag ctggagaagg
 601 aatttcacta caaccgctac ctgacacggc gccggagggt ggagatcgcc cacgcgctct
 661 gcctctccga gcgccagatc aagatctggt tccagaaccg gcgcatgaag tggaaaaaag
 721 accacaagtt gcccaacacc aagatccgct cgggtggtgc ggcaggctca gccggagggc
 781 cccctggccg gcccaatgga ggccccgcg cgctctagtg ccccgcacg cgggagccac
 841 gaacctcggg gtgggcgtgg gcagtgagtg caggggatgg ggtgggggga caggaggggg
 901 ccctgggcc tgggcccgg aaaaatctat ctgccctccc ccacactta tatacgaata
 961 aacgcagaag agggggaggg gaagctttat ttatagaaat gacaatagag ggccacgggg
1021 aggcccccc agaagcaaga ttcaaatctc ttgctttctt tcttaaaaaa aagaaaaaga
1081 aaaagcaaga agaaggagga aagaaaaga cagaaagaga aataggagga ggctgcagct
1141 cctcgttttc agctttggcg aagatggatc cacgtttcat cttaatcac gccaggtcca
1201 ggcccatctg tcttgtttcc tctgccgagg agaagacggg cctcggtggc gaccattacc
1261 tcgacacccg ctaacaaatg aggcccggct cggccgcctc cgcctctgct actgccgctg
1321 ctggaagaca gcctggattt cctttctttg tcccccactc ccgataccca gcgaaagcac
1381 cctctgactg ccagatagtg cagtgttttg gtcacggtaa cacacacaca ctctccctca
1441 tctttcgtgc ccattcactg agggccagaa tgactgctca cccacttcca ccgtgggtt
1501 gggggtgggc aacagaggag gggagcaagt agggaagggg gtggccttga caactcagga
1561 gtgagcagga aaattgagtc caaggaaaaa gagagactca gagacccggg aggcccttcc
1621 tctgaaaggc caagccaagc catgcttggc agggtgaggg gccagttgag ttctgggagc
1681 tgggcactac tctgccagtc cagagttgta cagcagaagc ctctctccta gacgaaaat
1741 gaatgtgaaa ctaggaaata aaatgtgccc ctcccagtct gggaggagga tgttgcagag
1801 ccctctccca tagtttatta tgttgcatcg ttattatta ttattgataa tattattatt
1861 actattttt tgtgtcatgt gagcctctc tcttttctc tttctgacat tccaaaacca
1921 ggccccttcc tacctctggg gctgcttgag tctagaaccc ttcgtatgtg tgaatatctg
1981 tgtgctgtac agagtgacaa tagaaataaa tgtttggttt cttgtgacca gcaaaaaaaa
2041 aa
```

Figure 8

(SEQ ID NO: 4)

```
   1 ggaaaacgag tcagggtcg gaataaattt tagtatattt tgtgggcaat tcccagaaat
  61 taatggctat gagttctttt ttgatcaact caaactatgt cgacccaag ttccctccat
 121 gcgaggaata ttcacagagc gattacctac ccagcgacca ctcgcccggg tactacgccg
 181 gcggccagag gcgagagagc agcttccagc cggaggcgcg cttcgggcgg cgcgcggcgt
 241 gcacgtgca gcgctacgcg gcctgccggg accctgggcc ccgccgcct ccgccaccac
 301 cccgccgcc cccgccaccg cccggtctgt ccctcgggc tcctgcgccc ccacccgccg
 361 gggccctcct cccggagccc ggccagcgct gcgaggcggt cagcagcagc ccccgccgc
 421 ctcctgcgc ccagaaccc ctgcaccca gccgtccca ctccgcgtgc aaagagcccg
 481 tcgtctaccc ctggatgcgc aaagttcacg tgagcacggt aaaccccaat tacgccggcg
 541 gggagcccaa gcgctctcgg accgctaca cgcgccagca ggtcttggag ctggagaagg
 601 aatttcacta caaccgctac ctgacacggc gccggagggt ggagatcgcc cacgcgctct
 661 gcctctccga gcgccagatc aagatctggt tccagaaccg gcgcatgaag tgaaaaaag
 721 accacaagtt gcccaacacc aagatccgct cgggtggtgc ggcaggctca gcggagggc
 781 ccctggccg gcccaatgga ggccccgcg cgctctagtg ccccgcacg cgggagccac
 841 gaacctcggg gtggggtgg gcagtgagtg caggggatgg ggtggggga caggagggg
 901 ccctggggc tgggccccgg aaaaatctat ctgccctccc ccacacttta tatacgaata
 961 aacgcagaag aggggagcg gaagctttat ttatagaaat gacaatagag ggccacgggg
1021 aggccccccc agaagcaaga ttcaaatctc ttgctttctt tcttaaaaaa aagaaaaaga
1081 aaaagcaaga agaaggaaga aagaaaaaga cagaaagaga aataggagga ggctgcagct
1141 cctcgttttc agctttggcg aagatggatc cacgtttcat ctttaatcac gccaggtcca
1201 ggcccatctg tcttgttttcc tctgccgagg agaagacggg cctcggtggc gaccattacc
1261 tcgacacccg ctaacaaatg aggcccggct cggccgcctc cgctctgct actgccgctg
1321 ctggaagaca gcctggattt ccttctttg tccccactc ccgataccca gcgaaagcac
1381 cctctgactg ccagatagtg cagtgtttg gtcacggtaa cacacacaca ctctccctca
1441 tctttcgtgc ccattcactg agggccagaa tgactgctca cccacttcca ccgtggggtt
1501 ggggtgggc aacagaggag gggagcaagt agggaagggg gtggccttga caactcagga
1561 gtgagcaggg aaattgagtc caaggaaaaa gagagactca gagacccggg agggccttcc
1621 tctgaaaggc caagccaagc catgcttggc agggtgaggg gccagttgag ttctgggagc
1681 tgggcactac tctgccagtc cagagttgta cagcagaagc ctctctccta gactgaaat
1741 gaatgtgaaa ctaggaaata aaatgtgccc ctcccagtct gggagagga tgttgcagag
1801 ccctctccca tagtttatta tgttgcatcg tttattatta ttattgataa tattattatt
1861 actattttt tgtgtcatgt gagtcctctc tccttttctc tttctgacat tccaaaacca
1921 ggccccttcc tacctctggg gctgcttgag tctagaaccc ttcgtatgtg tgaatatctg
1981 tgtgctgtac agagtgacaa tagaaataaa tgtttggttt cttgtgaaaa aaaaaaaaaa
```

Figure 9

(SEQ ID NO: 1)

```
   1 MAMSSFLINS NYVDPKFPPC EEYSQSDYLP SDHSPGYYAG GQRRESSFQP EAGFGRRAAC
  61 TVQRYAACRD PGPPPPPPPP PPPPPPPGLS PRAPAPPPAG ALLPEPGQRC EAVSSSPPPP
 121 PCAQNPLHPS PSHSACKEPV VYPWMRKVHV STVNPNYAGG EPKRSRTAYT RQQVLELEKE
 181 FHYNRYLTRR RRVEIAHALC LSERQIKIWF QNRRMKWKKD HKLPNTKIRS GGAAGSAGGP
 241 PGRPNGGPRA L
```

Figure 10

(SEQ ID NO: 3)

```
   1 MAMSSFLINS NYVDPKFPPC EEYSQSDYLP SDHSPGYYAG GQRRESSFQP EAGFGRRAAC
  61 TVQRYAACRD PGPPPPPPPP PPPPPPPGLS PRAPAPPPAG ALLPEPGQRC EAVSSSPPPP
 121 PCAQNPLHPS PSHSACKEPV VYPWMRKVHV STVNPNYAGG EPKRSRTAYT RQQVLELEKE
 181 FHYNRYLTRR RRVEIAHALC LSERQIKIWF QNRRMKWKKD HKLPNTKIRS GGAAGSAGGP
 241 PGRPNGGPRA L
```

FIGURE 11
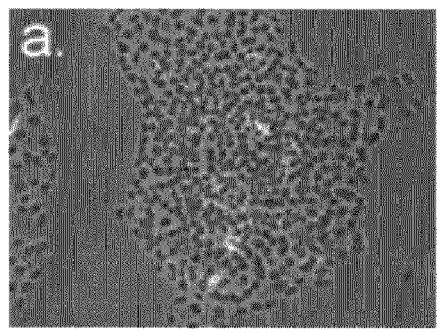
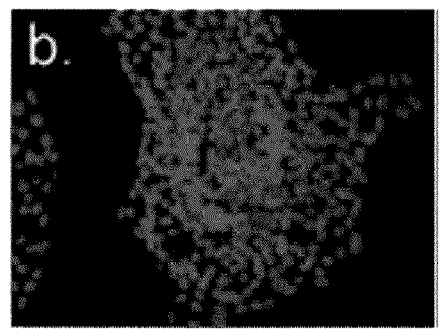
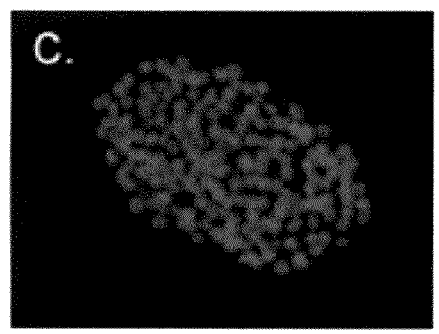
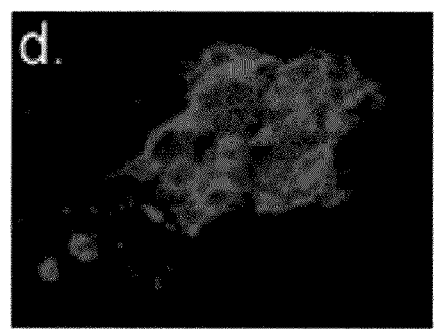
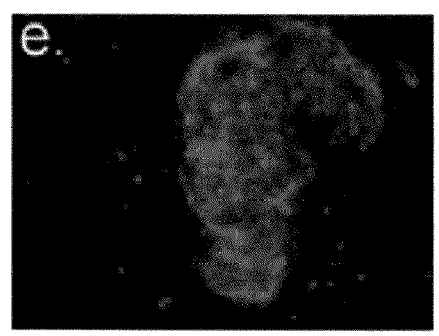

FIGURE 12
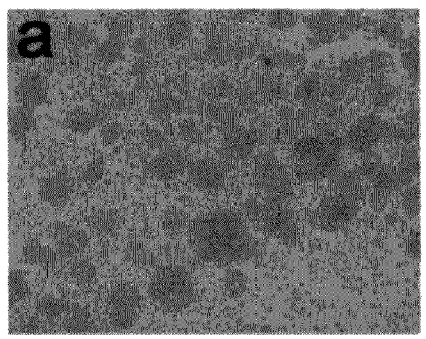
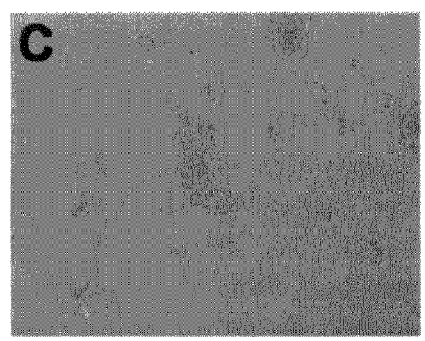
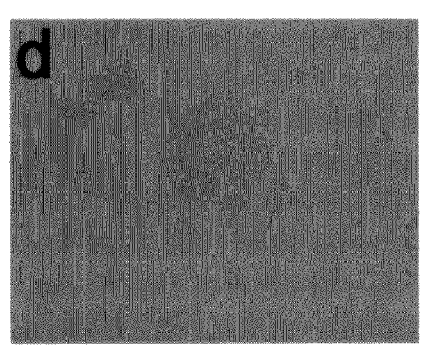
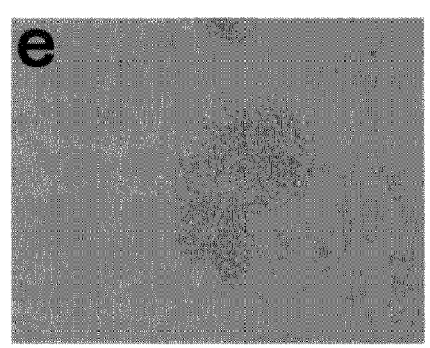
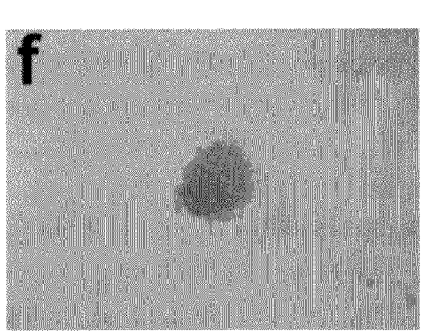

FIGURE 12
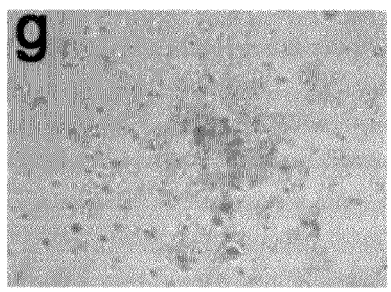
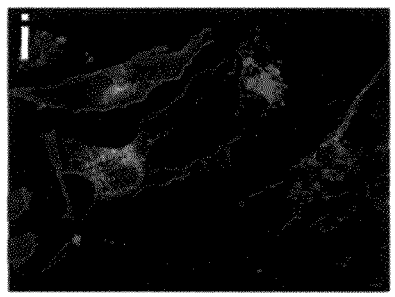
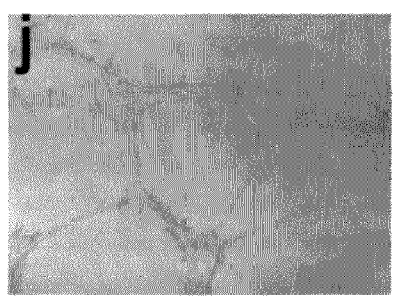

SEQUENCE LISTING

```
<160> NUMBER OF SEQ ID NOS: 33

<210> SEQ ID NO 1
<211> LENGTH: 251
<212> TYPE: PRT
<213> ORGANISM: Homo sapiens

<400> SEQUENCE: 1

Met Ala Met Ser Ser Phe Leu Ile Asn Ser Asn Tyr Val Asp Pro Lys
1               5                   10                  15

Phe Pro Pro Cys Glu Glu Tyr Ser Gln Ser Asp Tyr Leu Pro Ser Asp
                20                  25                  30

His Ser Pro Gly Tyr Tyr Ala Gly Gly Gln Arg Arg Glu Ser Ser Phe
            35                  40                  45

Gln Pro Glu Ala Gly Phe Gly Arg Arg Ala Ala Cys Thr Val Gln Arg
    50                  55                  60

Tyr Ala Ala Cys Arg Asp Pro Gly Pro Pro Pro Pro Pro Pro Pro Pro
65                  70                  75                  80

Pro Pro Pro Pro Pro Pro Gly Leu Ser Pro Arg Ala Pro Ala Pro
                85                  90                  95

Pro Pro Ala Gly Ala Leu Leu Pro Glu Pro Gly Gln Arg Cys Glu Ala
            100                 105                 110

Val Ser Ser Ser Pro Pro Pro Pro Cys Ala Gln Asn Pro Leu His
            115                 120                 125

Pro Ser Pro Ser His Ser Ala Cys Lys Glu Pro Val Val Tyr Pro Trp
    130                 135                 140

Met Arg Lys Val His Val Ser Thr Val Asn Pro Asn Tyr Ala Gly Gly
145                 150                 155                 160

Glu Pro Lys Arg Ser Arg Thr Ala Tyr Thr Arg Gln Gln Val Leu Glu
                165                 170                 175

Leu Glu Lys Glu Phe His Tyr Asn Arg Tyr Leu Thr Arg Arg Arg Arg
            180                 185                 190

Val Glu Ile Ala His Ala Leu Cys Leu Ser Glu Arg Gln Ile Lys Ile
        195                 200                 205

Trp Phe Gln Asn Arg Arg Met Lys Trp Lys Lys Asp His Lys Leu Pro
    210                 215                 220

Asn Thr Lys Ile Arg Ser Gly Gly Ala Ala Gly Ser Ala Gly Gly Pro
225                 230                 235                 240

Pro Gly Arg Pro Asn Gly Gly Pro Arg Ala Leu
                245                 250

<210> SEQ ID NO 2
<211> LENGTH: 2042
<212> TYPE: DNA
<213> ORGANISM: Homo sapiens

<400> SEQUENCE: 2
ggaaaacgag tcagggggtcg gaataaattt tagtatattt tgtgggcaat tcccagaaat      60
```

```
taatggctat gagttctttt ttgatcaact caaactatgt cgaccccaag ttccctccat    120
gcgaggaata ttcacagagc gattacctac ccagcgacca ctcgcccggg tactacgccg    180
gcggccagag gcgagagagc agcttccagc cggaggcggg cttcgggcgg cgcgcggcgt    240
gcaccgtgca cgcgctacgcg gcctgccggg accctgggcc cccgccgcct ccgccaccac    300
ccccgccgcc cccgccaccg cccggtctgt ccctcgggc tcctgcgccg ccacccgccg    360
gggccctcct cccggagccc ggccagcgct gcgaggcggt cagcagcagc ccccgccgc    420
ctccctgcgc ccagaacccc ctgcacccca gcccgtccca ctccgcgtgc aaagagcccg    480
tcgtctaccc ctggatgcgc aaagttcacg tgagcacggt aaaccccaat tacgccggcg    540
gggagcccaa gcgctctcgg accgcctaca cgcgccagca ggtcttggag ctggagaagg    600
aatttcacta caaccgctac ctgacacggg gccggaggt ggagatcgcc cacgcgctct    660
gcctctccga gcgccagatc aagatctggt tccagaaccg gcgcatgaag tggaaaaaag    720
accacaagtt gcccaacacc aagatccgct cgggtggtgc ggcaggctca gccggagggc    780
ccctggccg gcccaatgga ggccccgcg cgctctagtg cccccgcacg cgggagccac    840
gaacctcggg gtggggtgg gcagtgagtg caggggatgg ggtgggggga caggaggggg    900
ccctggggcc tgggccccgg aaaaatctat ctgccctccc ccacactta tatacgaata    960
aacgcagaag aggggaggg gaagctttat ttatagaaat gacaatagag ggccacgggg   1020
aggcccccc agaagcaaga ttcaaatctc ttgctttctt tcttaaaaaa aagaaaaaga   1080
aaagcaaga agaaggaaga aagaaaaaga cagaaagaga ataggagga ggctgcagct   1140
cctcgttttc agctttggcg aagatggatc cacgtttcat cttaatcac gccaggtcca   1200
ggcccatctg tcttgtttcc tctgccgagg agaagacggg cctcggtggc gaccattacc   1260
tcgacaccc ctaacaaatg aggcccggct cggccgcctc cgcctctgct actgccgctg   1320
ctggaagaca gcctggattt cctttctttg tccccactc ccgatacccca gcgaaagcac   1380
cctctgactg ccagatagtg cagtgttttg gtcacggtaa cacacacaca ctctcccctca   1440
tctttcgtgc ccattcactg agggccagaa tgactgctca cccacttcca ccgtggggtt   1500
gggggtgggc aacagaggag gggagcaagt agggaagggg gtggccttga caactcagga   1560
gtgagcagga aaattgagtc caaggaaaaa gagagactca gagacccggg agggccttcc   1620
tctgaaaggc caagccaagc catgcttggc agggtgaggg gccagttgag ttctgggagc   1680
tgggcactac tctgccagtc cagagttgta cagcagaagc ctctctccta gactgaaaat   1740
gaatgtgaaa ctaggaaata aaatgtgccc ctcccagtct gggaggagga tgttgcagag   1800
ccctctccca tagtttatta tgttgcatcg tttattatta ttattgataa tattattatt   1860
actattttt tgtgtcatgt gagtcctctc tccttttctc tttctgacat tccaaaacca   1920
ggcccttcc tacctctggg gctgcttgag tctagaaccc ttcgtatgtg tgaatatctg   1980
tgtgctgtac agagtgacaa tagaaataaa tgtttggttt cttgtgacca gcaaaaaaaa   2040
aa                                                                 2042
```

<210> SEQ ID NO 3
<211> LENGTH: 251
<212> TYPE: PRT
<213> ORGANISM: Homo sapiens

<400> SEQUENCE: 3

```
Met Ala Met Ser Ser Phe Leu Ile Asn Ser Asn Tyr Val Asp Pro Lys
1               5                   10                  15
```

```
Phe Pro Pro Cys Glu Glu Tyr Ser Gln Ser Asp Tyr Leu Pro Ser Asp
                20                  25                  30
His Ser Pro Gly Tyr Tyr Ala Gly Gly Gln Arg Arg Glu Ser Ser Phe
         35                  40                  45
Gln Pro Glu Ala Gly Phe Gly Arg Arg Ala Ala Cys Thr Val Gln Arg
     50                  55                  60
Tyr Ala Ala Cys Arg Asp Pro Gly Pro Pro Pro Pro Pro Pro Pro Pro
65                  70                  75                  80
Pro Pro Pro Pro Pro Pro Gly Leu Ser Pro Arg Ala Pro Ala Pro Pro
                 85                  90                  95
Pro Pro Ala Gly Ala Leu Leu Pro Glu Pro Gly Gln Arg Cys Glu Ala
             100                 105                 110
Val Ser Ser Ser Pro Pro Pro Cys Ala Gln Asn Pro Leu His Pro
         115                 120                 125
Pro Ser Pro Ser His Ser Ala Cys Lys Glu Pro Val Val Tyr Pro Trp
    130                 135                 140
Met Arg Lys Val His Val Ser Thr Val Asn Pro Asn Tyr Ala Gly Gly
145                 150                 155                 160
Glu Pro Lys Arg Ser Arg Thr Ala Tyr Thr Arg Gln Gln Val Leu Glu
                165                 170                 175
Leu Glu Lys Glu Phe His Tyr Asn Arg Tyr Leu Thr Arg Arg Arg Arg
            180                 185                 190
Val Glu Ile Ala His Ala Leu Cys Leu Ser Glu Arg Gln Ile Lys Ile
        195                 200                 205
Trp Phe Gln Asn Arg Arg Met Lys Trp Lys Lys Asp His Lys Leu Pro
210                 215                 220
Asn Thr Lys Ile Arg Ser Gly Gly Ala Ala Gly Ser Ala Gly Gly Pro
225                 230                 235                 240
Pro Gly Arg Pro Asn Gly Gly Pro Arg Ala Leu
                245                 250

<210> SEQ ID NO 4
<211> LENGTH: 2040
<212> TYPE: DNA
<213> ORGANISM: Homo sapiens

<400> SEQUENCE: 4
ggaaaacgag tcaggggtcg gaataaattt tagtatattt tgtgggcaat tcccagaaat     60
taatggctat gagttctttt ttgatcaact caaactatgt cgaccccaag ttccctccat    120
gcgaggaata ttcacagagc gattacctac ccagcgacca ctcgcccggg tactacgccg    180
gcggccagag gcgagagagc agcttccagc cggaggcggg cttcgggcgg cgcgcggcgt    240
gcaccgtgca gcgctacgcg gcctgccggg accctgggcc cccgccgcct ccgccaccac    300
ccccgccgcc cccgccaccg cccggtctgt ccctcgggc tcctgcgccg ccacccgccg    360
gggccctcct cccggagccc ggccagcgct gcgaggcggt cagcagcagc ccccgccgc    420
ctccctgcgc ccagaacccc ctgcacccca gccgtccca ctccgcgtgc aaagagcccg    480
tcgtctaccc ctggatgcgc aaagttcacg tgagcacggt aaaccccaat tacgccggcg    540
gggagcccaa gcgctctcgg accgcctaca cgcgccagca ggtcttggag ctggagaagg    600
aatttcacta caaccgctac ctgacacggc gccggaggcgt ggagatcgcc cacgcgctct    660
gcctctccga gcgccagatc aagatctggt tccagaaccg cgcatgaag tggaaaaaag    720
accacaagtt gcccaacacc aagatccgct cgggtggtgc ggcaggctca gccggagggc    780
```

```
cccctggccg gcccaatgga ggcccccgcg cgctctagtg cccccgcacg cgggagccac    840
gaacctcggg gtggggtgg gcagtgagtg caggggatgg ggtgggggga caggaggggg     900
ccctggggcc tgggccccgg aaaaatctat ctgccctccc ccacactttta tatacgaata   960 aacgcagaag aggggaggg gaagctttat ttatagaaat gacaatagag ggccacgggg    1020
aggccccccc agaagcaaga ttcaaatctc ttgctttctt tcttaaaaaa aagaaaaaga   1080
aaaagcaaga agaaggaaga aagaaaaaga cagaaagaga aataggagga ggctgcagct   1140
cctcgttttc agctttggcg aagatggatc cacgtttcat ctttaatcac gccaggtcca   1200
ggcccatctg tcttgtttcc tctgccgagg agaagacggg cctcggtggc gaccattacc   1260
tcgacacccg ctaacaaatg aggcccggct cggccgcctc cgcctctgct actgccgctg   1320
ctggaagaca gcctggattt cctttctttg tcccccactc ccgataccca gcgaaagcac   1380
cctctgactg ccagatagtg cagtgttttg gtcacggtaa cacacacaca ctctccctca   1440
tctttcgtgc ccattcactg agggccagaa tgactgctca cccacttcca ccgtgggtt    1500 gggggtgggc aacagaggag gggagcaagt agggaagggg gtggccttga caactcagga   1560
gtgagcaggg aaattgagtc caaggaaaaa gagagactca gagacccggg agggccttcc   1620
tctgaaaggc caagccaagc catgcttggc agggtgaggg gccagttgag ttctgggagc   1680
tgggcactac tctgccagtc cagagttgta cagcagaagc ctctctccta gactgaaaat   1740
gaatgtgaaa ctaggaaata aaatgtgccc ctcccagtct ggggaggagga tgttgcagag   1800 ccctctccca tagtttatta tgttgcatcg tttattatta ttattgataa tattattatt    1860 actattttt tgtgtcatgt gagtcctctc tccttttctc tttctgacat tccaaaacca    1920 ggcccccttcc tacctctggg gctgcttgag tctagaaccc ttcgtatgtg tgaatatctg   1980
tgtgctgtac agagtgacaa tagaaataaa tgtttggttt cttgtgaaaa aaaaaaaaaa   2040
```

<210> SEQ ID NO 5
<211> LENGTH: 11
<212> TYPE: PRT
<213> ORGANISM: Human immunodeficiency virus

<400> SEQUENCE: 5

Tyr Gly Arg Lys Lys Arg Arg Gln Arg Arg Arg
1               5                   10

<210> SEQ ID NO 6
<211> LENGTH: 9
<212> TYPE: PRT
<213> ORGANISM: Human immunodeficiency virus

<400> SEQUENCE: 6

Arg Lys Lys Arg Arg Gln Arg Arg Arg
1               5

<210> SEQ ID NO 7
<211> LENGTH: 11
<212> TYPE: PRT
<213> ORGANISM: Artificial
<220> FEATURE:
<223> OTHER INFORMATION: synthetic construct

<400> SEQUENCE: 7

Tyr Ala Arg Lys Ala Arg Arg Gln Ala Arg Arg
1               5                   10

<210> SEQ ID NO 8

```
<211> LENGTH: 11
<212> TYPE: PRT
<213> ORGANISM: Artificial
<220> FEATURE:
<223> OTHER INFORMATION: synthetic construct

<400> SEQUENCE: 8

Tyr Ala Arg Ala Ala Ala Arg Gln Ala Arg Ala
1               5                   10

<210> SEQ ID NO 9
<211> LENGTH: 11
<212> TYPE: PRT
<213> ORGANISM: Artificial
<220> FEATURE:
<223> OTHER INFORMATION: synthetic construct

<400> SEQUENCE: 9

Tyr Ala Arg Ala Ala Arg Arg Ala Ala Arg Arg
1               5                   10

<210> SEQ ID NO 10
<211> LENGTH: 11
<212> TYPE: PRT
<213> ORGANISM: Artificial
<220> FEATURE:
<223> OTHER INFORMATION: synthetic construct

<400> SEQUENCE: 10

Arg Ala Arg Ala Ala Arg Arg Ala Ala Arg Ala
1               5                   10

<210> SEQ ID NO 11
<211> LENGTH: 16
<212> TYPE: PRT
<213> ORGANISM: Drosophila antennapedia

<400> SEQUENCE: 11

Arg Gln Ile Lys Ile Trp Phe Gln Asn Arg Arg Met Lys Trp Lys Lys
1               5                   10                  15

<210> SEQ ID NO 12
<211> LENGTH: 34
<212> TYPE: PRT
<213> ORGANISM: Herpes simplex virus 1

<400> SEQUENCE: 12

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 13
<211> LENGTH: 7
<212> TYPE: PRT
<213> ORGANISM: Artificial
<220> FEATURE:
<223> OTHER INFORMATION: synthetic construct

<400> SEQUENCE: 13

Arg Arg Arg Arg Arg Arg Arg
1               5

<210> SEQ ID NO 14
```

```
<211> LENGTH: 11
<212> TYPE: PRT
<213> ORGANISM: Artificial
<220> FEATURE:
<223> OTHER INFORMATION: synthetic construct

<400> SEQUENCE: 14

Tyr Ala Arg Ala Ala Ala Arg Gln Ala Arg Ala
1               5                   10

<210> SEQ ID NO 15
<211> LENGTH: 11
<212> TYPE: PRT
<213> ORGANISM: Artificial
<220> FEATURE:
<223> OTHER INFORMATION: synthetic construct

<400> SEQUENCE: 15

Tyr Ala Arg Ala Ala Ala Arg Gln Ala Arg Ala
1               5                   10

<210> SEQ ID NO 16
<211> LENGTH: 20
<212> TYPE: DNA
<213> ORGANISM: Homo sapiens

<400> SEQUENCE: 16
gaaggtattc agccaaacgc                                         20

<210> SEQ ID NO 17
<211> LENGTH: 20
<212> TYPE: DNA
<213> ORGANISM: Homo sapiens

<400> SEQUENCE: 17
gttacagaac cacactcgga                                         20

<210> SEQ ID NO 18
<211> LENGTH: 20
<212> TYPE: DNA
<213> ORGANISM: Homo sapiens

<400> SEQUENCE: 18
tgcttccctg agacccagtt                                         20

<210> SEQ ID NO 19
<211> LENGTH: 25
<212> TYPE: DNA
<213> ORGANISM: Homo sapiens

<400> SEQUENCE: 19
gatcacttct ttcctttgca tcaag                                   25

<210> SEQ ID NO 20
<211> LENGTH: 20
<212> TYPE: DNA
<213> ORGANISM: Homo sapiens

<400> SEQUENCE: 20
ccgagtccag gatccaggta                                         20

<210> SEQ ID NO 21
<211> LENGTH: 19
<212> TYPE: DNA
<213> ORGANISM: Homo sapiens
```

```
<400> SEQUENCE: 21
ctctgacgcc gagacttgg                                                19

<210> SEQ ID NO 22
<211> LENGTH: 19
<212> TYPE: DNA
<213> ORGANISM: Homo sapiens

<400> SEQUENCE: 22
ccagccaagc tgtctcagt                                                19

<210> SEQ ID NO 23
<211> LENGTH: 20
<212> TYPE: DNA
<213> ORGANISM: Homo sapiens

<400> SEQUENCE: 23
ctgcatgtca ggttgcaaag                                               20

<210> SEQ ID NO 24
<211> LENGTH: 20
<212> TYPE: DNA
<213> ORGANISM: Homo sapiens

<400> SEQUENCE: 24
gagtcctgct gacccttctg                                               20

<210> SEQ ID NO 25
<211> LENGTH: 19
<212> TYPE: DNA
<213> ORGANISM: Homo sapiens

<400> SEQUENCE: 25
attttgcacc gtccagtcc                                                19

<210> SEQ ID NO 26
<211> LENGTH: 21
<212> TYPE: DNA
<213> ORGANISM: Homo sapiens

<400> SEQUENCE: 26
atgagatgga gattactgat g                                             21

<210> SEQ ID NO 27
<211> LENGTH: 19
<212> TYPE: DNA
<213> ORGANISM: Homo sapiens

<400> SEQUENCE: 27
gccccgttca cattctgct                                                19

<210> SEQ ID NO 28
<211> LENGTH: 18
<212> TYPE: DNA
<213> ORGANISM: Homo sapiens

<400> SEQUENCE: 28
aactgggccg gaagctct                                                 18

<210> SEQ ID NO 29
<211> LENGTH: 23
<212> TYPE: DNA
```

```
<213> ORGANISM: Homo sapiens

<400> SEQUENCE: 29
cttgaaacat tccaggtgat aca                                              23

<210> SEQ ID NO 30
<211> LENGTH: 19
<212> TYPE: DNA
<213> ORGANISM: Homo sapiens

<400> SEQUENCE: 30
cgatgctggc gctgagtac                                                   19

<210> SEQ ID NO 31
<211> LENGTH: 19
<212> TYPE: DNA
<213> ORGANISM: Homo sapiens

<400> SEQUENCE: 31
ccaccactga cacgttggc                                                   19

<210> SEQ ID NO 32
<211> LENGTH: 20
<212> TYPE: DNA
<213> ORGANISM: Homo sapiens

<400> SEQUENCE: 32
gcgggaaatc gtgcgtgaca                                                  20

<210> SEQ ID NO 33
<211> LENGTH: 22
<212> TYPE: DNA
<213> ORGANISM: Homo sapiens

<400> SEQUENCE: 33
gatggagttg aaggtagttt cg                                               22
```

HEMANGIO COLONY FORMING CELLS AND NON-ENGRAFTING HEMANGIO CELLS

CROSS-REFERENCE TO RELATED APPLICATIONS

This application is the National Phase of International Application PCT/US09/43043, filed May 6, 2009, which designated the U.S. and that International Application was published under PCT Article 21(2) in English. This application also includes a claim of priority under 35 U.S.C. §119(e) to U.S. provisional patent application No. 61/126,802, filed May 6, 2008, and U.S. provisional patent application No. 61/190,282, filed Aug. 26, 2008.

FIELD OF INVENTION

The present invention generally relates to methods for generating and expanding human hemangio colony forming cells and non-engrafting hemangio cells.

Particularly, the invention relates to a method of generating and expanding human hemangio-colony forming cells in vitro using a two-step process by first, culturing human embryo-derived stem cells in serum-free media in the presence of at least one growth factor in an amount sufficient to induce the differentiation of embryonic stem cells into embryoid bodies, and second, culturing the embryoid bodies in serum-free media in the presence of at least one growth factor in an amount sufficient to expand human hemangio-colony forming cells in the medium comprising embryoid bodies.

The invention also relates to a method of generating and expanding human non-engrafting hemangio cells in vitro.

The invention additionally relates to preparations of human hemangio-colony forming cells and non-engrafting hemangio cells. The invention further relates to methods of differentiating human hemangio-colony forming units and non-engrafting hemangio cells along a hematopoietic or endothelial lineage, as well as methods of preparing partially or fully differentiated cell types from hemangio-colony forming cells and non-engrafting hemangio cells. Hemangio-colony forming cells, non-engrafting hemangio cells, and cells differentiated therefrom, have a variety of uses in vitro and in vivo. The ability to generate expanded human hemangio-colony forming cells and non-engrafting hemangio cells in such large quantities in vitro provides for the first time the potential to derive large numbers of human hemangio-colony forming and non-engrafting hemangio derivative cell types, such as human hematopoietic stem cells, or endothelial cells, differentiated hematopoietic cells, such as red blood cells and platelets, that will be useful in various therapeutic applications. Furthermore, the expanded numbers of human hemangio-colony forming cells and non-engrafting hemangio cells derived by the present invention may be utilized in novel therapeutic strategies in the treatment of hematopoietic and endothelial cell disorders or in blood banking.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Hematopoietic stem cells (HSCs) are capable of self-renewal and are able to give rise to all blood cell lineages. These cells, which reside in the bone marrow, form the basis of the adult hematopoietic system. The transplantation of these cells represents the most common cell-based therapy applied today in the clinic.

HSC transplantation is used for the treatment of patients with acute or chronic leukemia, aplastic anemia and various immunodeficiency syndromes, as well as various non-hematological malignancies and auto-immune disorders. For patients with hematological malignancies, HSC transplantation may rescue patients from treatment-induced aplasia, which can occur following high-dose chemotherapy and/or radiotherapy.

Despite the widespread clinical utility of HSC transplantation, the three major sources of HSCs (human bone marrow, mobilized peripheral blood, and umbilical cord blood) are limited as two-thirds of the patients in need of somatic HSC transplantation lack well-matched donors. For example, for any given patient, there is only a 25% chance that a sibling is a human leukocyte antigen (HLA)-identical match.

HLAs are proteins on a cell's surface that help the immune system identify the cells as either self (belonging to the body) or non-self (foreign or from outside the body). The HLA proteins are encoded by clusters of genes that form a region located on human chromosome 6 known as the Major Histocompatibility Complex, or MHC, in recognition of the important role of the proteins encoded by the MHC loci in graft rejection. Accordingly, the HLA proteins are also referred to as MHC proteins. Although matching the MHC molecules of a transplant to those of the recipient significantly improves the success rate of clinical transplantation, it does not prevent rejection, even when the transplant is between HLA-identical siblings. Such rejection may be triggered by differences between the minor Histocompatibility antigens. These polymorphic antigens are usually "non-self" peptides bound to MHC molecules on the cells of the transplant tissue, and differences between minor Histocompatibility antigens will often cause the immune system of a transplant recipient to eventually reject a transplant, even where there is a match between the MHC antigens, unless immunosuppressive drugs are used.

There are three types each of class I and class II HLA. A person (typically a sibling) who has a class I and class II HLA match is called a related donor. Increased survival is associated with a match between recipient and donor class I HLA-A, HLA-B, HLA-C, and class II HLA-DRB1 and HLA-DQB1 (Morishima, et al., 2002 *Blood* (99):4200-6). For a patient who does not have a matched, related donor, a search through donor banks may provide a person with matching HLA types. However the number of people in need of a cell or tissue transplant, such as an HSC transplant, is far greater than the available supply of cells and tissues suitable for transplantation. Under these circumstances, it is not surprising that obtaining a good match between the MHC proteins of a recipient and those of the transplant is frequently impossible. Therefore, many transplant recipients must wait for an MHC-matched transplant to become available or accept a transplant that is not MHC-matched and endure higher doses of immunosuppressive drugs and still risk rejection. The ability to generate and manipulate HSCs, and/or to induce tolerance in recipients of transplants, therefore, will greatly benefit the treatment and management of human disease.

Based on work in the avian embryo, and subsequently in frogs and mammals, it has been demonstrated that the developmental programs of blood and endothelium are closely linked. For example, endothelial and hematopoietic cells emerge concurrently and in close proximity in yolk sac blood islands. The yolk sac blood islands derive from aggregates of mesodermal cells that colonize the yolk sac. The center of these aggregates gives rise to the embryonic hematopoietic cells whereas the peripheral population differentiates into endothelial cells which form the vasculature that surrounds the inner blood cells. These observations support the notion that endothelial and hematopoietic cells have a common precursor.

Additionally, in zebrafish and mouse embryos, both endothelial and hematopoietic lineages share the expression of certain genes, such as Flk1, Flt1, Tie1, Tie2, CD34, Scl, and Runx1 (Fina et al. 1990 *Blood* (75): 2417-2426; Millauer et al. 1993 *Cell* (72): 835-846; Yamaguchi et al. 1993 *Development* (118): 489-498; Anagnostou et al. 1994 *PNAS USA* (91): 3974-3978; Kallianpur et al. 1994 *Blood* (83): 1200-12081; Young et al. 1995 *Blood* (85): 96-105, Asahara et al. 1997 *Science* (275): 964-967; Kabrun et al., 1997 *Development* (124): 2039-2048). Likewise certain gene mutations affect both endothelial and hematopoietic cell development (Shalaby et al. 1995 *Nature* (376): 62-66; Robb et al. 1995 PNAS USA (92): 7075-7079; Shivdasani et al. 1995 Nature (373): 432-434; Stainier et al. 1995 Development (121): 3141-3150; Bollerot et al., 2005 *APMIS* (113): 790-803). Further, the deletion of either Flk1 or Flt1, which are both receptors for vascular endothelial growth factor (VEGF), results in a disruption of hematopoietic and endothelial development in the mouse embryo.

The generation of mouse hemangioblasts from mouse embryonic stem cells in vitro has been reported in the literature (Choi et al. 1998 *Development* 125: 727-732). Further, human precursor cells capable of giving rise to both hematopoietic and endothelial cells have been derived from human ES cells (Wang et al. 2004 *Immunity* (21): 31-41 and Wang et al. *J Exp Med* (201): 1603-1614), but only in small quantities, hundreds of cells at best. Moreover, no method or conditions exist for the expansion of the hemangioblast precursor cells in vitro.

Despite the prior identification of cell types capable of giving rise to cells of the hematopoietic lineage, there remains a need for improved methods of generating large numbers of progenitor cell populations, as well as differentiated cell types. The present invention addresses this need. Additionally, the present invention provides a novel progenitor cell type that does not engraft into the bone marrow when delivered in vivo to an immunodeficient animal. However, despite the inability of these cells to engraft into the bone marrow, the cells are capable of generating differentiated hematopoietic cells, and may even be capable of generating other non-hematopoietic cells types such as endothelial cell types, skeletal muscle, and smooth muscle.

There is additionally a critical need for available blood for transfusion. The Red Cross and other suppliers of blood report a near constant shortage of blood. This is especially true for patients with unique blood types, patients who are Rh+, or following accidents or disasters resulting in mass casualties. Additionally, in times of war, the military has an acute need for available blood for use in the treatment of traumatic war-related injuries. The present invention provides differentiated hematopoietic cells for use in blood banking and transfusion. The cells and methods of the present invention will provide a safe and reliable advance beyond the traditional reliance on blood donations, and will help prevent critical shortages in available blood.

Thus, there remains a need for methods for generating and expanding large numbers of human hemangioblasts as well as hemangioblast derivative cell types, i.e., hematopoietic and endothelial cells, and all solutions/mixtures containing such quantities of hemangioblasts or derivative cell types. Such methods would increase the availability of cells for transplantation as well as have utility in a variety of other therapeutic applications, such as in induction of immunological tolerance.

SUMMARY OF THE INVENTION

The following embodiments and aspects thereof are described and illustrated in conjunction with compositions and methods which are meant to be exemplary and illustrative, not limiting in scope.

Various embodiments of the present invention overcomes the problems described in the background section above by providing a method of generating and expanding human hemangioblasts or hemangio-colony forming cells in vitro. The ability to expand human hemangioblasts or hemangio-colony forming cells by the novel methods disclosed herein allows the production of cells that can be used in various therapeutic applications. Additionally, the present invention provides methods for generating human hemangioblast or hemangio-colony forming lineage cells (i.e., hematopoietic and endothelial cells) that may be used in therapeutic applications. The methods of the invention provide further utility in that they enable the generation of large numbers of human hemangioblasts or hemangio-colony forming cells as well as hematopoietic and endothelial cells, and cells differentiated therefrom, that may be used at commercial scale. The methods of the present invention represents a significant improvement in generating hemangioblasts and although simplified from previous methods, results in an 8-fold increase in yield over the methods of WO 2007/120811.

The present invention provides for a method for generating and expanding human hemangio-colony forming cells in vitro, said method comprising the steps of: a) culturing a cell culture comprising human pluripotent stem cells in serum-free media in the presence of at least one growth factor in an amount sufficient to induce the differentiation of said pluripotent stem cells into embryoid bodies; and (b) adding at least two growth factors to said culture comprising embryoid bodies and continuing to culture said culture in serum-free media, wherein said growth factor is in an amount sufficient to expand human hemangio-colony forming cells in said embryoid bodies culture, wherein said stem cells, embryoid bodies and hemangio-colony forming cells are grown in serum-free media throughout steps (a) and (b) of said method, and wherein said at least two growth factors in step (b) comprise BMP4 and VEGF.

This invention also provides a method for generating and expanding human hemangio-colony forming cells in vitro, said method comprising the steps of: (a) culturing a cell culture comprising human pluripotent stem cells in serum-free media in the presence of at least one growth factor in an amount sufficient to induce the differentiation of said pluripotent stem cells into embryoid bodies; (b) adding at least two growth factors to said culture comprising embryoid bodies and continuing to culture said culture in serum-free media, wherein said growth factor is in an amount sufficient to expand human hemangio-colony forming cells in said embryoid bodies culture, (c) said embryoid bodies are disaggregated into single cells; and (d) adding at least one growth factor to said culture comprising said single cells and continuing to culture said culture in serum-free media, wherein said growth factor is in an amount sufficient to expand human hemangio-colony forming cells in said culture comprising said single cells, wherein said stem cells, embryoid bodies and hemangio-colony forming cells are grown in serum-free media throughout steps (a)-(d) of said method, and wherein said at least two growth factors in step (b) comprise BMP4 and VEGF. In certain embodiments, the method further comprises the step of adding erythropoietin (EPO) to steps (b) and (d).

In certain embodiments of the invention, the pluripotent stem cell is an embryonic stem cell.

In certain embodiments of the methods for generating and expanding human hemangio-colony forming cells of this invention, the growth factor is a protein that comprises a homeobox protein, or a functional variant or an active fragment thereof. In certain embodiments, the homeobox protein is a protein that comprises HOXB4, or a functional variant or an active fragment thereof. It is contemplated that the HOXB4 could be mammalian HOXB4, including mouse and human HOXB4. The HOXB4 protein could be full length HOXB4 protein. In yet further embodiments, the HOXB4 comprises the amino acid sequence of SEQ ID NO: 1 (FIG. 9) or SEQ ID NO: 3 (FIG. 10).

In certain embodiments of the methods for generating and expanding human hemangio-colony forming cells of this invention, the growth factor that comprises HOXB4 is a fusion protein that comprises HOXB4 and a protein transduction domain (PTD). In yet further embodiments, the PTD and the HOXB4 are conjugated via a linker. In yet further embodiments, the PTD is TAT protein, a functional variant or an active fragment thereof (including a TAT polypeptide). In certain embodiments, the TAT protein comprises the amino acid sequence of SEQ ID NO: 14. In yet further embodiments, the PTD comprises one or more copies of a TAT polypeptide with the amino acid sequence of SEQ ID NO: 14. In certain embodiments, the PTD is SEQ ID NO: 15.

In certain embodiments of the methods for generating and expanding human hemangio-colony forming cells of this invention, the growth factor is selected from the group consisting of vascular endothelial growth factor (VEGF), bone morphogenic proteins (BMP), stem cell factor (SCF), Flt-3L (FL) thrombopoietin (TPO) and erythropoietin (EPO). In further embodiments, vascular endothelial growth factor (VEGF) or bone morphogenic protein (BMP), or both, are added to culturing step (a) within 0-48 hours of culturing the cell culture comprising the hES cells. In still other further embodiments, the stem cell factor (SCF), Flt-3L (FL) or thrombopoietin (TPO), or any combination thereof, are added to the cell culture comprising hES cells within 48-72 hours from the start of culturing step (a).

In certain embodiments of the methods for generating and expanding human hemangio-colony forming cells of this invention, a growth factor that comprises a HOXB4 protein, or a functional variant or active fragment (or domain) thereof, is added to the step(s) in which said protein is added multiple times, such as, for example, once a day or once every other day.

In certain embodiments of the methods for generating and expanding human hemangio-colony forming cells of this invention, the growth factor comprising a homeobox protein is added to step (b) within 48-72 hours from the start of step (a). In certain embodiments of the methods of this invention, the HOXB4 protein, or functional variants or active fragments thereof, is added to step (b) within 48-72 hours from the start of step (a).

In certain embodiments, the methods for generating and expanding human hemangio-colony forming cells of this invention further comprise the step of adding erythropoietin (EPO) to step (b).

In certain embodiments, the methods for generating and expanding human hemangio-colony forming cells of this invention further comprise the step(s) of purifying and/or isolating the human hemangio-colony forming cells. The hemangio-colony forming cells may be purified by using immunoaffinity column chromatography with an anti-CD71 antibody. The hemangio-colony forming cells may be isolated by size and/or by morphology.

In certain embodiments of the methods for generating and expanding human hemangio-colony forming cells of this invention, the cell culture comprising human embryo-derived stem cells are derived from a library of human embryonic stem cells, wherein said library of human embryonic stem cells comprises stem cells, each of which is hemizygous or homozygous for at least one MHC allele present in a human population, wherein each member of said library of stem cells is hemizygous or homozygous for a different set of MHC alleles relative to the remaining members of the library. In further embodiments, the library of human embryonic stem cells comprises stem cells that are hemizygous or homozygous for all MHC alleles present in a human population. These methods generate a library of human hemangio-colony forming cells, each of which is hemizygous or homozygous for at least one MHC allele present in a human population, wherein each member of said library of stem cells is hemizygous or homozygous for a different set of MHC alleles relative to the remaining members of the library. In further embodiments, these methods generate a library of human hemangio-colony forming cells that are hemizygous or homozygous for all MHC alleles present in a human population. Thus, this invention also provides a library of human hemangio-colony forming cells made by such methods. This library could be used as follows.

This invention provides a method to treat a human patient in need of treatment involving administering human hematopoietic stem cells or human endothelial cells to said patient, comprising the steps of: (a) selecting said patient; (b) identifying MHC proteins expressed on the surface of said patient's cells; (c) providing a library of human hemangio-colony forming cells described in the preceding paragraph; (d) selecting the human hemangio-colony forming cells from the library that match said patient's MHC proteins on said patient's cells; (e) differentiating said human hemangio-colony forming cells identified in step (d) into human hematopoietic stem cells, endothelial cells or both, depending on need; (f) administering said human hematopoietic stem cells, endothelial cells or both from step (e) to said patient. This method could be performed in a regional center, such as a hospital or a medical center, or any other suitable facility.

In certain embodiments, the methods for generating and expanding human hemangio-colony forming cells of this invention further comprise the step of growing the human hemangio-colony forming cells under conditions suitable to induce the differentiation of said human hemangio-colony forming cells into human hematopoietic stem cells.

In certain embodiments, the methods for generating and expanding human hemangio-colony forming cells of this invention further comprise the step of growing said human hemangio-colony forming cells under conditions suitable to induce the differentiation of said human hemangio-colony forming cells into human endothelial cells. In further embodiments, the condition suitable to induce the differentiation of said human hemangio-colony forming cells into human endothelial cells comprises growing the human hemangio-colony forming cells on fibronectin-coated culture plates.

In certain embodiments of this invention, the methods for generating and expanding human hemangio-colony forming cells result in at least 10,000 human hemangio-colony forming cells, at least 50,000 human hemangio-colony forming cells, at least 100,000 human hemangio-colony forming cells, at least 500,000 human hemangio-colony forming cells, at least $1 \times 10^6$ human hemangio-colony forming cells, at least $2 \times 10^6$ human hemangio-colony forming cells, at least $3 \times 10^6$ human hemangio-colony forming cells or at least $4 \times 10^6$ human hemangio-colony forming cells. These methods result in cell solutions that may comprise between 10,000 to 4 million human hemangio-colony forming cells.

Thus, this invention also provides a solution of human hemangio-colony forming cells (which could be grown in serum-free media) comprising at least 10,000 human hemangio-colony forming cells, at least 50,000 human hemangio-colony forming cells, at least 100,000 human hemangio-colony forming cells, at least 500,000 human hemangio-colony forming cells, at least $1 \times 10^6$ human hemangio-colony forming cells, at least $2 \times 10^6$ human hemangio-colony forming cells, at least $3 \times 10^6$ human hemangio-colony forming cells or at least $4 \times 10^6$ human hemangio-colony forming cells. These solutions could be injectable to a subject. These solutions could be suitable for freezing. These solutions could be serum-free. The human hemangio-colony forming cells in these solutions are capable of differentiating into at least hematopoietic and endothelial cells but have greater developmental potential to differentiate into other cell types. This invention also provides a use of these solutions for the manufacture of a medicament to treat a disease that could be treated by the administration of hemangio-colony forming cells, hematopoietic cells or endothelial cells.

This invention also provides a method of producing a solution of human hemangio-colony forming cells suitable for injection into a patient comprising the steps of isolating the solution of cells described in the preceding paragraph and placing the cells into a solution suitable for injection into a patient. This invention also provides a method of producing a solution of human hemangio-colony forming cells suitable for freezing comprising the steps of isolating the solution of cells described in the preceding paragraph and placing the cells into a solution suitable for freezing.

This invention also provides a method for administering human hematopoietic stem cells to a patient in need thereof, comprising the steps of: (a) selecting a patient in need thereof; (b) supplying human hemangio-colony forming cells generated and expanded by a method of this invention; (c) differentiating said human hemangio-colony forming cells into human hematopoietic stem cells; and (d) administering some of all of said human hematopoietic stem cells to said patient.

This invention also provides a method for administering human hematopoietic stem cells to a patient in need thereof, comprising the steps of: (a) selecting the patient in need thereof; (b) supplying human hemangio-colony forming cells in an amount of at least 10,000 cells; (c) differentiating said human hemangio-colony forming cells into human hematopoietic stem cells; and (d) administering some or all of said human hematopoietic stem cells to said patient.

This invention also provides a method for administering human endothelial cells into a patient in need thereof, comprising the steps of: (a) selecting a patient in need thereof; (b) supplying human hemangio-colony forming cells generated and expanded by a method of this invention; (c) differentiating said human hemangio-colony forming cells into human endothelial cells; and (d) administering some or all of said human endothelial cells to said patient.

This invention also provides a method for administering human endothelial cells into a patient in need thereof, comprising the steps of: (a) selecting a patient in need thereof; (b) supplying human hemangio-colony forming cells in an amount of at least 10,000 cells; (c) differentiating said human hemangio-colony forming cells into human endothelial cells; and (d) administering some or all of said human endothelial cells to said patient. In certain embodiments, the human hemangio-colony forming cells are in an amount between 10,000 to 4 million cells.

This invention also provides a method for treating an endothelial cell disorder in a patient in need thereof, comprising the steps of: (a) selecting a patient in need thereof; (b) supplying human hemangio-colony forming cells generated and expanded by a method described above; (c) differentiating said human hemangio-colony forming cells into human endothelial cells; and (d) administering some or all of said human endothelial cells to said patient.

This invention also provides a method for treating an endothelial cell disorder in a patient in need thereof, comprising the steps of: (a) selecting a patient in need thereof; (b) supplying human hemangio-colony forming cells in an amount of at least 10,000 cells; (c) differentiating said human hemangio-colony forming cells into human endothelial cells; and (d) administering some or all of said human endothelial cells to said patient. In certain embodiments, the human hemangio-colony forming cells are in an amount between 10,000 to 4 million cells.

The endothelial cell disorder to be treated by these methods includes myocardium infarction, stroke, atherosclerosis and ischemia. The ischemia could occur in the brain, limbs, heart, lungs, skin and eye.

This invention provides a method for producing human hematopoietic stem cells in vitro, comprising the steps of: (a) supplying human hemangio-colony forming cells generated and expanded by a method of this invention; and (b) growing said human hemangio-colony forming cells under conditions suitable to induce the differentiation of said human hemangio-colony forming cells into human hematopoietic stem cells.

This invention also provides a method for producing human endothelial cells in vitro, comprising the steps of: (a) supplying human hemangio-colony forming cells generated and expanded by a method of this invention; and (b) growing said human hemangio-colony forming cells under conditions suitable to induce the differentiation of said human hemangio-colony forming cells into human endothelial cells.

This invention also provides a method for expanding hemangio-colony forming cells comprising growing mammalian hemangio-colony forming cells in serum-free media in the presence of a protein that comprises a homeobox protein (such as HOXB4) or a functional equivalent or an active fragment thereof in an amount sufficient to support the proliferation of said hemangioblast cells. The hemangio-colony forming cells to be expanded could be enriched, purified, or isolated from cord blood, peripheral blood, or bone marrow. The hemangio-colony forming cells could be human hemangio-colony forming cells. This method could result in solutions comprising hemangio-colony forming cells of between 10,000 to $4 \times 10^6$ hemangio-colony forming cells, or more. The HOXB4 protein used for this method could be any that are suitable for use for the methods for generating and expanding human hemangio-colony forming cells of this invention.

The present invention also provides for methods of inducing immunological tolerance using the human hemangio-colony forming cells generated and expanded or expanded according to the methods of this invention. The tolerizing human hemangio-colony forming cells are chosen to share histocompatibility markers with an allograft, and may be administered to a human recipient before or concurrently with the allograft or cell treatment that regenerates a cellular function needed by the patient. The resulting immune tolerance subsequently decreases the risk of acute or chronic rejection of the allograft or cell treatment.

The large numbers of hemangio-colony forming cells generated by the methods disclosed herein enable tolerance protocols in which toxic pre-conditioning treatments may be eliminated. The donor human hemangio-colony forming cells may be administered to a human recipient prior to implantation of a graft or implantation of an organ, tissue, or cells that are matched with respect to the donor hemangio-colony forming cells. The human hemangio-colony forming cells and graft may be obtained from the same donor. The graft may be derived from differentiated donor human hemangio-colony forming cells. The human hemangio-colony forming cells and graft may alternatively be obtained from different donors wherein the donors are matched. The human hemangio-colony forming cells may be administered to human recipients to induce tolerance in recipients in need thereof.

In certain embodiments, the present invention relates to a method of inducing tolerance in a human recipient to a donor allograft, wherein the method comprises the steps of (a) administering to the recipient an agent that inhibits T cell co-stimulation; (b) introducing into the recipient human hemangio-colony forming cells that are generated and expanded, or expanded, according to the methods described herein; and (c) implanting the allograft into the recipient. The human hemangio-colony forming cells (donor cells) promote acceptance of the allograft by the recipient. In certain embodiments, an agent that inhibits T cell costimulation is an agent that inhibits or blocks the CD40 ligand-CD40 costimulatory interaction. The method may further comprise administering an agent that inhibits the CD28-B7 interaction. The method may or may not comprise thymic irradiation and/or T cell depletion or inactivation. The aforementioned method may also produce mixed chimerism in the absence of hematopoietic space created by whole body irradiation.

The invention also provides for a method of promoting tolerance in a human recipient to a donor allograft, wherein the method comprises the steps of (a) creating thymic space in said recipient; (b) depleting or inactivating donor-reactive T cells in said recipient; (c) introducing donor human hemangio-colony forming cells of said donor or that are matched to said donor into said recipient; and (d) implanting said allograft into said recipient, wherein the donor hemangio-colony forming cells induce tolerance to the allograft. In certain embodiments, the method does not comprise hematopoietic space-creating irradiation. The method may comprise creating thymic space by administering to the recipient at least one treatment selected from among thymic irradiation (which can be fractionated), steroids, corticosteroids, brequinar, or an immune suppressant or drug.

The invention also provides methods for generating cells suitable for use in blood transfusion. For example, the invention provides methods for generating red blood cells that can be used in transfusion. As such, the present invention provides a solution to help alleviate the chronic shortage of blood available for donation.

In certain embodiments, the present invention provides a method for producing differentiated hematopoietic cells from human hemangio-colony forming cells in vitro, said method comprising the steps of: (a) providing human hemangio-colony forming cells; and (b) differentiating said hemangio-colony forming cells into differentiated hematopoietic cells.

In certain embodiments, the present invention provides a method for performing blood transfusions using hematopoietic cells differentiated in vitro from human hemangio-colony forming cells, said method comprising the steps of: (a) providing human hemangio-colony forming cells; (b) differentiating said hemangio-colony forming cells into differentiated hematopoietic cells; and (c) performing blood transfusions with said differentiated hematopoietic cells.

In certain embodiments, said hemangio-colony forming cells are recovered from frozen cultures.

In certain embodiments, the present invention provides a method for performing blood transfusions using hematopoietic cells differentiated in vitro from human hemangio-colony forming cells, said method comprising the steps of: (a) culturing a cell culture comprising human pluripotent stem cells in the presence of at least one growth factor in an amount sufficient to induce the differentiation of said pluripotent stem cells into embryoid bodies; (b) adding at least one growth factor to said culture comprising embryoid bodies, wherein said growth factor is in an amount sufficient to expand human hemangio-colony forming cells in said embryoid bodies culture; (c) differentiating said hemangio-colony forming cells into differentiated hematopoietic cells; and (d) performing blood transfusions with said differentiated hematopoietic cells.

In certain embodiments, said pluripotent stem cells, embryoid bodies and hemangio-colony forming cells are grown in serum-free media throughout step (a) of said method.

In certain embodiments, the pluripotent stem cell is an embryonic stem cell.

In certain embodiments, the present invention provides a method for performing blood transfusions using hematopoietic cells differentiated in vitro from human hemangio-colony forming cells, said method comprising the steps of: (a) culturing a cell culture comprising human pluripotent stem cells in the presence of at least one growth factor in an amount sufficient to induce the differentiation of said pluripotent stem cells into embryoid bodies; (b) adding at least one growth factor to said culture comprising embryoid bodies, wherein said growth factor is in an amount sufficient to expand human hemangio-colony forming cells in said embryoid bodies culture; (c) differentiating said hemangio-colony forming cells into differentiated hematopoietic cells; and (d) performing blood transfusions with said differentiated hematopoietic cells.

In certain embodiments, said stem cells, embryoid bodies and hemangio-colony forming cells are grown in serum-free media throughout steps (a) and (b) of said method.

In certain embodiments of the invention, the pluripotent stem cell is an embryonic stem cell.

In certain embodiments, said hemangio-colony forming cells are recovered from frozen cultures.

In certain embodiments, the present invention provides a method for performing blood transfusions using hematopoietic cells differentiated in vitro from human hemangio-colony forming cells, said method comprising the steps of: (a) culturing a cell culture comprising human pluripotent stem cells in the presence of at least one growth factor in an amount sufficient to induce the differentiation of said pluripotent stem cells into embryoid bodies; (b) adding at least one growth factor to said culture comprising embryoid bodies, wherein said growth factor is in an amount sufficient to expand human hemangio-colony forming cells in said embryoid bodies culture; (c) disaggregating said embryoid bodies into single cells; (d) adding at least one growth factor to said culture comprising said single cells, wherein said growth factor is in an amount sufficient to expand human hemangio-colony forming cells in said culture comprising said single cells; (e) differentiating said hemangio-colony forming cells into differentiated hematopoietic cells; and (f) performing blood transfusions with said differentiated hematopoietic cells.

In certain embodiments, said stem cells, embryoid bodies and hemangio-colony forming cells are grown in serum-free media throughout steps (a)-(d) of said method.

In certain embodiments of the invention, the pluripotent stem cell is an embryonic stem cell.

In certain embodiments, the growth factor is a protein that comprises a homeobox protein, or a functional variant or an active fragment thereof. In certain embodiments, the homeobox protein comprises a HOXB4 protein, or a functional variant or an active variant thereof.

In certain embodiments, the differentiated hematopoietic cells are produced as a single cell type. In certain embodiments, the single cell type is selected from: red blood cells, platelets, or phagocytes. In certain embodiments, the phagocyte is selected from: granulocytes: neutrophils, basophils, eosinophils, lymphocytes or monocytes. In certain embodiments, the red blood cells express hemoglobin F. In certain embodiments, the single cell types are mixed to approximately equal the proportion of differentiated cell types that is found in blood, wherein the proportion of differentiated cell types that is found in blood is 96% red blood cells, 1% platelets, and 3% phagocytes.

In certain embodiments, multiple differentiated hematopoietic cell types are produced in the same step. In certain embodiments, the multiple differentiated hematopoietic cell types are selected from: red blood cells, platelets, or phagocytes. In certain embodiments, the phagocyte is selected from: granulocytes: neutrophils, basophils, eosinophils, lymphocytes or monocytes. In certain embodiments, the red blood cells express hemoglobin F. In certain embodiments, the multiple differentiated hematopoietic cell types are produced in a proportion approximately equal to the proportion of differentiated hematopoietic cell types found in blood, wherein the proportion of differentiated cell types that is found in blood is 96% red blood cells, 1% platelets, and 3% phagocytes.

In certain embodiments, plasma is added to the differentiated hematopoietic cells before transfusion.

In certain embodiments, the hemangio-colony forming cells are matched to a patient to ensure that differentiated hematopoietic cells of the patient's own blood type are produced. In certain embodiments, the hemangio-colony forming cells are negative for antigenic factors A, B, Rh, or any combination thereof. In certain embodiments, the differentiated hematopoietic cells are red blood cells, and wherein a step of differentiating the red blood cells includes erythropoietin (EPO).

The invention also provides a human hemangio-colony forming cell, which cell can differentiate to produce at least hematopoietic or endothelial cell types, wherein the human hemangio-colony forming cell is loosely adherent to other human hemangio-colony forming cells.

In certain embodiments, the invention provides a human hemangio-colony forming cell, which cell can differentiate to produce at least hematopoietic and endothelial cell types, wherein the human hemangio-colony forming cell is loosely adherent to other human hemangio-colony forming cells.

In certain embodiments, the invention provides a human hemangio-colony forming cell, which cell can differentiate to produce at least hematopoietic and endothelial cell types, wherein the human hemangio-colony forming cell is loosely adherent to other human hemangio-colony forming cells, and wherein the human hemangio-colony forming cell does not express CD34 protein.

In certain embodiments, the invention provides a human hemangio-colony forming cell, which cell can differentiate to produce at least hematopoietic and endothelial cell types, wherein the human hemangio-colony forming cell does not express any of the following proteins: CD34, CD31, KDR, and CD133.

In certain embodiments, the invention provides a cell culture comprising human hemangio-colony forming cells, which cells can differentiate to produce at least hematopoietic or endothelial cell types, wherein the hemangio-colony forming cells are loosely adherent to each other.

In certain embodiments, the invention provides a cell culture comprising human hemangio-colony forming cells, which cells can differentiate to produce at least hematopoietic and endothelial cell types, wherein the hemangio-colony forming cells are loosely adherent to each other.

In certain embodiments, the invention provides a cell culture comprising a substantially purified population of human hemangio-colony forming cells, which cells can differentiate to produce at least hematopoietic and endothelial cell types, wherein the hemangio-colony forming cells are loosely adherent to each other, and wherein the hemangio-colony forming cells do not express CD34 protein.

In certain embodiments, the invention provides a cell culture comprising human hemangio-colony forming cells differentiated from pluripotent stem cells, wherein the hemangio-colony forming cells are loosely adherent to each other.

In certain embodiments, the cell culture comprises at least $1 \times 10^6$ human hemangio-colony forming cells. In certain embodiments, the cell culture comprises at least $5 \times 10^6$ human hemangio-colony forming cells.

In certain embodiments, the pluripotent stem cell is an embryonic stem cell line. In certain embodiments, the pluripotent stem cell is selected from an embryo, a blastomere, a blastocyst, or an inner cell mass.

In certain embodiments, the invention provides a pharmaceutical preparation comprising human hemangio-colony forming cells, which cells can differentiate to produce at least hematopoietic or endothelial cell types, wherein the hemangio-colony forming cells are loosely adherent to each other.

In certain embodiments, the invention provides a pharmaceutical preparation comprising human hemangio-colony forming cells, which cells can differentiate to produce at least hematopoietic and endothelial cell types, wherein the hemangio-colony forming cells are loosely adherent to each other.

In certain embodiments, the invention provides a pharmaceutical preparation comprising human hemangio-colony forming cells, which cells can differentiate to produce at least hematopoietic and endothelial cell types, wherein the hemangio-colony forming cells do not express any of the following proteins: CD34, CD31, KDR, and CD133.

In certain embodiments, the pharmaceutical preparation comprises at least $1 \times 10^6$ human hemangio-colony forming cells. In certain embodiments, the preparation comprises at least $5 \times 10^6$ human hemangio-colony forming cells.

In certain embodiments, the pharmaceutical preparation comprising hemangio-colony forming cells are differentiated from pluripotent stem cells. In certain embodiments, the pluripotent stem cell is an embryonic stem cell. In certain embodiments, the pluripotent stem cell is selected from an embryo, a blastomere, a blastocyst, or an inner cell mass.

In certain embodiments, the invention provides a cryopreserved preparation of the hemangio-colony forming cells described in any of the preceding paragraphs.

In certain embodiments, the invention provides a cryopreserved preparation of at least $1 \times 10^6$ human hemangio-colony forming cells, wherein the hemangio-colony forming cells do not express any of the following proteins: CD34, CD31, KDR, and CD133.

In certain embodiments, the cryopreserved preparation comprises at least $5 \times 10^6$ human hemangio-colony forming cells.

In certain embodiments, the cryopreserved preparation comprising human hemangio-colony forming cells do not express CD34 protein. In certain embodiments, the cryopreserved preparation comprising human hemangio-colony forming cells do not express CD34, CD31, CD133, and KDR proteins. In certain embodiments, the cryopreserved preparation comprising human hemangio-colony forming cells express LMO2 and GATA2 proteins.

In certain embodiments, the invention provides a culture comprising a hematopoietic cell differentiated from the hemangio-colony forming cells as described above. In certain embodiments, the invention provides a culture comprising an endothelial cell differentiated from the hemangio-colony forming cells as described above.

In certain embodiments, the invention provides a culture comprising a smooth muscle cell differentiated from the hemangio-colony forming cells as described above.

In certain embodiments, the invention provides a culture comprising a cardiomyocyte differentiated from the hemangio-colony forming cells as described above.

In certain embodiments, the invention provides for the use of the human hemangio-colony forming cells as described above in the manufacture of a medicament to treat a condition in a patient in need thereof.

In certain embodiments, the invention provides the use of the cell culture as described above in the manufacture of a medicament to treat a condition in a patient in need thereof.

In certain embodiments, the invention provides the use of the pharmaceutical preparation as described above in the manufacture of a medicament to treat a condition in a patient in need thereof.

In certain embodiments, the invention provides hemangio-colony forming cells produced by methods as described above.

In certain embodiments, the invention provides human hematopoietic stems cell produced by methods as described above.

In certain embodiments, the invention provides human endothelial cells produced by methods described above.

Other embodiments of the present invention provides methods for making and using a novel cell type related to, but distinct from, hemangio-colony forming cells. The present invention also provides compositions, solutions, and preparations, including cryopreserved preparations, comprising this novel cell type. The present invention further provides in vitro and in vivo therapeutic uses of these cells, as well as methods for producing one or more differentiated cell types that can themselves be used in vitro or in vivo.

In certain embodiments, this invention provides a human non-engrafting hemangio cell, which cell can differentiate to produce at least one or more hematopoietic cell types, wherein the hemangio cell does not have the capacity of engrafting and repopulating the bone marrow in a host.

In certain embodiments, the host is a mammal. In certain embodiments, the mammal is a human.

In certain embodiments, the non-engrafting hemangio cell expresses some but not all of the proteins which characterize human hemangio-colony forming cells that have the capacity of engrafting and repopulating the bone marrow in a host. In certain embodiments, the non-engrafting hemangio cell has one or more characteristics of human hemangio-colony forming cells that have the capacity of engrafting and repopulating the bone marrow in a host. In certain embodiments, the non-engrafting hemangio cell is loosely adherent to other hemangio cells.

In certain embodiments, the non-engrafting hemangio cell does not express one or more proteins selected from CD34, CD31, KDR and CD133. In certain embodiments, the non-engrafting hemangio cell expresses LMO2 and GATA2 proteins.

In certain embodiments, the invention provides a cell culture comprising a substantially purified population of human non-engrafting hemangio cells, which cells can differentiate to produce at least one or more hematopoietic cell types, wherein the hemangio cells do not have the capacity of engrafting and repopulating the bone marrow in a host.

In certain embodiments, the invention provides a cell culture comprising human non-engrafting hemangio cells differentiated from embryo-derived cells, wherein the non-engrafting hemangio cells can differentiate to produce at least one or more hematopoietic cell types, and wherein the hemangio cells do not have the capacity of engrafting and repopulating the bone marrow in a host.

In certain embodiments, the cell culture comprises non-engrafting hemangio cells that express some but not all of the proteins which characterize human hemangio-colony forming cells that have the capacity of engrafting and repopulating the bone marrow in a host. In certain embodiments, the cell culture comprises non-engrafting hemangio cells that have one or more characteristics of human hemangio-colony forming cells that have the capacity of engrafting and repopulating the bone marrow in a host. In certain embodiments, the cell culture comprises non-engrafting hemangio cells that are loosely adherent to other hemangio cells.

In certain embodiments, the cell culture comprises non-engrafting hemangio cells that do not express one or more proteins selected from CD34, CD31, KDR and CD133. In certain embodiments, the cell culture comprises non-engrafting hemangio cells that express LMO2 and GATA2 proteins.

In certain embodiments, the invention provides a cell culture comprising a hematopoietic cell differentiated from the non-engrafting hemangio cells of the invention.

In certain embodiments, the invention provides a solution of human non-engrafting hemangio cells, comprising at least $1 \times 10^6$ human non-engrafting hemangio cells. In certain embodiments, the solution comprises at least $2 \times 10^6$ human non-engrafting hemangio cells. In certain embodiments, the solution comprises at least $3 \times 10^6$ human non-engrafting hemangio cells. In certain embodiments, the solution comprises at least $4 \times 10^6$ human non-engrafting hemangio cells.

In certain embodiments, the solution comprises human non-engrafting hemangio cells that can differentiate to produce at least one or more hematopoietic cell types, and wherein the non-engrafting hemangio cells do not have the capacity of engrafting and repopulating the bone marrow in a host. In certain embodiments, the solution comprises human non-engrafting hemangio cells that express some but not all of the proteins which characterize human hemangio-colony forming cells that have the capacity of engrafting and repopulating the bone marrow in a host. In certain embodiments, the solution comprises human non-engrafting hemangio cells that have one or more characteristics of human hemangio-colony forming cells that have the capacity of engrafting and repopulating the bone marrow in a host. In certain embodiments, the solution comprises human non-engrafting hemangio cells that are loosely adherent to other hemangio cells.

In certain embodiments, the solution comprises non-engrafting hemangio cells that do not express one or more proteins selected from CD34, CD31, KDR and CD133. In certain embodiments, solution comprises non-engrafting hemangio cells that express LMO2 and GATA2 proteins.

In certain embodiments, the solution is injectable to a subject. In certain embodiments, the solution is suitable for freezing. In certain embodiments, the solution is used for the manufacture of a medicament to treat a disease that could be treated by the administration of non-engrafting hemangio cell or hematopoietic cells.

In certain embodiments, the invention provides a pharmaceutical preparation comprising a substantially purified population of human non-engrafting hemangio cells, which cell can differentiate to produce at least one or more hematopoietic cell types, wherein the hemangio cell does not have the capacity of engrafting and repopulating the bone marrow in a host. In certain embodiments, the non-engrafting hemangio cell expresses some but not all of the proteins which characterize human hemangio-colony forming cells that have the capacity of engrafting and repopulating the bone marrow in a host. In certain embodiments, the non-engrafting hemangio cell has one or more of the characteristics of human hemangio-colony forming cells that have the capacity of engrafting and repopulating the bone marrow in a host. In certain embodiments, the hemangio cell is loosely adherent to other hemangio cells. In certain embodiments, the human hemangio cell does not express one or more proteins selected from CD34, CD31, KDR and CD133. In certain embodiments, the human hemangio cell expresses LMO2 and GATA2 proteins. In certain embodiments, the preparation comprises at least $1 \times 10^6$ human non-engrafting hemangio cells. In certain embodiments, the preparation comprises at least $5 \times 10^6$ human non-engrafting hemangio cells.

In certain embodiments, the invention provides a cryopreserved preparation of the human non-engrafting hemangio cells according to the invention. In certain embodiments, the preparation comprises at least $1 \times 10^6$ human non-engrafting hemangio cells. In certain embodiments, the preparation comprises at least $2 \times 10^6$ human non-engrafting hemangio cells. In certain embodiments, the preparation comprises at least $3 \times 10^6$ human non-engrafting hemangio cells. In certain embodiments, the preparation comprises at least $4 \times 10^6$ human non-engrafting hemangio cells. In certain embodiments, the preparation comprises at least $5 \times 10^6$ human non-engrafting hemangio cells.

In certain embodiments, the invention provides a method for generating and expanding human non-engrafting hemangio cell in vitro, said method comprising the steps of: (a) culturing a cell culture comprising human embryo-derived cells in serum-free media in the presence of at least one growth factor in an amount sufficient to induce the differentiation of said embryo-derived cells into embryoid bodies; and (b) adding at least one growth factor to the culture comprising embryoid bodies and continuing to culture the culture in serum-free media, wherein the growth factor is in an amount sufficient to expand human non-engrafting hemangio cells in the embryoid bodies culture, wherein the embryoid bodies are cultured for 10-13 days, and wherein the embryo-derived cells, embryoid bodies and non-engrafting hemangio cells are grown in serum-free media throughout steps (a) and (b) of said method.

In certain embodiments, the invention provides a method for generating and expanding human non-engrafting hemangio cell in vitro, the method comprising the steps of: (a) culturing a cell culture comprising human embryo-derived cells in serum-free media in the presence of at least one growth factor in an amount sufficient to induce the differentiation of said embryo-derived cells into embryoid bodies; (b) adding at least one growth factor to the culture comprising embryoid bodies and continuing to culture the culture in serum-free media, wherein the growth factor is in an amount sufficient to expand human non-engrafting hemangio cells in the embryoid bodies culture; (c) disaggregating the embryoid bodies into single cells; and (d) adding at least one growth factor to the culture comprising the single cells and continuing to culture the culture in serum-free media, wherein the growth factor is in an amount sufficient to expand human non-engrafting hemangio cells in the culture comprising the single cells, wherein the culture of single cells are cultured for 10-13 days, and wherein the embryo-derived cells, embryoid bodies and non-engrafting hemangio cells are grown in serum-free media throughout steps (a)-(d) of said method.

In certain embodiments, the embryo-derived cell is an embryonic stem cell.

In certain embodiments, the growth factor is a protein that comprises a homeobox protein or a functional variant or an active variant thereof. In certain embodiments, the homeobox protein comprises a HOXB4 protein, or a functional variant or an active variant thereof. In certain embodiments, the growth factor is selected from the group consisting of vascular endothelial growth factor (VEGF), bone morphogenic proteins (BMP), stem cell factor (SCF), Flt-3L (FL) thrombopoietin (TPO) and erythropoietin (EPO).

In certain embodiments, the vascular endothelial growth factor (VEGF) or bone morphogenic protein (BMP), or both, are added to step (a) within 0-48 hours of cell culture. In certain embodiments, the stem cell factor (SCF), Flt-3L (FL) or thrombopoietin (TPO), or any combination thereof, are added to said culture within 48-72 hours from the start of step (a). In certain embodiments, the growth factor is added to step (b) within 48-72 hours from the start of step (a).

In certain embodiments, the method further comprises adding erythropoietin (EPO) to step (b). In certain embodiments, the method further comprises adding erythropoietin (EPO) to steps (b) and (d).

In certain embodiments, the method further comprises the step of purifying the human non-engrafting hemangio cells from the culture. In certain embodiments, the method further comprises the step of isolating the human non-engrafting hemangio cells from the culture.

In certain embodiments, the growth factor is a fusion protein that comprises HOXB4 and a protein transduction domain (PTD). In certain embodiments, the PTD and HOXB4 are conjugated via a linker. In certain embodiments, the protein transduction domain (PTD) is TAT protein, a functional variant or an active fragment thereof. In certain embodiments, the HOXB4 is mammalian HOXB4. In certain embodiments, the mammalian HOXB4 is mouse or human HOXB4. In certain embodiments, the HOXB4 comprises a full-length protein.

In certain embodiments, the method further comprises the step of culturing the non-engrafting hemangio cells under conditions suitable to induce the differentiation of said non-engrafting hemangio cells into human hematopoietic stem cells.

In certain embodiments, the culture comprises at least $1\times10^6$ human non-engrafting hemangio cells. In certain embodiments, the culture comprises at least $2\times10^6$ human non-engrafting hemangio cells. In certain embodiments, the culture comprises at least $3\times10^6$ human non-engrafting hemangio cells. In certain embodiments, the culture comprises at least $4\times10^6$ human non-engrafting hemangio cells.

In certain embodiments, the invention provides a method for producing human hematopoietic stem cells in vitro, comprising the steps of: (a) supplying human non-engrafting hemangio cells made by the methods of this invention; and (b) growing the human non-engrafting hemangio cells under conditions suitable to induce the differentiation of the human non-engrafting hemangio cells into human hematopoietic stem cells.

In certain embodiments, the invention provides a method for administering human non-engrafting hemangio cells to a patient in need thereof, comprising the steps of: (a) selecting the patient in need thereof; (b) supplying human non-engrafting hemangio cells made by the methods of this invention; (c) administering some or all of the human non-engrafting hemangio cells to the patient.

In certain embodiments, the invention provides a method for administering human non-engrafting hemangio cells to a patient in need thereof, comprising the steps of: (a) selecting the patient in need thereof; (b) supplying human non-engrafting hemangio cells in an amount of at least 10,000 cells; (c) administering some or all of the human hemangio-colony forming cells to said patient. In certain embodiments, the human non-engrafting hemangio cells are in an amount between 10,000 to 4 million cells.

In certain embodiments, the invention provides a method for administering human hematopoietic stem cells to a patient in need thereof, comprising the steps of: (a) selecting the patient in need thereof; (b) supplying human non-engrafting hemangio cells made by the methods of this invention; (c) differentiating the human non-engrafting hemangio cells into human hematopoietic stem cells; and (d) administering some or all of the human hematopoietic stem cells to said patient.

In certain embodiments, the invention provides a method for administering human hematopoietic stem cells to a patient in need thereof, comprising the steps of: (a) selecting the patient in need thereof; (b) supplying human non-engrafting hemangio cells in an amount of at least 10,000 cells; (c) differentiating the human non-engrafting hemangio cells into human hematopoietic stem cells; and (d) administering some or all of the human hematopoietic stem cells to said patient. In certain embodiments, the human non-engrafting hemangio cells are in an amount between 10,000 to 4 million cells.

In certain embodiments, the invention provides a method of treating a hematopoietic stem cell disorder in a patient in need thereof, comprising the steps of: (a) selecting the patient in need thereof; (b) supplying human non-engrafting hemangio cells made by the methods of this invention; (c) differentiating the human non-engrafting hemangio cells into human hematopoietic stem cells; and (d) administering some or all of the human hematopoietic stem cells to the patient.

In certain embodiments, the invention provides a method of treating a hematopoietic stem cell disorder in a patient in need thereof, comprising the steps of: (a) selecting the patient in need thereof; (b) supplying human non-engrafting hemangio cells in an amount of at least 10,000 cells; (c) differentiating the human non-engrafting hemangio cells into human hematopoietic stem cells; and (d) administering some or all of the human hematopoietic stem cells to said patient. In certain embodiments, the human non-engrafting hemangio cells are in an amount between 10,000 to 4 million cells.

In certain embodiments, the invention provides a method for producing differentiated hematopoietic cells from non-engrafting hemangio cells in vitro, the method comprising the steps of: (a) providing human non-engrafting hemangio cells; and (b) differentiating the non-engrafting hemangio cells into differentiated hematopoietic cells.

In certain embodiments, the invention provides a method for performing blood transfusions using hematopoietic cells differentiated in vitro from human non-engrafting hemangio cells, the method comprising the steps of: (a) providing human non-engrafting hemangio cells; (b) differentiating the non-engrafting hemangio cells into differentiated hematopoietic cells; and (c) performing blood transfusions with the differentiated hematopoietic cells.

In certain embodiments, the invention provides a method for producing differentiated hematopoietic cells from non-engrafting hemangio cells in vitro, said method comprising the steps of: (a) providing human non-engrafting hemangio cells made by the methods of this invention; and (b) differentiating the non-engrafting hemangio cells into differentiated hematopoietic cells.

In certain embodiments, the invention provides a method for performing blood transfusions using hematopoietic cells differentiated in vitro from human non-engrafting hemangio cells, said method comprising the steps of: (a) providing human non-engrafting hemangio cells made by the methods of this invention; (b) differentiating the non-engrafting hemangio cells into differentiated hematopoietic cells; and (c) performing blood transfusions with said differentiated hematopoietic cells.

In certain embodiments, the invention provides non-engrafting hemangio cells produced by methods as described above.

In certain embodiments, the invention provides human hematopoietic stems cell produced by methods as described above.

In certain embodiments, the invention provides differentiated human hematopoietic stems cell produced by methods as described above.

In certain embodiments, the invention provides human endothelial cells produced by methods described above.

Other illustrative methods, compositions, preparations, and features of the invention are described in U.S. application Ser. No. 11/787,262, filed Apr. 13, 2007, and entitled "Hemangio-Colony Forming Cells." The teachings of this application are hereby incorporated by reference in its entirety. It should be noted that Applicants consider all operable combinations of the disclosed illustrative embodiments to be patentable subject matter including combinations of the subject matter disclosed in U.S. application Ser. No. 11/787, 262.

In certain embodiments of any of the foregoing, the non-engrafting hemangio cells provided herein have one or more of the properties of the cells described in U.S. application Ser. No. 11/787,262. In certain embodiments of any of the foregoing, the non-engrafting hemangio cells provided herein are formulated as compositions, preparations, cryopreserved preparations, or purified or mixed solutions as described in U.S. application Ser. No. 11/787,262. In certain embodiments of any of the foregoing, the non-engrafting hemangio cells provided herein are used therapeutically or in blood banking as described in U.S. application Ser. No. 11/787,262. In certain embodiments of any of the foregoing, the non-engrafting hemangio cells provided herein are used to generate partially and/or terminally differentiated cell types for in vitro or in vivo use as described in U.S. application Ser. No. 11/787,262. In certain embodiments of any of the foregoing, the non-engrafting hemangio cells provided herein are derived from ES cells, ED cells, etc. using any of the methodologies described herein and in U.S. application Ser. No. 11/787,262.

In certain embodiments of any of the foregoing, the non-engrafting hemangio cells are used to produce differentiated hematopoietic cells, for example, differentiated red blood cells.

In certain embodiments of any of the foregoing, hemangio-colony forming cells and/or non-engrafting hemangio cells are generated from embryonic material, such as embryonic stem cells or embryo-derived cells. In certain embodiments, the cells are generated from pluripotent cells. Although embryonic stem cells are exemplary of pluripotent cells, the invention also contemplates that other pluripotent cell types, including non-embryonic pluripotent cell types, can be used to generate hemangio-colony forming cells and/or non-engrafting hemangio cells. Examples of other pluripotent cells include, but are not limited to, induced pluripotent stem cells (iPS).

In certain embodiments wherein iPS cells are used, said iPS cells are passaged with trypsin, said iPS cells are maintained with mouse embryonic fibroblasts (MEFs) or are maintained feeder-free, and/or Y-27632 is added to serum-free embryoid body media and/or differentiation media.

In certain embodiments, the invention provides hemangioblasts, hemangio colony forming cells, non-engrafting hemangio cells, hematopoietic cells and endothelial cells produced from iPS cells as described herein.

The invention contemplates combinations of any of the foregoing aspects and embodiments of the invention.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 7 depicts a wild-type nucleic acid sequence of HOXB4 protein in accordance with an embodiment of the present invention.

FIG. 8 depicts a wild-type nucleic acid sequence of HOXB4 protein in accordance with an embodiment of the present invention.

FIG. 9 depicts an amino acid sequence of HOXB4 in accordance with an embodiment of the present invention.

FIG. 10 depicts an amino acid sequence of HOXB4 in accordance with an embodiment of the present invention.

FIG. 11 depicts iPSCs (IMR90-1) grown under feeder-free conditions retain pluripotency markers in accordance with an embodiment of the present invention. After 4-5 passages under feeder-free conditions iPS(IMR90)-1 cells were stained for expression of pluripotency markers. a, bright field; b, Nanog; c, Oct-4; d, SSEA-4; and e, TRA-1-60. Magnification: originally ×200.

FIG. 12 depicts the effect of ROCK inhibitor on iPSC hemangioblastic differentiation in accordance with an embodiment of the present invention. EBs generated from iPS(IMR90)-1 cells 24 hr after plating without (a, originally 100×) and with (b, originally 100×) ROCK inhibitor; Blast colonies derived from iPS(IMR90)-1 cells without ROCK inhibitor (c, originally 200×), with ROCK inhibitor (d, originally 200×), and with ROCK inhibitor plus Art pathway inhibitor (e, originally 200×) during EB formation; f-j; Hematopoietic and endothelial cell differentiation of iPSC-derived hemangioblasts: f (originally 200×); CFU-E; g (originally 100×), CFU-M; h (originally 40×), CFU-G; i (originally 400×), uptake of Ac-LDL (red) by endothelial cells stained with VE-Cadherin (green); j (originally 40×), tube-like network after plating endothelial cells on Matrigel.

DESCRIPTION OF THE INVENTION

Figure 1A:
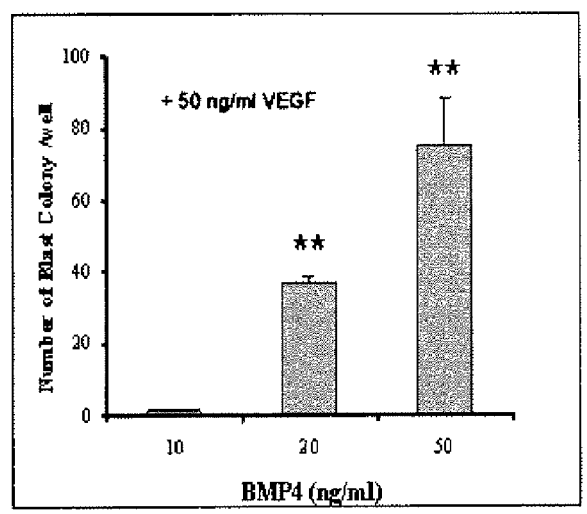
FIG. 1 depicts the effects of BMPs and VEGF$_{165}$ on the development of blast colonies in accordance with an embodiment of the present invention. A. Different doses of BMP-4 were added in EB medium containing 50 ng/ml of VEGF$_{165}$, and a dose dependent development of blast colonies was observed for BMP-4. B. EB medium containing 50 ng/ml of BMP-4 and VEGF$_{165}$ were supplemented with different doses (0, 10 and 20 ng/ml) of BMP-2 and BMP-7. BMP-2 and BMP-7 failed in promoting blast colony development. C. Different doses of VEGF$_{165}$ were added in EB medium containing 50 ng/ml of BMP-4. The development of blast colonies is VEGF$_{165}$ dose dependent. **$P<0.01$, n=3. $1\times10^5$ cells from day 3.5 EBs were plated per well.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* $3^{rd}$ ed., J. Wiley & Sons (New York, N.Y. 2001); March, *Advanced Organic Chemistry Reactions, Mechanisms and Structure* $5^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Throughout this specification, the word "comprise" or variations such as "comprises" or "comprising" will be understood to imply the inclusion of a stated integer or groups of integers but not the exclusion of any other integer or group of integers.

The term "embryonic stem cells" (ES cells) refers to embryo-derived cells and is used herein as it is used in the art. This term includes cells derived from the inner cell mass of human blastocysts or morulae, including those that have been serially passaged as cell lines. When used to refer to cells from humans, the term human embryonic stem cell (hES) cell is used. The ES cells may be derived from fertilization of an egg cell with sperm, as well as using DNA, nuclear transfer, parthenogenesis, or by means to generate ES cells with homozygosity in the HLA region. ES cells are also cells derived from a zygote, blastomeres, or blastocyst-staged mammalian embryo produced by the fusion of a sperm and egg cell, nuclear transfer, parthenogenesis, androgenesis, or the reprogramming of chromatin and subsequent incorporation of the reprogrammed chromatin into a plasma membrane to produce a cell. Embryonic stem cells, regardless of their source or the particular method use to produce them, can be identified based on (i) the ability to differentiate into cells of all three germ layers, (ii) expression of at least Oct-4 and alkaline phosphatase, and (iii) ability to produce teratomas when transplanted into immunodeficient animals.

As used herein, the term "pluripotent stem cells" includes embryonic stem cells, embryo-derived stem cells, and induced pluripotent stem cells, regardless of the method by which the pluripotent stem cells are derived. Pluripotent stem cells are defined functionally as stem cells that are: (a) capable of inducing teratomas when transplanted in immunodeficient (SCID) mice; (b) capable of differentiating to cell types of all three germ layers (e.g., can differentiate to ectodermal, mesodermal, and endodermal cell types); and (c) express one or more markers of embryonic stem cells (e.g., express Oct 4, alkaline phosphatase, SSEA-3 surface antigen, SSEA-4 surface antigen, nanog, TRA-1-60, TRA-1-81, SOX2, REX1, etc). Exemplary pluripotent stem cells can be generated using, for example, methods known in the art. Exemplary pluripotent stem cells include embryonic stem cells derived from the ICM of blastocyst stage embryos, as well as embryonic stem cells derived from one or more blastomeres of a cleavage stage or morula stage embryo (optionally without destroying the remainder of the embryo). Such embryonic stem cells can be generated from embryonic material produced by fertilization or by asexual means, including somatic cell nuclear transfer (SCNT), parthenogenesis, and androgenesis. Further exemplary pluripotent stem cells include induced pluripotent stem cells (iPS cells) generated by reprogramming a somatic cell by expressing a combination of factors (herein referred to as reprogramming factors). iPS cells can be generated using fetal, postnatal, newborn, juvenile, or adult somatic cells. In certain embodiments, factors that can be used to reprogram somatic cells to pluripotent stem cells include, for example, a combination of Oct4 (sometimes referred to as Oct 3/4), Sox2, c-Myc, and Klf4. In other embodiments, factors that can be used to reprogram somatic cells to pluripotent stem cells include, for example, a combination of Oct 4, Sox2, Nanog, and Lin28. In other embodiments, somatic cells are reprogrammed by expressing at least 2 reprogramming factors, at least three reprogramming factors, or four reprogramming factors. In other embodiments, additional reprogramming factors are identified and used alone or in combination with one or more known reprogramming factors to reprogram a somatic cell to a pluripotent stem cell. Induced pluripotent stem cells are defined functionally and include cells that are reprogrammed using any of a variety of methods (integrative vectors, non-integrative vectors, chemical means, etc).

The pluripotent stem cells can be from any species. Embryonic stem cells have been successfully derived in, for example, mice, multiple species of non-human primates, and humans, and embryonic stem-like cells have been generated from numerous additional species. Thus, one of skill in the art can generate embryonic stem cells and embryo-derived stem cells from any species, including but not limited to, human, non-human primates, rodents (mice, rats), ungulates (cows, sheep, etc), dogs (domestic and wild dogs), cats (domestic and wild cats such as lions, tigers, cheetahs), rabbits, hamsters, gerbils, squirrel, guinea pig, goats, elephants, panda (including giant panda), pigs, raccoon, horse, zebra, marine mammals (dolphin, whales, etc.) and the like. In certain embodiments, the species is an endangered species. In certain embodiments, the species is a currently extinct species.

Similarly, iPS cells can be from any species. iPS cells have been successfully generated using mouse and human cells. iPS cells have been successfully generated using embryonic, fetal, newborn, and adult tissue. Accordingly, one can readily generate iPS cells using a donor cell from any species. Thus, one can generate iPS cells from any species, including but not limited to, human, non-human primates, rodents (mice, rats), ungulates (cows, sheep, etc), dogs (domestic and wild dogs), cats (domestic and wild cats such as lions, tigers, cheetahs), rabbits, hamsters, goats, elephants, panda (including giant panda), pigs, raccoon, horse, zebra, marine mammals (dolphin, whales, etc.) and the like. In certain embodiments, the species is an endangered species. In certain embodiments, the species is a currently extinct species.

Induced pluripotent stem cells can be generated using, as a starting point, virtually any somatic cell of any developmental stage. For example, the cell can be from an embryo, fetus, neonate, juvenile, or adult donor. Exemplary somatic cells that can be used include fibroblasts, such as dermal fibroblasts obtained by a skin sample or biopsy, synoviocytes from synovial tissue, foreskin cells, cheek cells, or lung fibroblasts. Although skin and cheek provide a readily available and easily attainable source of appropriate cells, virtually any cell can be used. In certain embodiments, the somatic cell is not a fibroblast.

Note that the pluripotent stem cells can be, for example, ES cells or induced pluripotent stem cells. Induced pluripotent stem cells can be produced by expressing a combination of reprogramming factors in a somatic cell. In certain embodiments, at least two reprogramming factors are expressed in a somatic cell to successfully reprogram the somatic cell. In other embodiments, at least three reprogramming factors are expressed in a somatic cell to successfully reprogram the somatic cell. In other embodiments, at least four reprogramming factors are expressed in a somatic cell to successfully reprogram the somatic cell.

The term "protein transduction domain" ("PTD") refers to any amino acid sequence that translocates across a cell membrane into cells or confers or increases the rate of, for example, another molecule (such as, for example, a protein domain) to which the PTD is attached, to translocate across a cell membrane into cells. The protein transduction domain may be a domain or sequence that occurs naturally as part of a larger protein (e.g., a PTD of a viral protein such as HIV TAT) or may be a synthetic or artificial amino acid sequence.

The terms "hemangioblast" and "hemangio-colony forming cells" will be used interchangeably throughout this application. The cells have numerous structural and functional characteristics. Amongst the characteristics of these cells is the ability to engraft into the bone marrow when administered to a host. These cells can be described based on numerous structural and functional properties including, but not limited to, expression (RNA or protein) or lack of expression (RNA or protein) of one or more markers. Hemangio-colony forming cells are capable of differentiating to give rise to at least hematopoietic cell types or endothelial cell types. Hemangio-colony forming cells are preferably bi-potential and capable of differentiating to give rise to at least hematopoietic cell types and endothelial cell types. As such, hemangio-colony forming cells of the present invention are at least uni-potential, and preferably bi-potential. Additionally however, hemangio-colony forming cells may have a greater degree of developmental potential and can, in certain embodiments, differentiate to give rise to cell types of other lineages. In certain embodiments, the hemangio-colony forming cells are capable of differentiating to give rise to other mesodermal derivatives such as cardiac cells (for example, cardiomyocytes) and/or smooth muscle cells.

The term "non-engrafting hemangio cells" is used throughout this application to refer to a novel population of cells that share some of the characteristics of hemangio-colony forming cells. However, the non-engrafting hemangio cells are distinguishable in that they do not engraft into the bone marrow when administered to an immunodeficient host. Despite this difference, non-engrafting hemangio cells may share one or more than one (2, 3, 4, 5, 6, 7, 8, 9, 10) of the functional or structural characteristics/properties of hemangio-colony forming cells. For example, in certain embodiments, the non-engrafting hemangio cells are loosely adherent to each other. In other embodiments, the non-engrafting hemangio cells do not express one or more that one (2, 3, 4) of the following proteins: CD34, KDR, CD133, CD31. Without being bound by theory, non-engrafting hemangio cells may provide a distinct stem cell population that is somewhat more committed than hemangio-colony forming cells, and yet still capable of producing a range of hematopoietic cell types.

Hemangio-Colony Forming Cells

This invention provides a method for generating and expanding human hemangio-colony forming cells from human pluripotent stem cells, preparations and compositions comprising human hemangio-colony forming cells, methods of producing various cell types partially or terminally differentiated from hemangio-colony forming cells, methods of using hemangio-colony forming cells therapeutically, and methods of therapeutically using various cell types partially or terminally differentiated from hemangio-colony forming cells.

Here, the inventors report a simpler and more efficient method for robust generation of hemangioblastic progenitors. In addition to eliminating several expensive factors that are unnecessary, it is demonstrated that bone morphogenetic protein-4 (BMP-4) and vascular endothelial growth factor (VEGF) are necessary and sufficient to induce hemangioblastic commitment and development from pluripotent stem cells during early stages of differentiation. BMP-4 and VEGF significantly up-regulate T-brachyury, KDR, CD31 and LMO2 gene expression, while dramatically down-regulating Oct-4 expression. The addition of basic fibroblast growth factor (bFGF) during growth and expansion was found to further enhance BC development, consistently generating approximately $1\times10^8$ BCs from one six-well plate of hESCs.

This invention also provides a method for expanding mammalian hemangio-colony forming cells obtained from any source, including ES cells, blastocysts or blastomeres, cord blood from placenta or umbilical tissue, peripheral blood, bone marrow, or other tissue or by any other means known in the art. Human hemangio-colony forming cells can also be generated from human pluripotent stem cells. Human pluripotent stem cells may be a substantially homogeneous population of cells, a heterogeneous population of cells, or all or a portion of an embryonic tissue. As an example of pluripotent stem cells that can be used in the methods of the present invention, human hemangio-colony forming cells can be generated from human embryonic stem cells. Such embryonic stem cells include embryonic stem cells derived from or using, for example, blastocysts, plated ICMs, one or more blastomeres, or other portions of a pre-implantation-stage embryo or embryo-like structure, regardless of whether produced by fertilization, somatic cell nuclear transfer (SCNT), parthenogenesis, androgenesis, or other sexual or asexual means.

In certain embodiments, hemangioblasts can be further differentiated to hematopoietic cells including, but not limited to, platelets and red blood cells. Such cells may be used in transfusions. The ability to generate large numbers of cells for transfusion will alleviate the chronic shortage of blood experienced in blood banks and hospitals across the country. In certain embodiments, the methods of the invention allow for the production of universal cells for transfusion. Specifically, red blood cells that are type O and Rh— can be readily generated and will serve as a universal blood source for transfusion.

The methods of this invention allow for the in vitro expansion of hemangioblasts to large quantities useful for a variety of commercial and clinical applications. Expansion of hemangioblasts in vitro refers to the proliferation of hemangio blasts. While the methods of the invention enable the expansion of human hemangioblast cells to reach commercially useful quantities, the present invention also relates to large numbers of hemangioblast cells and to cell preparations comprising large numbers of human hemangioblast cells (for example, at least 10,000, 100,000, or 500,000 cells). In certain embodiments, the cell preparations comprise at least $1\times10^6$ cells. In other embodiments, the cell preparations comprise at least $2\times10^6$ human hemangioblast cells and in further embodiments at least $3\times10^6$ human hemangioblast cells. In still other embodiments, the cell preparations comprise at least 4×10⁶ human hemangioblast cells.

The present invention relates to a solution, a preparation, and a composition comprising between 10,000 and 4 million or more mammalian (such as human) hemangioblast cells. The number of hemangioblast cells in such a solution, a preparation, and a composition may be any number between the range of 10,000 to 4 million, or more. This number could be, for example, 20,000, 50,000, 100,000, 500,000, 1 million, etc.

Similarly, the invention relates to preparations of human hemangioblast progeny cells (e.g., human hematopoietic cells including human hematopoietic stem cells, and endothelial cells). The invention further relates to methods of producing, storing, and distributing hemangioblast cells and/or hemangioblast lineage cells.

The invention also provides methods and solutions suitable for transfusion into human or animal patients. In particular embodiments, the invention provides methods of making red blood cells and/or platelets, and/or other hematopoietic cell types for transfusion. In certain embodiments, the invention is suitable for use in blood banks and hospitals to provide blood for transfusion following trauma, or in the treatment of a blood-related disease or disorder. In certain embodiments, the invention provides red blood cells that are universal donor cells. In certain embodiments, the red blood cells are functional and express hemoglobin F prior to transfusion.

The invention also provides for human hemangio-colony forming cells, cell cultures comprising a substantially purified population of human hemangio-colony forming cells, pharmaceutical preparations comprising human hemangio-colony forming cells and cryopreserved preparations of the hemangio-colony forming cells. In certain embodiments, the invention provides for the use of the human hemangio-colony forming cells in the manufacture of a medicament to treat a condition in a patient in need thereof. Alternatively, the invention provides the use of the cell cultures in the manufacture of a medicament to treat a condition in a patient in need thereof. The invention also provides the use of the pharmaceutical preparations in the manufacture of a medicament to treat a condition in a patient in need thereof.

The hemangio-colony forming cells can be identified and characterized based on their structural properties. Specifically, and in certain embodiments, these cells are unique in that they are only loosely adherent to each other (loosely adherent to other hemangio-colony forming cells). Because these cells are only loosely adherent to each other, cultures or colonies of hemangio-colony forming cells can be dissociated to single cells using only mechanical dissociation techniques and without the need for enzymatic dissociation techniques. The cells are sufficiently loosely adherent to each other that mechanical dissociation alone, rather than enzymatic dissociation or a combination of mechanical and enzymatic dissociation, is sufficient to disaggregate the cultures or colonies without substantially impairing the viability of the cells. In other words, mechanical dissociation does not require so much force as to cause substantial cell injury or death when compared to that observed subsequent to enzymatic dissociation of cell aggregates.

Furthermore, hemangio-colony forming cells can be identified or characterized based on the expression or lack of expression (as assessed at the level of the gene or the level of the protein) of one or more markers. For example, in certain embodiments, hemangio-colony forming cells can be identified or characterized based on lack of expression of one or more (e.g., the cells can be characterized based on lack of expression of at least one, at least two, at least three or at least four of the following markers) of the following cell surface markers: CD34, KDR, CD133, or CD31. Additionally or alternatively, hemangio-colony forming cells can be identified or characterized based on expression of GATA2 and/or LMO2. Additionally or alternatively, hemangio-colony forming cells can be identified or characterized based on expression or lack of expression markers.

Hemangio-colony forming cells of the present invention can be identified or characterized based on one or any combination of these structural or functional characteristics. Note that although these cells can be derived from any of a number of sources, for example, embryonic tissue, prenatal tissue, or perinatal tissue, the term "hemangio-colony forming cells" applies to cells, regardless of source, that are capable of differentiating to give rise to at least hematopoietic cell types and/or endothelial cell types and that have one or more of the foregoing structural or functional properties.

In certain embodiments, marker(s) for the progenitor of BCs can be used to select BCs after initial culturing.

In certain embodiments, hemangio-colonies are produced from pluripotent cells without forming embryoid bodies.

In Vitro Differentiation of Pluripotent Stem Cells to Obtain Embryoid Bodies and Hemangioblasts The present invention provides a method for generating and expanding human hemangioblasts derived from human pluripotent stem cells, or from human blastocysts or blastomeres. The hemangioblasts so produced may be purified and/or isolated.

Human hemangio-colony forming cells can also be generated from human pluripotent stem cells. Human pluripotent stem cells may be a substantially homogeneous population of cells, a heterogeneous population of cells, or all or a portion of an embryonic tissue. As an example of pluripotent stem cells that can be used in the methods of the present invention, human hemangio-colony forming cells can be generated from human embryonic stem cells. Such embryonic stem cells include embryonic stem cells derived from or using, for example, blastocysts, plated ICMs, one or more blastomeres, or other portions of a pre-implantation-stage embryo or embryo-like structure, regardless of whether produced by fertilization, somatic cell nuclear transfer (SCNT), parthenogenesis, androgenesis, or other sexual or asexual means.

Additionally or alternatively, hemangio-colony forming cells can be generated from other pluripotent stem cells. For example, hemangio-colony forming cells can be generated (without necessarily going through a step of embryonic stem cell derivation) from or using plated embryos, ICMs, blastocysts, trophoblast/trophectoderm cells, one or more blastomeres, trophoblast stem cells, embryonic germ cells, or other portions of a pre-implantation-stage embryo or embryo-like structure, regardless of whether produced by fertilization, somatic cell nuclear transfer (SCNT), parthenogenesis, androgenesis, or other sexual or asexual means. Similarly, hemangio-colony forming cells can be generated using cells or cell lines partially differentiated from pluripotent stem cells. For example, if a human embryonic stem cell line is used to produce cells that are more developmentally primitive than hemangio-colony forming cells, in terms of development potential and plasticity, such pluripotent stem cells could then be used to generate hemangio-colony forming cells.

Additionally or alternatively, hemangio-colony forming cells can be generated from other pre-natal or peri-natal sources including, without limitation, umbilical cord, umbilical cord blood, amniotic fluid, amniotic stem cells, and placenta.

It is noted that when hemangio-colony forming cells are generated from human embryonic tissue a step of embryoid body formation may be needed. However, given that embryoid body formation serves, at least in part, to help recapitulate the three dimensional interaction of the germ layers that occurs during early development, such a step is not necessarily required when the pluripotent stem cells already have a structure or organization that serves substantially the same purpose as embryoid body formation. By way of example, when hemangio-colony forming cells are generated from plated blastocysts, a level of three dimensional organization already exists amongst the cells in the blastocyst. As such, a step of embryoid body formation is not necessarily required to provide intercellular signals, inductive cues, or three dimensional architecture.

The methods and uses of the present invention can be used to generate hemangio-colony forming cells from pluripotent stem cells or embryo-derived cells. In certain embodiments, the embryo-derived cells are embryonic stem cells. In certain other embodiments, the embryo-derived cells are plated embryos, ICMs, blastocysts, trophoblast/trophectoderm cells, one or more blastomeres, trophoblast stem cells, or other portions of an early pre-implantation embryo. For any of the foregoing, the embryo-derived cells may be from embryos produced by fertilization, somatic cell nuclear transfer (SCNT), parthenogenesis, androgenesis, or other sexual or asexual means.

Throughout this application, when a method is described by referring specifically to generating hemangio-colony forming cells from embryonic stem cells, the invention similarly contemplates generating hemangio-colony forming cells from or using other pluripotent stem cells or embryonic-derived cells, and using the generated cells for any of the same therapeutic applications.

In certain aspects of the invention, the human embryonic stem cells may be the starting material of this method. The embryonic stem cells may be cultured in any way known in the art, such as in the presence or absence of feeder cells.

Embryonic stem cells may form embryoid bodies ("EBs") in suspension in medium containing serum (Wang et al. 2005 J Exp Med (201):1603-1614; Wang et al. 2004 Immunity (21): 31-41; Chadwick et al., 2003 Blood (102): 906-915). The addition of serum, however, presents certain challenges, including variability in experiments, cost, potential for infectious agents, and limited supply. Further, for clinical and certain commercial applications, use of serum necessitates additional U.S. and international regulatory compliance issues that govern biological products.

The present invention provides methods of generating and expanding human hemangioblasts from pluripotent stem cells in which no serum is used. The serum-free conditions are more conducive to scale-up production under good manufacturing process (GMP) guidelines than are conditions which require serum. Furthermore, serum-free conditions extend the half-life of certain factors added to the medium (for example, the half-life of proteins including growth factors, cytokines, and HOXB4 in media is increased when no serum is present). In certain embodiments, the media is supplemented with BMP4 and VEGF. In certain embodiments, serum-free media is used throughout the method of this invention for generating and expanding human hemangioblasts.

In the first step of this method for generating and expanding human hemangioblast cells, human stem cells are grown in serum-free media and are induced to differentiate into embryoid bodies. To induce embryoid body formation, embryonic stem cells may be pelleted and resuspended in serum-free medium (e.g., in Stemline I or II media (Sigma™)) supplemented with one or more morphogenic factors and cytokines and then plated on low attachment (e.g., ultra-low attachment) culture dishes. Morphogenic factors and cytokines may include, but are not limited to, bone morphogenic proteins (e.g., BMP2, BMP-4, BMP-7, but not BMP-3) and VEGF, SCF and FL. Bone morphogenic proteins and VEGF may be used alone or in combination with other factors. The morphogenic factors and cytokines may be added to the media from 0-48 hours of cell culture. Following incubation under these conditions, incubation in the presence of early hematopoietic expansion cytokines, including, but not limited to, thrombopoietin (TPO), Flt-3 ligand, and stem cell factor (SCF), allows the plated ES cells to form EBs. In addition to TPO, Flt-3 ligand, and SCF, VEGF, BMP-4, and HoxB4 may also be added to the media. In one embodiment, human ES cells are first grown in the presence of BMP-4 and $VEGF_{165}$ (e.g., 25-100 ng/ml), followed by growing in the presence of BMP-4, $VEGF_{165}$, SCF, TPO, and FLT3 ligand (e.g., 10-50 ng/ml) and HoxB4 (e.g., 1.5-5 µg/ml of a triple protein transduction domain-HoxB4 fusion protein as disclosed herein). The additional factors may be added 48-72 hours after plating.

In this method of the present invention, human hemangioblast cells are isolated from early embryoid bodies ("EBs"). Isolating hemangioblast cells from early EBs supports the expansion of the cells in vitro. For human cells, hemangioblast cells may be obtained from EBs grown for less than 10 days. In certain embodiments of the present invention, hemangioblast cells arise in human EBs grown for 2-6 days. According to one embodiment, hemangioblast cells are identified and may be isolated from human EBs grown for 4-6 days. In other embodiments, human EBs are grown for 2-5 days before hemangioblast cells are isolated. In certain embodiments, human EBs are grown for 3-4.5 days before hemangioblast cells are isolated.

In certain embodiments, early EBs are washed and dissociated (e.g., by Trypsin/EDTA or collagenase B). A select number of cells (e.g., $2-5 \times 10^5$ cells) are then mixed with serum-free methylcellulose medium optimized for hemangioblast cell growth (e.g., BL-CFU medium, for example Stem Cell Technologies Catalogue H4436, or hemangioblast cell expansion medium (HGM), or any medium containing 1.0% methylcellulose in MDM, 1-2% Bovine serum albumin, 0.1 mM 2-mercaptoethanol, 10 µg/ml rh-Insulin, 200 µg/ml iron saturated human transferrin, 20 ng/ml rh-GM-CSF, 20 ng/ml rh-IL-3, 20 ng/ml rh-IL-6, 20 ng/ml rh-G-CSF)("rh" stands for "recombinant human"). This medium may be supplemented with early stage cytokines (including, but not limited to, EPO, TPO, SCF, FL, FLt-3, VEGF, BMPs such as BMP2, BMP4 and BMP7, but not BMP3) and HOXB4 (or another homeobox protein). In certain embodiments, erythropoietin (EPO) is added to the media. In further embodiments, EPO, SCF, VEGF, BMP-4 and HoxB4 are added to the media. In additional embodiments, the cells are grown in the presence of EPO, TPO and FL. In certain embodiments where H9 is the starting human ES cell line, EPO, TPO and FL are added to the media. In addition to EPO, TPO and FL, media for cells derived from H9 or other ES cells may further comprise VEGF, BMP-4, and HoxB4.

The cells so obtained by this method (the cells may be in BL-CFU medium), which include hemangioblast cells, are plated onto ultra-low attachment culture dishes and incubated in a $CO_2$ incubator to grow hemangioblast colonies. Some cells may be able to form secondary EBs. Following approximately 3-6 days, and in some instances 3-4.5 days, hemangioblast colonies are observed. Hemangioblast colonies may be distinguished from other cells such as secondary EBs by their distinctive grape-like morphology and/or by their small size. In addition, hemangioblasts may be identified by the expression of certain markers (e.g., the expression of both early hematopoietic and endothelial cell markers) as well as their ability to differentiate into at least both hematopoietic and endothelial cells (see below. Deriving hemangioblast lineage cells). For example, while hemangioblasts lack certain features characteristic of mature endothelial or hematopoietic cells, these cells may be identified by the presence of certain markers (such as, for example, CD71+) and the absence of other markers (for example, CD34−). Hemangioblasts may also express GATA-1 and GATA-2 proteins, CXCR-4, and TPO and EPO receptors. In addition, hemangioblasts may be characterized by the absence or low expression of other markers (e.g., CD31, CD34, KDR, or other adhesion molecules). Further, hemangioblasts may be characterized by the expression of certain genes, (e.g., genes associated with hemangioblasts and early primitive erythroblast development, such as, for example, SCL, LMO2, FLT-1, embryonic fetal globin genes, NF-E2, GATA-1, EKLF, ICAM-4, glycophoriuns, and EPO receptor).

Accordingly, hemangioblasts may be isolated by size (being smaller than the other cells) or purified with an anti-CD71+ antibody, such as by immunoaffinity column chromatography.

The hemangioblast cells may be isolated by size and/or morphology by the following procedure. After 6 to 7 days of growth, the cell mixture contains EBs, which are round and represent a clump of multiple cells, and hemangioblasts, which are grape-like, smaller than the EBs, and are single cells. Accordingly, hemangioblasts may be isolated based on their morphology and size. The hemangioblast cells may be manually picked, for example, when observing the cell mixture under a microscope. The cells may subsequently grow into colonies, each colony having between 100-150 cells.

Human hemangioblast colonies derived as described above may be picked and replated onto methylcellulose CFU-medium to form hematopoietic CFUs. In certain embodiments, CFU-medium comprises StemCell Technologies H4436. In further embodiments, hemangioblasts are plated in Stemline II media supplemented with cytokines and other factors. For example, individual BL-CFC colonies may be handpicked and transferred to a fibronectin-coated plate containing Stemline II with recombinant human SCF (e.g., 20 ng/ml), TPO (e.g., 20 ng/ml), FL (e.g., 20 ng/ml), IL-3 (e.g., 20 ng/ml) VEGF (e.g., 20 ng/ml), G-CSF (e.g., 20 ng/ml), BMP-4 (e.g., 15 ng/ml), IL-6 (e.g., 10 ng/ml), IGF-1 (e.g., 10 ng/ml), endothelial cell growth supplement (EGGS, e.g., 100 µg/ml), Epo (e.g., 3 U/ml). Following one week of growth in vitro, non-adherent hematopoietic cells may be removed by gentle pipetting and used directly for hematopoietic CFU assay. Following removal of the non-adherent cells, the adherent populations may be grown for one more week in EGM-2 endothelial cell medium (Cambrex™), and then examined for the expression of vWF.

Expansion of Hemangioblasts In Vitro

Certain aspects of the invention relate to the in vitro expansion of hemangioblasts. In certain embodiments, hemangioblasts expanded by the methods of the invention are obtained from early embryoid bodies derived from human embryonic stem cells as described above.

In addition to deriving hemangioblasts from human embryonic stem cells (hES cells), hemangioblasts to be expanded may also be isolated from other mammalian sources, such as mammalian embryos (Ogawa et al. 2001 *Int Rev Immunol* (20):21-44, US patent publication no. 2004/0052771), cord blood from placenta and umbilical tissues (Pelosi, et al. 2002 Blood (100): 3203-3208; Cogle et al. 2004 Blood (103):133-5), peripheral blood and bone marrow (Pelosi et al. 2002 Hematopoiesis (100): 3203-3208). In certain embodiments, non-human hemangioblasts to be expanded may be generated from non-human (such as mouse and non-human primates) embryonic stem cells. In certain embodiments, hemangioblasts are obtained from umbilical cord blood (UCB) or bone marrow by methods such as, for example, magnetic bead positive selection or purification techniques (e.g. MACS column). Cells may be selected based on their CD71+ status and may be confirmed as CD34−. Further, the isolated hemangioblasts may be tested for their potential to give rise to both hematopoietic and endothelial cell lineages. In certain embodiments, hemangioblasts isolated or purified and optionally enriched from embryos, cord blood, peripheral blood, bone marrow, or other tissue, are more than 95% pure.

Bone marrow-derived cells may be obtained from any stage of development of the donor individual, including prenatal (e.g., embryonic or fetal), infant (e.g., from birth to approximately three years of age in humans), child (e.g., from about three years of age to about 13 years of age in humans), adolescent (e.g., from about 13 years of age to about 18 years of age in humans), young adult (e.g., from about 18 years of age to about 35 years of age in humans), adult (from about 35 years of age to about 55 years of age in humans) or elderly (e.g. from about 55 years and beyond of age in humans).

Human bone marrow may be harvested by scraping from the split sternum of a patient undergoing surgery, for example. Bone marrow may then be preserved in tissue clumps of 0.1 to 1 mm$^3$ in volume and then grown on a mouse embryonic feeder layer (e.g., a mitomycin C-treated or irradiated feeder layer). The bone marrow cells will attach to the plates and over a period of 1-2 weeks of culture, hemangioblast cells may be identified based on morphological features and/or cell markers and isolated (see US patent publication no. 2004/0052771). The cells may then be subsequently grown and expanded in serum-free conditions according to the methods disclosed herein.

In addition, bone marrow cells and cells from blood or other tissue may be fractionated to obtain hemangioblasts cells. Methods of fractionation are well known in the art, and generally involve both positive selection (i.e., retention of cells based on a particular property) and negative selection (i.e., elimination of cells based on a particular property). Methods for fractionation and enrichment of bone marrow-derived cells are best characterized for human and mouse cells.

There are a variety of methods known in the art for fractionating and enriching bone marrow-derived or other cells. Positive selection methods such as enriching for cells expressing CD71 may be used. And negative selection methods which remove or reduce cells expressing CD3, CD10, CD11b, CD14, CD16, CD15, CD16, CD19, CD20, CD32, CD45, CD45R/B220 or Ly6G may also be used alone or in combination with positive selection techniques. In the case of bone marrow cells, when the donor bone marrow-derived cells are not autologous, negative selection may be performed on the cell preparation to reduce or eliminate differentiated T cells.

Generally, methods used for selection/enrichment of bone marrow-derived, blood, or other cells will utilize immunoaffinity technology, although density centrifugation methods are also useful. Immunoaffinity technology may take a variety of forms, as is well known in the art, but generally utilizes an antibody or antibody derivative in combination with some type of segregation technology. The segregation technology generally results in physical segregation of cells bound by the antibody and cells not bound by the antibody, although in some instances the segregation technology which kills the cells bound by the antibody may be used for negative selection.

Any suitable immunoaffinity technology may be utilized for selection/enrichment of hemangioblasts from bone marrow-derived, blood, or other cells, including fluorescence-activated cell sorting (FACS), panning, immunomagnetic separation, immunoaffinity chromatography, antibody-mediated complement fixation, immunotoxin, density gradient segregation, and the like. After processing in the immunoaffinity process, the desired cells (the cells bound by the immunoaffinity reagent in the case of positive selection, and cells not bound by the immunoaffinity reagent in the case of negative selection) are collected and may be subjected to further rounds of immunoaffinity selection/enrichment.

Immunoaffinity selection/enrichment is typically carried out by incubating a preparation of cells comprising bone marrow-derived cells with an antibody or antibody-derived affinity reagent (e.g., an antibody specific for a given surface marker), then utilizing the bound affinity reagent to select either for or against the cells to which the antibody is bound. The selection process generally involves a physical separation, such as can be accomplished by directing droplets containing single cells into different containers depending on the presence or absence of bound affinity reagent (FACS), by utilizing an antibody bound (directly or indirectly) to a solid phase substrate (panning, immunoaffinity chromatography), or by utilizing a magnetic field to collect the cells which are bound to magnetic particles via the affinity reagent (immunomagnetic separation). Alternatively, undesirable cells may be eliminated from the bone marrow-derived cell preparation using an affinity reagent which directs a cytotoxic insult to the cells bound by the affinity reagent. The cytotoxic insult may be activated by the affinity reagent (e.g., complement fixation), or may be localized to the target cells by the affinity reagent (e.g., immunotoxin, such as ricin B chain).

Although the methods described above refer to enrichment of cells from a preparation of bone marrow-derived or blood cells, one skilled in the art will recognize that similar positive and negative selection techniques may be applied to cell preparations from other tissues.

Certain aspects of the invention relate to the in vitro expansion of hemangioblasts. In certain embodiments, hemangioblasts expanded by the methods of the invention are obtained from early embryoid bodies derived from human embryonic stem cells as described above. In other embodiments, the hemangioblasts are isolated or enriched from human tissue (e.g., placenta or cord blood, peripheral blood, bone marrow, etc.)

In certain embodiments, the hemangioblasts are expanded in the presence of a homeodomain protein (also referred to herein as a homeobox protein). In further embodiments, the hemangioblasts are expanded in the presence of HOXB4. In certain embodiments, HOXB4 is added to the hemangioblast cells throughout the method for expanding hemangioblast cells.

HOXB4 is a homeodomain transcription factor (also called HOX2F, HOX2, HOX-2.6, and in the rat HOXA5) that is expressed in vivo in the stem cell fraction of the bone marrow and that is subsequently down-regulated during differentiation. Expression of the HOXB4 gene is associated with the maintenance of primitive stem cell phenotypes (Sauvageau et al., 1995 *Genes Dev* 9: 1753-1765; Buske et al. 2002 *Blood* 100: 862-868; Thorsteinsdottir et al. 1999 *Blood* 94: 2605-2612; Antonchuk et al. 2001 *Exp Hematol* 29: 1125-1134).

HOXB4 used in the methods of the present invention to generate and expand hemangioblasts, includes, but is not limited to, full length HOXB4 (e.g., HOXB4 polypeptides specified by public accession numbers GI:13273315 (FIG. 9), GI:29351568 (FIG. 10), as well as any functional variants and active fragments thereof. The wild-type HOXB4 protein may be encoded by the amino acid sequence of SEQ ID NO: 1 (FIG. 9), SEQ ID NO: 3 (FIG. 10) or any other alternative allelic forms of such protein. Such sequences may be accessed via publicly available databases, such as Genbank. Further, HOXB4 may be ectopically expressed within the cell or may be provided in the media. HOXB4 expressed ectopically may be operably linked to an inducible promoter. HOXB4 provided in the media may be excreted by another cell type (e.g., a feeder layer) or added directly to the media.

The present invention also relates to fusion proteins comprising HOXB4 (including fusion proteins comprising full length HOXB4, or HOXB4 functional variants or active fragments of HOXB4). In addition to HOXB4, this fusion protein may also comprise any additional proteins, protein domains or peptides. In certain embodiments, HOXB4 may be joined to a protein transduction domain (PTD) to allow translocation of the protein from the medium into the cells and subsequently into nuclear compartments. Fusion proteins may or may not comprise one or more linker sequences located in between the protein domains.

Functional variants of HOXB4 include mutants of HOXB4 and allelic variants, and active fragments thereof. Functional variants of HOXB4 include any HOXB4 polypeptides and active fragments thereof that are capable of expanding hemangioblasts according to the methods of the present invention. HOXB4 functional variants also include HOXB4 polypeptides that exhibit greater transcriptional activity compared to the native HOXB4 protein. HOXB4 variants include proteins with one or more amino acid substitution, addition, and/or deletion in relation to a wild-type HOXB4. HOXB4 variants also include, but are not limited to, polypeptides that are at least 75% similar to the sequence provided in SEQ ID NO: 1 or SEQ ID NO: 3. Accordingly, HOXB4 variants include polypeptides that are 80%, 85%, 90%, 95%, and 99% similar to the amino acid sequence provided in SEQ ID NO: 1 or SEQ ID NO: 3.

HOXB4 variants also include polypeptides encoded by nucleic acid sequences that are at least 80% identical to a nucleic acid sequence encoding its complement (e.g., the wild-type HOXB4 protein may be encoded by nucleic acid sequences of SEQ ID NO: 2 (GI:85376187; FIG. 7) or SEQ ID NO: 4 (GI:29351567; FIG. 8)). Thus, HOXB4 variants include HOXB4 polypeptides that are encoded by nucleic acid sequences that are 85%, 90%, 95%, and 99% identical to the sequence provided in SEQ ID NO: 2 or SEQ ID NO: 4 or complement thereto.

Nucleic acid sequences encoding HOXB4 also include, but are not limited to, any nucleic acid sequence that hybridizes under stringent conditions to a nucleic acid sequence of SEQ ID NO: 2 or 4, complement thereto, or fragment thereof. Similarly, nucleic acids which differ from the nucleic acids as set forth in SEQ ID NO: 2 or 4 due to degeneracy in the genetic code are also within the scope of the invention. HOXB4 variant polypeptides also include splice variants or other naturally occurring HOXB4 proteins or nucleic acid sequences.

Active fragments of HOXB4 include, but are not limited to, any fragment of full length HOXB4 polypeptide that is capable of maintaining hemangioblasts according to the methods of the present invention. Accordingly, in one embodiment, a HOXB4 protein of the present invention is a HOXB4 protein that lacks part of the N-terminus, such as, for example, the N-terminal 31, 32, or 33 amino acids of full length HOXB4.

Any of the HOXB4 proteins may be fused with additional proteins or protein domains. For example, HOXB4 may be joined to a protein transduction domain (PTD).

Protein transduction domains, covalently or non-covalently linked to HOXB4, allow the translocation of HOXB4 across the cell membranes so the protein may ultimately reach the nuclear compartments of the cells.

PTDs that may be fused with a HOXB4 protein include the PTD of the HIV transactivating protein (TAT) (Tat 47-57) (Schwarze and Dowdy 2000 *Trends Pharmacol. Sci.* 21: 45-48; Krosl et al. 2003 *Nature Medicine* (9): 1428-1432). For the HIV TAT protein, the amino acid sequence conferring membrane translocation activity corresponds to residues 47-57 (YGRKKRRQRRR, SEQ ID NO: 5) (Ho et al., 2001, *Cancer Research* 61: 473-477; Vives et al., 1997, *J. Biol. Chem.* 272: 16010-16017). This sequence alone can confer protein translocation activity. The TAT PTD may also be the nine amino acids peptide sequence RKKRRQRRR (SEQ ID NO: 6) (Park et al. *Mol Cells* 2002 (30):202-8). The TAT PTD sequences may be any of the peptide sequences disclosed in Ho et al., 2001, *Cancer Research* 61: 473-477 (the disclosure of which is hereby incorporated by reference herein), including YARKARRQARR (SEQ ID NO: 7), YARAAARQARA (SEQ ID NO: 8), YARAARRAARR (SEQ ID NO: 9) and RARAARRAARA (SEQ ID NO: 10).

Other proteins that contain PTDs that may be fused to HOXB4 proteins of the present invention include the herpes simplex virus 1 (HSV-1) DNA-binding protein VP22 and the *Drosophila* Antennapedia (Antp) homeotic transcription factor (Schwarze et al. 2000 *Trends Cell Biol.* (10): 290-295). For Antp, amino acids 43-58 (RQIKIWFQNRRMKWKK, SEQ ID NO: 11) represent the protein transduction domain, and for HSV VP22 the PTD is represented by the residues DAATATRGRSAASRPTERPRAPARSASRPRRPVE (SEQ ID NO: 12). Alternatively, HeptaARG (RRRRRRR, SEQ ID NO: 13) or artificial peptides that confer transduction activity may be used as a PTD of the present invention.

In additional embodiments, the PTD may be a PTD peptide that is duplicated or multimerized. In certain embodiments, the PTD is one or more of the TAT PTD peptide YARAAAR-QARA (SEQ ID NO: 14). In certain embodiments, the PTD is a multimer consisting of three of the TAT PTD peptide YARAAARQARA (SEQ ID NO: 15). A HOXB4 protein that is fused or linked to a multimeric PTD, such as, for example, a triplicated synthetic protein transduction domain (tPTD), may exhibit reduced lability and increased stability in cells. Such a HOXB4 construct may also be stable in serum-free medium and in the presence of hES cells.

Techniques for making fusion genes encoding fusion proteins are well known in the art. Essentially, the joining of various DNA fragments coding for different polypeptide sequences is performed in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

In certain embodiments, a fusion gene coding for a purification leader sequence, such as a poly-(His) sequence, may be linked to the N-terminus of the desired portion of the HOXB4 polypeptide or HOXB4-fusion protein, allowing the fusion protein be purified by affinity chromatography using a $Ni^{2+}$ metal resin. The purification leader sequence can then be subsequently removed by treatment with enterokinase to provide the purified HOXB4 polypeptide (e.g., see Hochuli et al., (1987) *J. Chromatography* 411:177; and Janknecht et al., *PNAS USA* 88:8972).

In certain embodiments, a HOXB4 protein or functional variant or active domain of it, is linked to the C-terminus or the N-terminus of a second protein or protein domain (e.g., a PTD) with or without an intervening linker sequence. The exact length and sequence of the linker and its orientation relative to the linked sequences may vary. The linker may comprise, for example, 2, 10, 20, 30, or more amino acids and may be selected based on desired properties such as solubility, length, steric separation, etc. In particular embodiments, the linker may comprise a functional sequence useful for the purification, detection, or modification, for example, of the fusion protein. In certain embodiments, the linker comprises a polypeptide of two or more glycines.

The protein domains and/or the linker by which the domains are fused may be modified to alter the effectiveness, stability and/or functional characteristics of HOXB4.

In certain embodiments, HOXB4 is ectopically expressed within the hemangioblast cell or is provided in the media. HOXB4 expressed ectopically may be operably linked to a regulatory sequence. Regulatory sequences are art-recognized and are selected to direct expression of the HOXB4 polypeptide.

HOXB4 provided in the media may be excreted by another cell type. The other cell type may be a feeder layer, such as a mouse stromal cell layer transduced to express excretable HOXB4. For example, HOXB4 may be fused to or engineered to comprise a signal peptide, or a hydrophobic sequence that facilitates export and secretion of the protein. Alternatively, HOXB4, such as a fusion protein covalently or non-covalently linked to a PTD, may be added directly to the media. Additionally, HOXB4 may be borne on a viral vector, such as a retroviral vector or an adenoviral vector. Such a vector could transduce either the hemangioblasts or other cells in their culture.

Depending on the HOXB4 protein used, in particular embodiments HOXB4 is added to the media at selected times during the expansion of the hemangioblasts. Because the hemangioblasts are expanded in serum-free medium, HOXB4 is relatively stable. Accordingly, in certain embodiments, a HOXB4 protein or fusion protein is added every day to the human hemangioblasts. In other embodiments, a HOXB4 protein or fusion protein is added every other day, and in still other embodiments, a HOXB4 protein or fusion protein is added every 2 days. In one embodiment, a HOXB4 fusion protein, HOXB4-PTD, is added every 2 days to the media.

In certain embodiments, the hemangioblasts can be expanded in the presence of any other growth factors or proteins that are present in an amount sufficient to expand such cells.

Hemangioblasts obtained from any source, including human or non-human ES cells, bone marrow, placenta or umbilical cord blood, peripheral blood, or other tissue may be expanded according to the methods described above. Accordingly, in certain embodiments, a select number of purified hemangioblasts or enriched cells are mixed with serum-free methylcellulose medium optimized for hemangioblast growth (e.g., BL-CFU medium, see Example 1 and 2). This medium may be supplemented with early stage cytokines (including, but not limited to, EPO, TPO, FL, VGF, BMPs like BMP2, BMP4 and BMP7, but not BMP3) and HOXB4. In certain embodiments, erythropoietin (EPO) is added to the media. In certain embodiments, EPO, TPO and FL are added to the media. The cells are then plated onto ultra-low attachment culture dishes and grown in a $CO_2$ incubator. As mentioned above, hemangioblast colonies exhibit a distinctive grape-like morphology and are comparatively smaller than other cells and may consequently be distinguished from other cell types. The hemangioblasts may also be tested for markers as well as for their ability to differentiate further into either hematopoietic or endothelial cell lineages. The hemangioblasts are subsequently isolated and expanded in vitro. Media that may be used for expansion includes serum-free methylcellulose medium optimized for hemangioblasts growth (e.g., BL-CFU) supplemented with early stage cytokines and HOXB4. Early stage cytokines include, but are not limited to, EPO, TPO, FL, VEGF, BMPs like BMP2, BMP4 and BMP7, but not BMP3. In certain embodiments, erythropoietin (EPO) is added to the medium. In further embodiments, EPO, TPO and FL are added to the medium.

Accordingly, a medium for expanding hemangioblasts may comprise VEGF, SCF, EPO, BMP-4, and HoxB4; in certain embodiments the medium may further comprise TPO and FL. For example, single cells prepared from EBs cultured for approximately 3.5 days, were collected and dissociated by 0.05% trypsin-0.53 mM EDTA (Invitrogen) for 2-5 min, and a single cell suspension was prepared by passing through 22G needle 3-5 times. Cells were collected by centrifugation at 1,000 rpm for 5 min. Cell pellets were resuspended in 50-200 µl of Stemline I media. To expand hemangioblasts, single cell suspension derived from differentiation of 2 to $5\times10^5$ hES cells were mixed with 2 ml hemangioblast expansion media (HGM) containing 1.0% methylcellulose in Iscove's MDM, 1-2% Bovine serum albumin, 0.1 mM 2-mercaptoethanol, 10 µg/ml rh-Insulin, 200 µg/ml iron saturated human transferrin, 20 ng/ml rh-GM-CSF, 20 ng/ml rh-IL-3, 20 ng/ml rh-IL-6, 20 ng/ml rh-G-CSF, 3 to 6 units/ml rh-Epo, 50 ng/ml rh-SCF, 50 ng/ml rh-VEGF and 50 ng/ml rh-BMP-4, and 1.5 µg/ml of tPTD-HoxB4, with/without 50 ng/ml of Tpo and FL. The cell mixtures were plated on ultra-low dishes and incubated at 37° C. in 5% $CO_2$ for 4-6 days.

In certain situations it may be desirable to obtain hemangioblasts from a patient or patient relative and expand said hemangioblasts in vitro. Such situations include, for example, a patient scheduled to begin chemotherapy or radiation therapy, or other situations wherein an autologous HSC transplantation (using the patient's own stem cells) may be used. Thus, the present invention provides methods of treating patients in need of cell-based therapy (for example, patients in need of hematopoietic reconstitution or treatment, or blood vessel growth or treatment of vascular injuries including ischemia, see below) using the expanded hemangioblasts or hemangioblast lineage cells of the invention, wherein the hemangioblasts are obtained from the bone marrow, blood, or other tissue of the patient or a patient relative. Accordingly, in certain embodiments, methods of treating a patient in need of hemangioblasts (or hemangioblast lineage cells) may comprise a step of isolating hemangioblasts from the patient or a patient relative. Hemangioblasts isolated from the patient or patient relative may be expanded in vitro according to the methods of the present invention and subsequently administered to the patient. Alternatively the expanded hemangioblasts may be grown further to give rise to hematopoietic cells or endothelial cells before patient treatment.

It is also possible to obtain human ES cells from such a patient by any method known in the art, such as somatic cell nuclear transfer. Hemangioblasts of that patient may then be generated and expanded from his own ES cells using a method of this invention. Those hemangioblasts or lineage derivatives thereof may be administered to that patient or to his relatives.

Using the methods of the present invention, human hemangioblasts are expanded to reach commercially large quantities which can be subsequently used in various therapeutic and clinical applications. Furthermore, the hemangioblasts obtained by the methods disclosed herein may be differentiated further to give rise to either hematopoietic or endothelial cell lineages for use in clinical applications.

The hemangioblasts obtained from the method of this invention for generating and expanding human hemangioblasts from human ES cells have the potential to differentiate into at least endothelial cells or hematopoietic cells (i.e., they are at least bi-potential). Other hemangioblasts may be bi-potential as well. Yet other hemangioblasts may be able to differentiate into cells other than hematopoietic and endothelial cells, i.e., they are multi- or pluri-potential).

Engineering MHC Genes in Human Embryonic Stem Cells to Obtain Reduced-Complexity Hemangioblasts The human embryonic stem cells used as the starting point for the method of generating and expanding human hemangioblast cells of this invention may also be derived from a library of human embryonic stem cells, each of which is hemizygous or homozygous for at least one MHC allele present in a human population. In certain embodiments, each member of said library of stem cells is hemizygous or homozygous for a different set of MHC alleles relative to the remaining members of the library. In certain embodiments, the library of stem cells is hemizygous or homozygous for all MHC alleles that are present in a human population. In the context of this invention, stem cells that are homozygous for one or more histocompatibility antigen genes include cells that are nullizygous for one or more (and in some embodiments, all) such genes. Nullizygous for a genetic locus means that the gene is null at that locus, i.e., both alleles of that gene are deleted or inactivated. Stem cells that are nullizygous for all MHC genes may be produced by standard methods known in the art, such as, for example, gene targeting and/or loss of heterozygosity (LOH). See, for example, United States patent publications US 20040091936, US 20030217374 and US 20030232430, and U.S. provisional application No. 60/729, 173, the disclosures of all of which are hereby incorporated by reference herein.

Accordingly, the present invention relates to methods of obtaining hemangioblasts, including a library of hemangioblasts, with reduced MHC complexity. Hemangioblasts and hemangioblast lineage cells with reduced MHC complexity will increase the supply of available cells for therapeutic applications as it will eliminate the difficulties associated with patient matching. Such cells may be derived from stem cells that are engineered to be hemizygous or homozygous for genes of the MHC complex.

A human ES cell may comprise modifications to one of the alleles of sister chromosomes in the cell's MHC complex. A variety of methods for generating gene modifications, such as gene targeting, may be used to modify the genes in the MHC complex. Further, the modified alleles of the MHC complex in the cells may be subsequently engineered to be homozygous so that identical alleles are present on sister chromosomes. Methods such as loss of heterozygosity (LOH) may be utilized to engineer cells to have homozygous alleles in the MHC complex. For example, one or more genes in a set of MHC genes from a parental allele can be targeted to generate hemizygous cells. The other set of MHC genes can be removed by gene targeting or LOH to make a null line. This null line can be used further as the embryonic cell line in which to drop arrays of the HLA genes, or individual genes, to make a hemizygous or homozygous bank with an otherwise uniform genetic background.

In one aspect, a library of ES cell lines, wherein each member of the library is homozygous for at least one HLA gene, is used to derive hemangioblasts according to the methods of the present invention. In another aspect, the invention provides a library of hemangioblasts (and/or hemangioblast lineage cells), wherein several lines of ES cells are selected and differentiated into hemangioblasts. These hemangioblasts and/or hemangioblast lineage cells may be used for a patient in need of a cell-based therapy.

Accordingly, certain embodiments of this invention pertain to a method of administering human hemangioblasts, hematopoietic stem cells, or human endothelial cells that have been derived from reduced-complexity embryonic stem cells to a patient in need thereof. In certain embodiments, this method comprises the steps of: (a) identifying a patient that needs treatment involving administering human hemangioblasts, hematopoietic stem cells, or human endothelial cells to him or her; (b) identifying MHC proteins expressed on the surface of the patient's cells; (c) providing a library of human hemangioblasts of reduced MHC complexity made by the method for generating and expanding human hemangioblast cells in vitro of the present invention; (d) selecting the human hemangioblast cells from the library that match this patient's MHC proteins on his or her cells; (e) optionally differentiating the human hemangioblast cells identified in step (d) into human hematopoietic stem cells, endothelial cells or both, or cells that are further differentiated in either or both of these two lineages, depending on need; (f) administering any of the cells from step (d) and/or (e) to said patient. This method may be performed in a regional center, such as, for example, a hospital, a clinic, a physician's office, and other health care facilities. Further, the hemangioblasts selected as a match for the patient, if stored in small cell numbers, may be expanded prior to patient treatment.

Human Hemangio-Colony Forming Cells/Hemangioblasts

In certain aspects, the present invention provides human hemangio-colony forming cells. These cells are a unique, primitive cell type with a variety of therapeutic and other uses. Furthermore, this cell type provides an important tool for studying development of at least the hematopoietic and/or endothelial lineages. As such, the invention contemplates various preparations (including pharmaceutical preparations) and compositions comprising human hemangio-colony forming cells, as well as preparations (including pharmaceutical preparations) and compositions comprising one or more cell types partially or terminally differentiated from hemangio-colony forming cells.

Human hemangio-colony forming cells of the present invention have at least one of the following structural characteristics: (a) can differentiate to give rise to at least hematopoietic cell types or endothelial cell types; (b) can differentiate to give rise to at least hematopoietic cell types and endothelial cell types; (c) are loosely adherent to each other (to other human hemangio-colony forming cells; (d) do not express CD34 protein; (e) do not express CD31 protein; (f) do not express KDR protein; (g) do not express CD133 protein; (h) express GATA2 protein; (i) express LMO2 protein. In certain embodiments, human hemangio-colony forming cells have at least two, at least three, at least four, at least five, at least six, at least seven, at least eight, or at least nine of the structural or functional characteristics detailed herein.

The invention provides for human hemangio-colony forming cells. Such cells can differentiate to produce at least hematopoietic and/or endothelial cell types. In certain embodiments, the cells are characterized as being loosely adherent to other human hemangio-colony forming cells. Alternatively or additionally, these cells may also be described based on expression or lack of expression of certain markers. For example, these cells may also be described based on lack of expression of at least one of the following proteins: CD34, KDR, CD133, and CD31.

As detailed above, one of the interesting properties of human hemangio-colony forming cells is that they are loosely adherent to each other. Because these cells are only loosely adherent to each other, cultures or colonies of hemangio-colony forming cells can be dissociated to single cells using only mechanical dissociation techniques and without the need for enzymatic dissociation techniques. The cells are sufficiently loosely adherent to each other that mechanical dissociation alone, rather than enzymatic dissociation or a combination thereof, is sufficient to disaggregate the cultures or colonies without substantially impairing the viability of the cells. In other words, mechanical dissociation does not require so much force as to cause substantial cell injury or death.

This property is not only useful in describing the cells and distinguishing them phenotypically from other cell types, but it also has significant therapeutic implications. For example, relatively large numbers (greater than $1\times10^6$ or even greater than $1\times10^7$ or even greater than $1\times10^8$) of the hemangio-colony forming cells can be injected into humans or other animals with substantially less risk of causing clots or emboli, or otherwise lodging in the lung. This is a significant advance in cellular therapy. The ability to safely administer relatively large numbers of cells makes cellular therapy practical and possible for the effective treatment of an increasing number of diseases and conditions.

The term "loosely adherent" is described qualitatively above and refers to behavior of the human hemangio-colony forming cells with respect to each other. Cultures or colonies of hemangio-colony forming cells can be dissociated to single cells using only mechanical dissociation techniques and without the need for enzymatic dissociation techniques. The cells are sufficiently loosely adherent to each other that mechanical dissociation alone, rather than enzymatic dissociation or a combination thereof, is sufficient to disaggregate the cultures or colonies without substantially impairing the viability of the cells. In other words, mechanical dissociation does not require so much force as to cause substantial cell injury or death.

The term can also be described more quantitatively. For example and in certain embodiments, the term "loosely adherent" is used to refer to cultures or colonies of hemangio-colony forming cells wherein at least 50% of the cells in the culture can be dissociated to single cells using only mechanical dissociation techniques and without the need for enzymatic dissociation techniques. In other embodiments, the term refers to cultures in which at least 60%, 65%, 70%, or 75% of the cells in the culture can be dissociated to single cells using only mechanical dissociation techniques and without the need for enzymatic dissociation techniques. In still other embodiments, the term refers to cultures in which at least 80%, 85%, 90%, 95%, 96%, 97%, 98%, 99%, or even 100% of the cells in the culture can be dissociated to single cells using only mechanical dissociation techniques and without the need for enzymatic dissociation techniques.

The ability to dissociate the hemangio-colony forming cells using only mechanical dissociation techniques and without the need for enzymatic dissociation techniques can be further quantitated based on the health and viability of the cells following mechanical dissociation. In other words, if dissociation without enzymatic techniques requires so much mechanical force that a significant number of the cells are damaged or killed, the cells are not loosely adherent, as defined herein. For example and in certain embodiments, the term "loosely adherent" refers to cultures of cells that can be dissociated to single cells using only mechanical dissociation techniques and without the need for enzymatic dissociation techniques, without substantially impairing the health or viability or the cells in comparison to that observed when the same cells are dissociated using enzymatic dissociation techniques. For example, the health or viability of the cells is decreased by less than 15%, 10%, 9%, 8%, 7%, 6%, 5%, 4%, 3%, 2%, or even less than 1% in comparison to that observed when a culture of the same cells are dissociated using enzymatic dissociation techniques.

Exemplary enzymatic dissociation techniques include, but are not limited to, treatment with trypsin, collagenase, or other enzymes that disrupt cell-cell or cell-matrix interactions. Exemplary mechanical dissociation techniques include, but are not limited to, one or more passages through a pipette.

Human hemangio-colony forming cells according to the present invention are defined structurally and functionally. Such cells can be generated from any of a number of sources including from embryonic tissue, prenatal tissue, perinatal tissue, and even from adult tissue. By way of example, human hemangio-colony forming cells can be generated from human embryonic stem cells, other embryo-derived cells (blastocysts, blastomeres, ICMs, embryos, trophoblasts/trophectoderm cells, trophoblast stem cells, primordial germ cells, embryonic germ cells, etc.), amniotic fluid, amniotic stem cells, placenta, placental stem cells, and umbilical cord.

The invention provides human hemangio-colony forming cells, compositions comprising human hemangio-colony forming cells, and preparations (including pharmaceutical preparations) comprising human hemangio-colony forming cells. Certain features of these aspects of the invention are described in detail below. The invention contemplates combinations of any of the following aspects and embodiments of the invention.

In one aspect, the invention provides a human hemangio-colony forming cell. The cell can differentiate to produce at least hematopoietic and/or endothelial cell types. In certain embodiments, the cell is loosely adherent to other human hemangio-colony forming cells. In certain embodiments, the cell does not express CD34 protein. In certain other embodiments, the cell does not express one or more of (e.g., the cell does not express at least one, at least two, at least three, or at least four of the following proteins) the following proteins: CD34, CD31, CD133, KDR. In certain other embodiments, the cell does express GATA2 and/or LMO2 protein.

In another aspect, the invention provides a human hemangio-colony forming cell. The cell, which cell can differentiate to produce at least hematopoietic and/or endothelial cell types, and the cell does not express any of the following proteins: CD34, CD31, KDR, and CD133. In certain embodiments, the cell is loosely adherent to other human hemangio-colony forming cells. In other embodiments, the cell does express GATA2 and/or LMO2 protein.

In another aspect, the invention provides a cell culture comprising a substantially purified population of human hemangio-colony forming cells. The cells can differentiate to produce at least hematopoietic and endothelial cell types, and the cells are loosely adherent to each other. In certain embodiments, the cell does not express CD34 protein. In certain other embodiments, the cell does not express one or more of (e.g.,
the cell does not express at least one, at least two, at least three, or at least four of the following proteins) the following proteins: CD34, CD31, CD133, KDR. In certain other embodiments, the cell does express GATA2 and/or LMO2 protein.

In another aspect, the invention provides a cell culture comprising human hemangio-colony forming cells differentiated from embryonic tissue. In certain embodiments, the hemangio-colony forming cells are loosely adherent to each other. In certain embodiments, the cells can differentiate to produce at least hematopoietic and/or endothelial cell types, and the cells are loosely adherent to each other. In certain embodiments, the cell does not express CD34 protein. In certain other embodiments, the cell does not express one or more of (e.g., the cell does not express at least one, at least two, at least three, or at least four of the following proteins) the following proteins: CD34, CD31, CD133, KDR. In certain other embodiments, the cell does express GATA2 and/or LMO2 protein.

In another aspect, the invention provides a cell culture comprising human hemangio-colony forming cells, which cells can differentiate to produce at least hematopoietic and/or endothelial cell types. In certain embodiments, the cells are loosely adherent to each other. In certain embodiments, the cell does not express CD34 protein. In certain other embodiments, the cell does not express one or more of (e.g., the cell does not express at least one, at least two, at least three, or at least four of the following proteins) the following proteins: CD34, CD31, CD133, KDR. In certain other embodiments, the cell does express GATA2 and/or LMO2 protein.

In another aspect, the invention provides a pharmaceutical preparation comprising human hemangio-colony forming cells, which cells can differentiate to produce at least hematopoietic and/or endothelial cell types. In certain embodiments, the hemangio-colony forming cells are loosely adherent to each other. In certain embodiments, the cell does not express CD34 protein. In certain other embodiments, the cell does not express one or more of (e.g., the cell does not express at least one, at least two, at least three, or at least four of the following proteins) the following proteins: CD34, CD31, CD133, KDR. In certain other embodiments, the cell does express GATA2 and/or LMO2 protein. The pharmaceutical preparation can be prepared using any pharmaceutically acceptable carrier or excipient.

In another aspect, the invention provides a pharmaceutical preparation comprising human hemangio-colony forming cells, wherein the hemangio-colony forming cells do not express any of the following proteins: CD34, CD31, KDR, and CD133. In certain embodiments, the hemangio-colony forming cells can differentiate to produce at least hematopoietic and/or endothelial cell types. In certain embodiments, the hemangio-colony forming cells are loosely adherent to each other. In certain other embodiments, the cell does express GATA2 and/or LMO2 protein. The pharmaceutical preparation can be prepared using any pharmaceutically acceptable carrier or excipient.

In certain embodiments of any of the foregoing, the composition or pharmaceutical preparation comprises at least $1 \times 10^5$ human hemangio-colony forming cells, in certain other embodiment, of any of the foregoing, the composition or pharmaceutical preparation comprises at least $1 \times 10^6$, at least $5 \times 10^6$, at least $1 \times 10^7$, or greater than $1 \times 10^7$ human hemangio-colony forming cells.

Additional cells, compositions, and preparations include cells partially or terminally differentiated from human hemangio-colony forming cells. For example, the invention contemplates compositions and preparations comprising one or more hematopoietic and/or endothelial cell type differentiated from a hemangio-colony forming cell. Exemplary hematopoietic cell types include hematopoietic stem cells, platelets, RBCs, lymphocytes, megakaryocytes, and the like. By way of further examples, the invention contemplates compositions and preparations comprising one or more other cell type, such as one or more partially or terminally differentiated mesodermal cell type, differentiated from hemangio-colony forming cells.

In certain embodiments of any of the foregoing, the invention provides a cryopreserved preparation of human hemangio-colony cells or cells partially or terminally differentiated therefrom.

In certain embodiments of any of the foregoing, the invention provides for the therapeutic use of human hemangio-colony forming cells, or compositions or preparations of human hemangio-colony forming cells. Such cells and preparations can be used in the treatment of any of the conditions or diseases detailed throughout the specification, as well as in the blood banking industry. Furthermore, cells differentiated from human hemangio-colony forming cells, or compositions or preparations of human hemangio-colony forming cells, can be used therapeutically in the treatment of any of the conditions or diseases detailed throughout the specification, as well as in the blood banking industry.

The human hemangio-colony forming cells of the invention are can be used therapeutically. Additionally or alternatively, human hemangio-colony forming cells can be used to study development of endothelial and hematopoietic lineages or in screening assays to identify factors that can be used, for example, to (i) maintain human hemangio-colony forming cells or (ii) to promote differentiation of human hemangio-colony forming cells to one or more partially or terminally differentiated cell types. Furthermore, human hemangio-colony forming cells can be used to generate one or more partially or terminally differentiated cell types for in vitro or in vivo use.

The human hemangio-colony forming cells of the invention can be used in any of the methods or application described in the present application including, but not limited to, in the treatment of any of the diseases or conditions described herein.

Cell Preparations Comprising Hemangioblasts Expanded In Vitro

In certain embodiments of the present invention, mammalian (including human) hemangioblasts are expanded to reach commercial quantities and are used in various therapeutic and clinical applications. In particular embodiments, hemangioblasts are expanded to reach cell numbers on the order of 10,000 to 4 million (or more). These cell numbers may be reached within 3-4 days of starting the initial preparations. Accordingly, the present invention relates to preparations comprising large numbers of hemangioblasts, said preparations comprising at least 10,000, 50,000, 100,000, 500,000, a million, 2 million, 3 million or 4 million cells.

This invention also provides for a solution, a composition, and a preparation comprising large numbers of hemangioblasts, said solution, said composition, and said preparation comprising at least 10,000, 50,000, 100,000, 500,000, a million, 2 million, 3 million or 4 million cells. The hemangioblasts could be human.

Other aspects of the present invention relate to differentiating the hemangioblasts obtained by the methods disclosed herein into either hematopoietic or endothelial cell lineages, or both, that are subsequently used in clinical applications. Thus, the present invention also relates to cell preparations comprising large numbers of hematopoietic or endothelial cells. The invention also relates to differentiating the hemangioblasts obtained by the methods disclosed herein into other cell lineages, other than hematopoietic and endothelial cells. Thus, the present invention also relates to cell preparations comprising large numbers of other hemangioblast-derived cells.

Compositions and preparations comprising large numbers (e.g., thousands or millions) of hemangioblasts may be obtained by expanding hemangioblasts that are obtained as described above. Accordingly, the invention pertains to compositions and preparations comprising large numbers of hemangioblasts achieved by expanding ES cells (such as human ES cells) or hemangioblasts obtained from cord blood, peripheral blood or bone marrow. Further, as the methods of expansion may be applied to hemangioblasts of mouse, rat, bovine, or non-human primate origin, for example, the present invention also relates to compositions and preparations comprising large numbers of hemangioblasts of other species in addition to human. The hemangioblasts to be expanded by the methods of this invention may be bi-potential, i.e., can differentiate into either endothelial cells or hematopoietic stem cells. In certain embodiments, the human hemangioblasts generated and expanded from human ES cells are bi-potential. Hemangio-colony forming cells are capable of differentiating to give rise to at least hematopoietic cell types or endothelial cell types. Hemangio-colony forming cells are preferably bi-potential and capable of differentiating to give rise to at least hematopoietic cell types and endothelial cell types. As such, hemangio-colony forming cells of the present invention are at least uni-potential, and preferably bi-potential. Additionally however, hemangio-colony forming cells may have a greater degree of developmental potential and can, in certain embodiments, differentiate to give rise to cell types of other lineages. In certain embodiments, the hemangio-colony forming cells are capable of differentiating to give rise to other mesodermal derivatives such as cardiac cells (for example, cardiomyocytes) and/or smooth muscle cells.

Mammalian Hemangioblast Cell Markers

As described above, the hemangio-colony forming cells lack certain features characteristic of mature endothelial or hematopoietic cells. These hemangio-colony forming cells or hemangioblasts, however, may be identified by various markers such as, for example, CD71+, GATA-1 and GATA-2 proteins, CXCR-4, and TPO and EPO receptors. In additional embodiments, the hemangioblasts express LMO-2. Hemangioblasts may additionally be characterized by the absence or low expression of other markers. Accordingly, hemangioblasts may be CD34– CD31–, and KDR–. In further embodiments, the hemangioblasts may be CD34–, CD31–, KDR–, and CD133–.

Accordingly, in certain embodiments, the hemangioblasts generated and expanded by the methods of present invention are characterized by the presence or absence of any one or more of the markers listed in Table 2 of WO2007/120811, incorporated herein by reference in its entirety. For example, the hemangioblasts may test negative for expression of any one or more of the markers listed in Table 2 that is denoted as "–" under "BL-CFC". Accordingly, in some embodiments, the hemangioblasts may be negative for CD34 expression. The cells may additionally or alternatively be negative for CD31, CD133, and/or KDR expression. In further embodiments, the hemangioblasts may express any of the markers denoted in Table 2 with "+". For example, the cells may express one or more of the markers LMO-2 and GATA-2. Expression of a marker may be assessed by any method, such as, for example, immunohistochemistry or immunoblotting to test for protein expression, or mRNA analysis to test for expression at the RNA level.

Deriving Hemangioblast Lineage Cells

The methods and cell preparations of the present invention also relate to hemangioblast derivative cells. Human hemangioblasts generated and expanded by this invention and mammalian hemangioblasts expanded by the methods of the invention may be differentiated in vitro to obtain hematopoietic cells (including hematopoietic stem cells (HSCs)) or endothelial cells, as well as cells that are further differentiated in these two lineages. These cells may subsequently be used in the therapeutic and commercial applications described below.

In certain embodiments, hematopoietic cells are derived by growing the hemangioblasts in serum-free BL-CFU for 3-10 days. In other embodiments, single-cell suspensions of hES-derived BL-CFC cells are grown for 10-14 days. Maintaining serum-free conditions is optimal insofar as serum-free conditions facilitate scale-up production and compliance with regulatory guidelines as well as reduce cost. Hemangioblasts of the present invention may also be grown in serum-free Hem-culture (Bhatia et al. 1997 *J Exp Med* (186): 619-624), which sustains human hematopoietic stem cells and comprises BSA (e.g., 1% BSA), insulin (e.g., 5 µg/ml human insulin), transferrin media or transferrin (e.g., 100 µg/ml human transferrin), L-glutamine, beta-mercaptoethanol (e.g., $10^{-4}$ M), and growth factors. The growth factors may comprise SCF (e.g., 300 ng/ml), granulocytic-colony-stimulating factor (G-CSF) (e.g., 50 ng/ml), Flt-3 (e.g., 300 ng/ml), IL-3 (e.g., 10 ng/ml), and IL-6 (e.g., 10 ng/ml). Other factors useful for obtaining hematopoietic cells from hemangioblasts include thrombopoietin (TPO) and VEGF (see, for example, Wang et al. 2005 *Ann NY Aced Sci* (1044): 29-40) and BMP-4. The hemangioblasts may also be grown in serum-free methylcellulose medium supplemented with a multilineage hematopoietic growth factor cocktail. Thus, the hemangioblasts may be grown in methylcellulose in Iscove modified Dulbecco medium (IMDM) comprising BSA, saturated human transferrin, human LDL, supplemented with early acting growth factors (e.g., c-kit ligand, flt3 ligand), multilineage growth factors (e.g., IL-3, granulocyte macrophage-CSF (GM-CSF)), and unilineage growth factors (e.g., G-CSF, EPO, TPO)), VEGF, and bFGF. Alternatively, the hemangioblasts may be grown in medium comprising unilineage growth factors to support the growth of one type of hematopoietic cell (e.g., red blood cells, macrophages, or granulocytes).

In one embodiment, hemangioblast colonies are resuspended in Stemline I media. Cells are then mixed with 1 ml of serum-free hematopoietic CFU media (H4436, Stem Cell Technologies™) plus 1.5 µg/ml of tPTD-HoxB4 and 0.5% EX-CYTE (Serologicals Proteins Inc.™). The cell mixtures are then plated on cell culture untreated plates and incubated at 37° C. for 10-14 days. Hematopoietic CFUs arising following 10-14 days after initial plating may be characterized morphologically, such as by staining with Wright-Giemsa dye.

Hematopoietic cells may also be derived from the hemangioblast using other conditions known in the art (e.g., in media comprising IMDM, 30% fetal calf serum (FCS), 1% bovine serum albumin (BSA), $10^{-4}$ M beta-mercaptoethanol, and 2 mM L-glutamine). Further, in other embodiments basic fibroblast growth factor may be used to promote both BL-CFC frequency within EBs and promote hematopoietic differentiation (Faloon et al. 2000 *Development* (127): 1931-1941). In yet other embodiments, the growth factor hemangiopoietin (HAPO) is used to promote growth and hematopoietic differentiation of the hemangioblasts (Liu et al. 2004 *Blood* (103): 4449-4456). The differentiation into hematopoietic cells may be assessed by CD45 status (CD45+) and the CFU assay, for example.

To form hematopoietic cells, human hemangioblasts may be grown for 3-10 days, or optionally for longer periods of time (e.g., 10-14 days) in CFU-medium. Human hemangioblasts of the present invention are able to form CFUs comprising granulocytes, erythrocytes, macrophages, and megakaryocytes (CFU-GEMM/mix) as well as colony forming units containing only one of the latter cell types (e.g., CFU-G, CFU-E, CFU-M, and CFU-GM). In certain embodiments, single-cell suspensions of hES-derived BL-CFC cells are grown for 10-14 days to derive hematopoietic cells such as, for example, erythroid, myeloid, macrophage, and multilineage hematopoietic cells.

Other aspects of the invention relate to endothelial cells derived from the human hemangioblasts obtained and expanded or mammalian hemangioblasts expanded by the methods described herein. The hemangioblasts may be grown in conditions favorable to endothelial maturation.

In certain embodiments of the present invention, to obtain endothelial cells, hemangioblasts are first plated onto a fibronectin-coated surface and following 3-5 days (or in other embodiments 3-7 days), are replated onto a thick layer of Matrigel to support differentiation into endothelial cells. These conditions maintain the serum-free conditions established during hemangioblast development. Alternatively, hemangioblasts may be grown in media known to support differentiation into endothelial cells. Such conditions include, for example, Endo-culture comprising 20% fetal bovine serum (FBS), 50 ng/ml endothelial cell growth supplement (i.e., pituitary extracts), 10 IU/ml heparin, and 5 ng/ml human VEGF-$A_{165}$ (Terramani et al. 2000 *In vitro Cell Dev Biol Anim* (36): 125-132). Other conditions known in the art include medium supplemented with 25% FCS/horse serum, and in some embodiments heparin (e.g., 10 U/ml), insulin like growth factor (IGF1) (e.g., 2 ng), and EC growth supplement (ECGS, e.g., 100 µg). The growth factors VEGF and EGF may also be used in combination with HAPO to support endothelial differentiation (Liu et al., 2004). The hemangioblasts may also be seeded onto dishes coated with collagen and fibronectin, for example, to promote differentiation into endothelial cells. Cells may be analyzed for von Willebrand factor (vWF) and endothelial nitric oxide synthase (eNOS) and the ability to form an endothelial network in vitro.

Accordingly, to form endothelial cells, hemangioblast colonies derived by the methods described above are picked and replated onto fibronectin-coated culture plates optimized for the first step towards endothelial differentiation. The cells may be plated in EGM-2 or EGM-2MV complete media (Cambrex™). Following 3 to 5 days, and in alternative embodiments 3 to 7 days, the cells are re-plated on a surface that supports endothelial differentiation, such as on a layer of Matrigel. Following 16-24 hours of incubation, the formation of branched tube-cords suggests typical endothelial cell behavior. Endothelial-specific assays such as LDL-uptake may also be used to confirm that these cells are of endothelial nature.

In other aspects of the invention, human hemangioblasts generated and expanded by this invention and mammalian hemangioblasts expanded by the methods of the invention may be differentiated in vitro to obtain other cells, as well as cells that are further differentiated from these cell lineages. Such additional cell lineages may be derived from the hemangioblasts generated and expanded by this invention and mammalian hemangioblasts expanded by the methods of the invention because the hemangioblast cells may have an even greater degree of developmental potential beyond differentiating into hematopoietic and endothelial cells.

Non-Engrafting Hemangio Cells

The present invention provides a novel cell population that shares some characteristics of previously identified hemangioblasts and hemangio-colony forming cells. However, the novel cell population described herein is distinct in that it does not engraft into the bone marrow when administered to immunodeficient animals. This novel progenitor cell population is useful for the study of basic developmental and stem cell biology, is useful to generate partially and terminally differentiated cell type in vitro and in vivo, and is useful for the development of therapeutics. Additionally, these cells can be used in screening assays to identify, for example, (i) factors or conditions that promote the expansion of non-engrafting hemangio cells and (ii) factors or conditions that promote the generation of one or more differentiated cell type from non-engrafting hemangio cells. Identified factors and conditions can be used in the production of cell-based and cell free therapies, in the production of mediums and formulations, and in the study of developmental and stem cell biology.

Overview

The present invention provides non-engrafting hemangio cells, compositions and preparations comprising non-engrafting hemangio cells, methods of producing and expanding non-engrafting hemangio cells, methods of producing differentiated cell types from non-engrafting hemangio cells, and methods of using non-engrafting hemangio cells or cells derived there from therapeutically.

The methods described herein can be used to generate human non-engrafting hemangio cells. However, cells can be obtained from other species including, but not limited to, mice, rats, rabbits, cows, dogs, cats, sheep, pigs, and non-human primates.

This invention provides a method for expanding mammalian non-engrafting hemangio cells obtained from any source, including ES cells, blastocysts or blastomeres, cord blood from placenta or umbilical tissue, peripheral blood, bone marrow, or other tissue or by any other means known in the art. In certain embodiments, human non-engrafting hemangio cells are generated from embryonic stem cells or other pluripotent stem cells. By way of example, human non-engrafting hemangio cells can be generated from embryonic stem cells, as well as from iPS cells. In other embodiments, non-engrafting hemangio cells are generated from human embryo-derived cells. Human embryo-derived cells may be a substantially homogeneous population of cells, a heterogeneous population of cells, or all or a portion of an embryonic tissue. As an example of embryo-derived cells that can be used in the methods of the present invention, human non-engrafting hemangio cells can be generated from human embryonic stem cells. Such embryonic stem cells include embryonic stem cells derived from or using, for example, blastocysts, plated ICMs, one or more blastomeres, or other portions of a pre-implantation-stage embryo or embryo-like structure, regardless of whether produced by fertilization, somatic cell nuclear transfer (SCNT), parthenogenesis, androgenesis, or other sexual or asexual means. In certain embodiments, non-engrafting hemangio cells are generated from pluripotent stem cells. Exemplary pluripotent stem cells include, but are not limited to, embryonic stem cells and iPS cells. In certain embodiments, human non-engrafting hemangio cells are generated from non-pluripotent cells. Non-pluripotent cells may include somatic cells, such as cells derived from skin, bone, blood, connective tissue, heart, kidney, lung, liver, or any other internal organ. In certain embodiments, the non-pluripotent cells may be cells derived from connective tissue, such as fibroblasts. In certain embodiments, the non-pluripotent cells are cells derived from an adult tissue.

In certain embodiments, non-engrafting hemangio cells can be further differentiated to hematopoietic stem cells and/or hematopoietic cell types including, but not limited to, platelets and red blood cells. Such cells may be used in transfusions or in other therapies. Although such cells have numerous uses, a particularly important use would be in improving the availability of blood for transfusions. In certain embodiments, the invention provides red blood cells differentiated from non-engrafting hemangio cells. Such differentiated red blood cells could be used for transfusions.

Further aspects of the invention relate to methods of generating differentiated hematopoietic cells from non-engrafting hemangio cells for use in blood transfusions for those in need thereof. In certain embodiments, differentiated hematopoietic cells are transfused to treat trauma, blood loss during surgery, blood diseases such as anemia, Sickle cell anemia, or hemolytic diseases, or malignant disease. In certain embodiments, red blood cells are transfused to treat trauma, blood loss during surgery, or blood diseases such as anemia, Sickle cell anemia, or hemolytic disease. In certain embodiments, a mixed population of red blood cells are transfused. It should be noted that many differentiated hematopoietic cell types, particularly red blood cells, typically exist in vivo as a mixed population. Specifically, circulating red blood cells of varying levels of age and differentiation are found in vivo. Additionally, red blood cells mature over time so as to express less fetal hemoglobin and more adult hemoglobin. The present invention contemplates transfusion of either purified populations of red blood cells or of a mixed population of red blood cells having varying levels of age and levels of differentiation. In particular embodiments, the invention contemplates transfusion of red blood cells expressing fetal hemoglobin (hemoglobin F). Transfusion of red blood cells that express fetal hemoglobin may be especially useful in the treatment of Sickle cell anemia. The ability to generate large numbers of cells for transfusion will alleviate the chronic shortage of blood experienced in blood banks and hospitals across the country.

In certain embodiments, the methods of the invention allow for the production of universal cells for transfusion. Specifically, red blood cells that are type O and Rh— can be readily generated and will serve as a universal blood source for transfusion. In certain embodiments, the red blood cells produced from the methods of the application are functional. In certain embodiments, the red blood cells express hemoglobin F prior to transfusion. In certain embodiments, the red blood cells carry oxygen. In certain embodiments, the red blood cells have a lifespan equal to naturally derived red blood cells. In certain embodiments, the red blood cells have a lifespan that is 75% of that of naturally derived red blood cells. In certain embodiments, the red blood cells have a lifespan that is 50% of that of naturally derived red blood cells. In certain embodiments, the red blood cells have a lifespan that is 25% of that of naturally derived red blood cells.

In certain embodiments, non-engrafting hemangio cells may have a greater developmental potential, and may differentiate to produce endothelial cell types, smooth muscle cell types, or cardiac cell types.

The methods of this invention allow for the in vitro expansion of non-engrafting hemangio cells to large quantities useful for a variety of commercial and clinical applications. Expansion of non-engrafting hemangio cells in vitro refers to the proliferation of non-engrafting hemangio cells. While the methods of the invention enable the expansion of human non-engrafting hemangio cells to reach commercially useful quantities, the present invention also relates to large numbers of non-engrafting hemangio cells and to cell preparations comprising large numbers of human non-engrafting hemangio cells (for example, at least 10,000, 100,000, or 500,000 cells). In certain embodiments, the cell preparations comprise at least $1 \times 10^6$ cells. In other embodiments, the cell preparations comprise at least $2 \times 10^6$ human non-engrafting hemangio cells and in further embodiments at least $3 \times 10^6$ human non-engrafting hemangio cells. In still other embodiments, the cell preparations comprise at least $4 \times 10^6$ human non-engrafting hemangio cells. Note that these cell preparations may be purified or substantially purified. However, in certain embodiments, suitable cell preparations comprise a mixture of non-engrafting hemangio cells and hemangio-colony forming cells. The mixture may be any ratio, including mixtures comprising a greater proportion of non-engrafting hemangio cells and mixtures comprising a greater proportion of hemangio-colony forming cells.

The present invention relates to a solution, a preparation, or a composition comprising between 10,000 and 4 million or more mammalian (such as human) non-engrafting hemangio cells. The number of non-engrafting hemangio cells in such a solution, a preparation, and a composition may be any number between the range of 10,000 to 4 million, or more. This number could be, for example, 20,000, 50,000, 100,000, 500,000, 1 million, etc.

Similarly, the invention relates to preparations of human non-engrafting hemangio progeny cells (e.g., human hematopoietic cells including human hematopoietic stem cells). The invention further relates to methods of producing, storing, and distributing non-engrafting hemangio cells and/or non-engrafting hemangio cell progeny.

The invention also provides methods and solutions suitable for transfusion into human or animal patients. In particular embodiments, the invention provides methods of making red blood cells and/or platelets, and/or other hematopoietic cell types for transfusion. In certain embodiments, the invention is suitable for use in blood banks and hospitals to provide blood for transfusion following trauma, or in the treatment of a blood-related disease or disorder. In certain embodiments, the invention provides red blood cells that are universal donor cells. In certain embodiments, the red blood cells are functional and express hemoglobin F prior to transfusion.

The invention also provides for human non-engrafting hemangio cells, cell cultures comprising a substantially purified population of human non-engrafting hemangio cells, pharmaceutical preparations comprising human non-engrafting hemangio cells and cryopreserved preparations of the non-engrafting hemangio cells. In certain embodiments, the invention provides for the use of the human non-engrafting hemangio cells in the manufacture of a medicament to treat a condition in a patient in need thereof. Alternatively, the invention provides the use of the cell cultures in the manufacture of a medicament to treat a condition in a patient in need thereof. The invention also provides the use of the pharmaceutical preparations in the manufacture of a medicament to treat a condition in a patient in need thereof.

The non-engrafting hemangio cells can be identified and characterized based on their structural properties and/or function properties. These progenitor cells do not engraft when administered to an immunodeficient host. In certain embodiments, these cells are unique in that they are only loosely adherent to each other (loosely adherent to other non-engrafting hemangio cells). In embodiments in which the cells are loosely adherent, cultures or colonies of non-engrafting hemangio cells can be dissociated to single cells using only mechanical dissociation techniques and without the need for enzymatic dissociation techniques. In certain embodiments, the cells are sufficiently loosely adherent to each other that mechanical dissociation alone, rather than enzymatic dissociation or a combination of mechanical and enzymatic dissociation, is sufficient to disaggregate the cultures or colonies without substantially impairing the viability of the cells. In other words, mechanical dissociation does not require so much force as to cause substantial cell injury or death when compared to that observed subsequent to enzymatic dissociation of cell aggregates.

In certain embodiments, the non-engrafting hemangio cells can be further identified or characterized based on the expression or lack of expression (as assessed at the level of the gene or the level of the protein) of one or more markers. In certain embodiments, the non-engrafting hemangio cells have one or more of the characteristics of human hemangio-colony forming cells. For example, in certain embodiments, non-engrafting hemangio cells can be identified or characterized based on lack of expression of one or more (e.g., the cells can be characterized based on lack of expression of at least one, at least two, at least three or at least four of the following markers) of the following cell surface markers: CD34, KDR, CD133, or CD31. Additionally or alternatively, non-engrafting hemangio cells can be identified or characterized based on expression of GATA2 and/or LMO2.

Human Non-Engrafting Hemangio Cells

In certain aspects, the present invention provides human non-engrafting hemangio cells. These cells are a unique, primitive cell type with a variety of therapeutic and other uses. Furthermore, this cell type provides an important tool for studying development of at least the hematopoietic lineages. As such, the invention contemplates various preparations (including pharmaceutical preparations) and compositions comprising human non-engrafting hemangio cells, as well as preparations (including pharmaceutical preparations) and compositions comprising one or more cell types partially or terminally differentiated from non-engrafting hemangio cells. Without being bound by any particular theory, these cells represent a distinct, somewhat more committed (than hemangio-colony forming cells) stem cell population that retain the ability to generate numerous hematopoietic cell types.

Non-engrafting hemangio cells of the present invention can be identified or characterized based on one or any combination of the structural or functional characteristics described for hemangio-colony forming cells. Note that although these cells can be derived from any of a number of sources, for example, embryonic tissue, prenatal tissue, or perinatal tissue, the term "non-engrafting hemangio cells" applies to cells, regardless of source, that do not engraft and that are capable of differentiating to give rise to at least one hematopoietic cell type, and optionally have one or more of the foregoing structural or functional properties.

To illustrate, human non-engrafting hemangio cells of the present invention do not engraft when administered to a immunodeficient host and have at least one of the following structural characteristics: (a) can differentiate to give rise to at least one hematopoietic cell type; (b) can differentiate to give rise to at least hematopoietic cell types and endothelial cell types; (c) are loosely adherent to each other (to other non-engrafting hemangio cells); (d) do not express CD34 protein; (e) do not express CD31 protein; (f) do not express KDR protein; (g) do not express CD133 protein; (h) express GATA2 protein; (i) express LMO2 protein. In certain embodiments, human non-engrafting hemangio cells have at least two, at least three, at least four, at least five, at least six, at least seven, at least eight, or at least nine of the structural or functional characteristics detailed herein.

As detailed above, one of the interesting properties of human non-engrafting hemangio cells is that they are loosely adherent to each other. Because these cells are only loosely adherent to each other, cultures or colonies of non-engrafting hemangio cells can be dissociated to single cells using only mechanical dissociation techniques and without the need for enzymatic dissociation techniques. The cells are sufficiently loosely adherent to each other that mechanical dissociation alone, rather than enzymatic dissociation or a combination thereof, is sufficient to disaggregate the cultures or colonies without substantially impairing the viability of the cells. In other words, mechanical dissociation does not require so much force as to cause substantial cell injury or death.

This property is not only useful in describing the cells and distinguishing them phenotypically from other cell types, but it also has significant therapeutic implications. For example, relatively large numbers (greater than $1 \times 10^6$ or even greater than $1 \times 10^7$ or even greater than $1 \times 10^8$) of the non-engrafting hemangio cells can be injected into humans or other animals with substantially less risk of causing clots or emboli, or otherwise lodging in the lung. This is a significant advance in cellular therapy. The ability to safely administer relatively large numbers of cells makes cellular therapy practical and possible for the effective treatment of an increasing number of diseases and conditions.

The term "loosely adherent" is described qualitatively above and refers to behavior of the human non-engrafting hemangio cells with respect to each other. Cultures or colonies of non-engrafting hemangio cells can be dissociated to single cells using only mechanical dissociation techniques and without the need for enzymatic dissociation techniques. The cells are sufficiently loosely adherent to each other that mechanical dissociation alone, rather than enzymatic dissociation or a combination thereof, is sufficient to disaggregate the cultures or colonies without substantially impairing the viability of the cells. In other words, mechanical dissociation does not require so much force as to cause substantial cell injury or death.

The term can also be described more quantitatively. For example and in certain embodiments, the term "loosely adherent" is used to refer to cultures or colonies of non-engrafting hemangio cells wherein at least 50% of the cells in the culture can be dissociated to single cells using only mechanical dissociation techniques and without the need for enzymatic dissociation techniques. In other embodiments, the term refers to cultures in which at least 60%, 65%, 70%, or 75% of the cells in the culture can be dissociated to single cells using only mechanical dissociation techniques and without the need for enzymatic dissociation techniques. In still other embodiments, the term refers to cultures in which at least 80%, 85%, 90%, 95%, 96%, 97%, 98%, 99%, or even 100% of the cells in the culture can be dissociated to single cells using only mechanical dissociation techniques and without the need for enzymatic dissociation techniques.

The ability to dissociate the non-engrafting hemangio cells using only mechanical dissociation techniques and without the need for enzymatic dissociation techniques can be further quantitated based on the health and viability of the cells following mechanical dissociation. In other words, if dissociation without enzymatic techniques requires so much mechanical force that a significant number of the cells are damaged or killed, the cells are not loosely adherent, as defined herein. For example and in certain embodiments, the term "loosely adherent" refers to cultures of cells that can be dissociated to single cells using only mechanical dissociation techniques and without the need for enzymatic dissociation techniques, without substantially impairing the health or viability or the cells in comparison to that observed when the same cells are dissociated using enzymatic dissociation techniques. For example, the health or viability of the cells is decreased by less than 15%, 10%, 9%, 8%, 7%, 6%, 5%, 4%, 3%, 2%, or even less than 1% in comparison to that observed when a culture of the same cells are dissociated using enzymatic dissociation techniques.

Exemplary enzymatic dissociation techniques include, but are not limited to, treatment with trypsin, collagenase, or other enzymes that disrupt cell-cell or cell-matrix interactions. Exemplary mechanical dissociation techniques include, but are not limited to, one or more passages through a pipette.

Human non-engrafting hemangio cells according to the present invention are defined structurally and functionally. Such cells can be generated from any of a number of sources including from embryonic tissue, prenatal tissue, perinatal tissue, and even from adult tissue. By way of example, human non-engrafting hemangio cells can be generated from human embryonic stem cells, other embryo-derived cells (blastocysts, blastomeres, ICMs, embryos, trophoblasts/trophectoderm cells, trophoblast stem cells, primordial germ cells, embryonic germ cells, etc.), amniotic fluid, amniotic stem cells, placenta, placental stem cells, and umbilical cord. More generally, non-engrafting hemangio cells can be generated from pluripotent cells, such as embryonic stem cells or pluripotent stem cells. Exemplary pluripotent stem cells include, but are not limited to, embryonic stem cells and induced pluripotent stem cells (iPS cells), Human non-engrafting hemangio cells can also be generated from non-pluripotent cells, such as somatic cells, including but not limited to, cells derived from skin, bone, blood, connective tissue, heart, kidney, lung, liver, or any other internal organ. In certain embodiments, the non-pluripotent cells may be cells derived from connective tissue, such as fibroblasts. In certain embodiments, the non-pluripotent cells are cells derived from an adult tissue.

The invention provides non-engrafting hemangio cells (such as human cells), compositions comprising human non-engrafting hemangio cells, and preparations (including pharmaceutical preparations) comprising human non-engrafting hemangio cells. Certain features of these aspects of the invention are described in detail below. The invention contemplates combinations of any of the following aspects and embodiments of the invention, as well as combinations with the disclosure provided at U.S. application Ser. No. 11/787,262, which is incorporated by reference in its entirety.

As detailed above, hemangio-colony forming cells and/or non-engrafting hemangio cells can be produced from a variety of cells including, but not limited to, pluripotent cells (embryonic stem cells, embryo-derived cells, and induced pluripotent stem cells).

In one aspect, the invention provides a non-engrafting hemangio cells (such as human cells). The cell can differentiate to produce at least one hematopoietic cell types. In certain embodiments, the cell is loosely adherent to other human non-engrafting hemangio cells. In certain embodiments, the cell does not express CD34 protein. In certain other embodiments, the cell does not express one or more of (e.g., the cell does not express at least one, at least two, at least three, or at least four of the following proteins) the following proteins: CD34, CD31, CD133, KDR. In certain other embodiments, the cell does express GATA2 and/or LMO2 protein. In certain other embodiments, the cell shares one or more than one (2, 3, 4, 5, 6, 7, 8, 9, 10) of the functional or structural characteristics of human hemangio colony forming cells.

In another aspect, the invention provides a cell culture comprising a substantially purified population of non-engrafting hemangio cells (such as human cells). The cells can differentiate to produce at least hematopoietic cell types. In certain embodiments, the cells are loosely adherent to each other. In certain embodiments, the cell does not express CD34 protein. In certain other embodiments, the cell does not express one or more of (e.g., the cell does not express at least one, at least two, at least three, or at least four of the following proteins) the following proteins: CD34, CD31, CD133, KDR. In certain other embodiments, the cell does express GATA2 and/or LMO2 protein. In certain other embodiments, the cell shares one or more than one (2, 3, 4, 5, 6, 7, 8, 9, 10) of the functional or structural characteristics of human hemangio colony forming cells.

In another aspect, the invention provides a cell culture comprising non-engrafting hemangio cells differentiated from embryonic tissue. In certain embodiments, the invention provides a cell culture comprising non-engrafting hemangio cells differentiated from pluripotent cells (pluripotent stem cells). In certain embodiments, the non-engrafting hemangio cells are loosely adherent to each other. In certain embodiments, the cells can differentiate to produce at least hematopoietic cell types, and the cells are loosely adherent to each other. In certain embodiments, the cell does not express CD34 protein. In certain other embodiments, the cell does not express one or more of (e.g., the cell does not express at least one, at least two, at least three, or at least four of the following proteins) the following proteins: CD34, CD31, CD133, KDR. In certain other embodiments, the cell does express GATA2 and/or LMO2 protein. In certain other embodiments, the cell shares one or more than one (2, 3, 4, 5, 6, 7, 8, 9, 10) of the functional or structural characteristics of human hemangio colony forming cells.

In another aspect, the invention provides a cell culture comprising human non-engrafting hemangio cells, which cells can differentiate to produce at least hematopoietic cell types. In certain embodiments, the cells are loosely adherent to each other. In certain embodiments, the cell does not express CD34 protein. In certain other embodiments, the cell does not express one or more of (e.g., the cell does not express at least one, at least two, at least three, or at least four of the following proteins) the following proteins: CD34, CD31, CD133, KDR. In certain other embodiments, the cell does express GATA2 and/or LMO2 protein. In certain other embodiments, the cell shares one or more than one (2, 3, 4, 5, 6, 7, 8, 9, 10) of the functional or structural characteristics of human hemangio colony forming cells.

In another aspect, the invention provides a pharmaceutical preparation comprising human non-engrafting hemangio cells, which cells can differentiate to produce at least hematopoietic cell types. In certain embodiments, the non-engrafting hemangio cells are loosely adherent to each other. In certain embodiments, the cell does not express CD34 protein. In certain other embodiments, the cell does not express one or more of (e.g., the cell does not express at least one, at least two, at least three, or at least four of the following proteins) the following proteins: CD34, CD31, CD133, KDR. In certain other embodiments, the cell does express GATA2 and/or LMO2 protein. In certain other embodiments, the cell shares one or more than one (2, 3, 4, 5, 6, 7, 8, 9, 10) of the functional or structural characteristics of human hemangio colony forming cells. The pharmaceutical preparation can be prepared using any pharmaceutically acceptable carrier or excipient.

In another aspect, the invention provides a pharmaceutical preparation comprising human non-engrafting hemangio cells. The pharmaceutical preparation can be prepared using any pharmaceutically acceptable carrier or excipient.

In certain embodiments of any of the foregoing, the composition or pharmaceutical preparation comprises at least $1 \times 10^5$ human non-engrafting hemangio cells. In certain other embodiment, of any of the foregoing, the composition or pharmaceutical preparation comprises at least $1 \times 10^6$, at least $5 \times 10^6$, at least $1 \times 10^7$, or greater than $1 \times 10^7$ human non-engrafting hemangio cells. In certain embodiments, the preparation is a purified or substantially purified preparation. In other embodiments, the preparation comprises a mixture of non-engrafting hemangio cells and other cell types. For example, a mixture of non-engrafting hemangio cells and hemangio-colony forming cells.

Additional cells, compositions, and preparations include cells partially or terminally differentiated from human non-engrafting hemangio cells. For example, the invention contemplates compositions and preparations comprising one or more hematopoietic and/or endothelial cell type differentiated from a non-engrafting hemangio cells. Exemplary hematopoietic cell types include hematopoietic stem cells, platelets, RBCs, lymphocytes, megakaryocytes, and the like. By way of further examples, the invention contemplates compositions and preparations comprising one or more other cell type, such as one or more partially or terminally differentiated mesodermal cell type, differentiated from non-engrafting hemangio cells.

In certain embodiments of any of the foregoing, the invention provides a cryopreserved preparation of human non-engrafting hemangio cells or cells partially or terminally differentiated therefrom.

In certain embodiments of any of the foregoing, the invention provides for the therapeutic use of human non-engrafting hemangio cells, or compositions or preparations of human non-engrafting hemangio cells. Such cells and preparations can be used in the treatment of any of the conditions or diseases detailed throughout the specification, as well as in the blood banking industry. Furthermore, cells differentiated from human non-engrafting hemangio cells, or compositions or preparations of human non-engrafting hemangio cells, can be used therapeutically in the treatment of any of the conditions or diseases detailed throughout the specification.

The human non-engrafting hemangio cells of the invention can be used therapeutically. Additionally or alternatively, human non-engrafting hemangio cells can be used to study development of endothelial and hematopoietic lineages or in screening assays to identify factors that can be used, for example, to (i) maintain human non-engrafting hemangio cells or (ii) to promote differentiation of human non-engrafting hemangio cells to one or more partially or terminally differentiated cell types. Furthermore, human non-engrafting hemangio cells can be used to generate one or more partially or terminally differentiated cell types for in vitro or in vivo use.

The human non-engrafting hemangio cells of the invention can be used in any of the methods or application described in the present application including, but not limited to, in the treatment of any of the diseases or conditions described herein. Exemplary diseases and conditions are further discussed in U.S. application Ser. No. 11/787,262, which is incorporated by reference in its entirety. Further, human hemangio-colony forming cells and non-engrafting hemangio cells can be used to produce differentiated hematopoietic cell types, including functional red blood cells.

Cell Preparations Comprising Hemangioblasts Expanded In Vitro

In certain embodiments of the present invention, mammalian (including human) non-engrafting hemangio cells are expanded to reach commercial quantities and are used in various therapeutic and clinical applications. In particular embodiments, non-engrafting hemangio cells are expanded to reach cell numbers on the order of 10,000 to 4 million (or more). These cell numbers may be reached within 3-4 days of starting the initial preparations. Accordingly, the present invention relates to preparations comprising large numbers of non-engrafting hemangio cells, said preparations comprising at least 10,000, 50,000, 100,000, 500,000, a million, 2 million, 3 million or 4 million cells.

This invention also provides for a solution, a composition, and a preparation comprising large numbers of non-engrafting hemangio cells, said solution, said composition, and said preparation comprising at least 10,000, 50,000, 100,000, 500,000, a million, 2 million, 3 million or 4 million cells. The non-engrafting hemangio cells could be human. The solutions can be purified, substantially purified, or mixtures with other progenitor cells types including, but not limited to hemangio-colony forming cells.

Other aspects of the present invention relate to differentiating the non-engrafting hemangio cells obtained by the methods disclosed herein into hematopoietic or endothelial cell lineages, or both, that are subsequently used in clinical applications. Thus, the present invention also relates to cell preparations comprising large numbers of partially or terminally differentiated cell types.

Compositions and preparations comprising large numbers (e.g., thousands or millions) of non-engrafting hemangio cells may be obtained by expanding non-engrafting hemangio cells that are obtained as described above. Accordingly, the invention pertains to compositions and preparations comprising large numbers of non-engrafting hemangio cells achieved by expanding ES cells (such as human ES cells) or non-engrafting hemangio cells obtained from cord blood, peripheral blood or bone marrow. Further, as the methods of expansion may be applied to non-engrafting hemangio cells of mouse, rat, bovine, or non-human primate origin, for example, the present invention also relates to compositions and preparations comprising large numbers of non-engrafting hemangio cells of other species in addition to human. The non-engrafting hemangio cells to be expanded by the methods of this invention may be bi-potential, i.e., can differentiate into either endothelial cells or hematopoietic stem cells. In certain embodiments, the human non-engrafting hemangio cells generated and expanded from human ES cells are bi-potential. Non-engrafting hemangio cells are capable of differentiating to give rise to at least hematopoietic cell types. Non-engrafting hemangio cells are, in certain embodiments, bi-potential and capable of differentiating to give rise to at least hematopoietic cell types and endothelial cell types. As such, non-engrafting hemangio cells of the present invention are at least uni-potential, and may be bi-potential. Additionally however, non-engrafting hemangio cells may have a greater degree of developmental potential and can, in certain embodiments, differentiate to give rise to cell types of other lineages. In certain embodiments, the non-engrafting hemangio cells are capable of differentiating to give rise to other mesodermal derivatives such as cardiac cells (for example, cardiomyocytes) and/or smooth muscle cells.

In addition, the non-engrafting hemangio cells can be used in screening assays to identify agents that, for example, (i) promote differentiation of the cells to one or more hematopoietic cell type or (ii) promote proliferation and/or survival of the cells to facilitate cell banking and storage. The non-engrafting hemangio cells can also be used to study basic developmental biology or can be compared to hemangio-colony forming cells to ascertain the developmental differences between the two related stem cell populations.

Clinical and Commercial Embodiments of Human Hemangioblasts, Non-Engrafting Hemangio Cells, Hemangioblast Lineage Cells and Non-Engrafting Hemangio Lineage Cells Cell-Based Therapies While human hemangioblast cells and non-engrafting hemangio cells have the potential to differentiate in vivo into either hematopoietic or endothelial cells, they can be used in cell-based treatments in which either of these two cell types are needed or would improve treatment. Further, a patient may be treated with any therapy or treatment comprising hemangioblast lineage cells or and non-engrafting hemangio lineage cells (i.e., hematopoietic cells and/or endothelial cells). The following section describes methods of using the human hemangioblasts and non-engrafting hemangio cells of this invention generated and expanded by the methods of this invention, or expanded by the methods of this invention.

In certain embodiments of the present invention, treatments to increase or treat hematopoietic cells and treatments for increasing blood vessel growth and/or facilitating blood vessel repair are contemplated. Accordingly, in certain aspects, the present invention relates to methods and compositions for treating a patient in need of hematopoietic cells or blood vessel growth or repair. The hemangioblasts or non-engrafting hemangio cells may be injected into the blood vessel of a subject or be administered to the blood vessel of a subject through operation. The patient or the subject may be human.

In certain embodiments of the present invention, human hemangioblast cells or non-engrafting hemangio cells are used in transplantation, where HSC transplantation would otherwise be used. Such transplantation may be used, for example, in hematopoietic reconstitution for the treatment of patients with acute or chronic leukemia, aplastic anemia and various immunodeficiency syndromes, as well as various non-hematological malignancies and auto-immune disorders, and to rescue patients from treatment-induced aplasia following high-dose chemotherapy and/or radiotherapy. Such transplantation may be achieved in vivo or ex vivo (such as in bone marrow transplant).

In other embodiments of the invention, human hemangioblast cells or non-engrafting hemangio cells are used to treat patients in need of hematopoietic reconstitution or hematopoietic treatment. Such patients in include, for example, patients with thalassemias, sickle cell anemia, aplastic anemia (also called hypoplastic anemia), cytopenia, marrow hypoplasia, platelet deficiency, hematopoietic malignancies such as leukemias, paroxysmal nocturnal hemoglobinuria (PNH), and ADA (e.g., deaminase (ADA)-deficient severe combined immunodeficiency (SCID)).

Particular embodiments of the present invention therefore relate to methods of treating a patient in need of hematopoietic reconstitution or hematopoietic treatment using the hemangioblasts of the invention. Accordingly, the invention relates to methods of treating a patient in need of hematopoietic reconstitution or treatment comprising selecting a patient in need thereof, generating and expanding or expanding human hemangioblasts or non-engrafting hemangio cells according to the methods of the present invention, and administering the human hemangioblasts or the non-engrafting hemangio cells into the patient. Alternatively, the method may comprise differentiating the generated and expanded or expanded human hemangioblasts or non-engrafting hemangio cells into human hematopoietic cells and subsequently administering the hematopoietic cells to the patient.

Alternative embodiments include methods in which human hemangioblasts or non-engrafting hemangio cells are produced on a large scale and stored prior to the selection of a patient in need thereof. Thus, other embodiments of the invention relate to methods of treating a patient in need of hematopoietic reconstitution or treatment comprising selecting a patient in need thereof, placing an order for human hemangioblasts or non-engrafting hemangio cells already isolated and expanded according to the methods described above, and administering said human hemangioblasts or non-engrafting hemangio cells to the patient. Likewise, the method may comprise differentiating said human hemangioblasts or non-engrafting hemangio cells into human hematopoietic cells and administering said hematopoietic cells to the patient. In additional embodiments, hemangioblasts or non-engrafting hemangio cells hemizygous or homozygous for at least one MHC allele are grown, optionally grown to commercial quantities, and optionally stored by a business entity. When a patient presents a need for such cells, hemangioblast lineage cells or non-engrafting hemangio lineage cells, a clinician or hospital will place an order with the business for such cells.

Because the human hemangioblast cells and non-engrafting hemangio cells of the invention will proliferate and differentiate into endothelial cells under an angiogenic microenvironment, the human hemangioblast cells may be used in a therapeutic manner to provide new blood vessels or to induce repair of damaged blood vessels at a site of injury in a patient. Thus in certain aspects, the present invention relates to methods of promoting new blood vessel growth or repairing injured vasculature. The human hemangioblasts or non-engrafting hemangio cells of the present invention may be used to treat endothelial injury, such as myocardium infarction, stroke and ischemic brain, ischemic limbs and skin wounds including ischemic limbs and wounds that occur in diabetic animals or patients, and ischemic reperfusion injury in the retina. Other ischemic conditions that may be treated with the hemangioblasts or non-engrafting hemangio cells of the present invention include renal ischemia, pulmonary ischemia, and ischemic cardiomyopathy. Hemangioblasts may also be used to help repair injured blood vessels following balloon angioplasty or deployment of an endovascular stent. Hemangioblasts or non-engrafting hemangio cells may additionally be used in tissue grafting, surgery and following radiation injury. Further, the hemangioblasts or non-engrafting hemangio cells may be used to treat and/or prevent progression of atherosclerosis as well as to repair endothelial cell damage that occurs in systemic sclerosis and Raynaud's phenomenon (RP) (Blann et al. 1993 *J Rheumatol.* (20):1325-30).

Accordingly, the invention provides various methods involved in providing blood vessel growth or repair to a patient in need thereof. In one embodiment, the invention provides for a method for inducing formation of new blood vessels in an ischemic tissue in a patient in need thereof, comprising administering to said patient an effective amount of the purified preparation of human hemangioblast cells or non-engrafting hemangio cells described above to induce new blood vessel formation in said ischemic tissue. Thus certain aspects of the present invention provide a method of enhancing blood vessel formation in a patient in need thereof, comprising selecting the patient in need thereof, isolating human hemangioblast cells or non-engrafting hemangio cells as described above, and administering the hemangioblast cells or non-engrafting hemangio cells to the patient. In yet another aspect, the present invention provides a method for treating an injured blood vessel in a patient in need thereof, comprising selecting the patient in need thereof, expanding or generating and expanding human hemangioblast cells or non-engrafting hemangio cells as described above, and administering the hemangioblast cells or non-engrafting hemangio cells to the patient. In addition to the aforementioned embodiments, the hemangioblasts or non-engrafting hemangio cells may be produced on a large scale and stored prior to the selection of patient in need of hemangioblasts. In further embodiments, hemangioblasts hemizygous or homozygous for at least one MHC allele are grown, optionally grown to commercial quantities, and optionally stored before a patient is selected for hemangioblast or non-engrafting hemangio cell treatment. Any of the aforementioned hemangioblasts, non-engrafting hemangio cells, or cell preparations of these cells may be administered directly into the circulation (intravenously). In certain embodiments (e.g., where vascular repair is necessary in the eye, such as in the treatment of ischemia/reperfusion injury to the retina), the hemangioblast cells, non-engrafting hemangio cells, or cell preparations of these cells may be administered by intra-vitreous injection.

Administration of the solutions or preparations of hemangioblasts, non-engrafting hemangio cells, and derivative cells thereof may be accomplished by any route and may be determined on a case by case basis. Also, an effective amount to be administered of these solutions or preparations of hemangioblasts or derivative cells thereof is an amount that is therapeutically effective and may be determined on a case by case basis.

In further aspects, hemangioblast lineage cells or non-engrafting hemangio lineage cells are used in therapeutic applications, including in the treatment of the indications described above, for example. Accordingly, hemangioblasts or non-engrafting hemangio cells generated and expanded or expanded by the methods described herein are differentiated in vitro first to obtain hematopoietic and/or endothelial cells, and then to obtain cells that are further differentiated in these two lineages. These cells may be subsequently administered to a subject or patient to treat hematopoietic conditions or for hematopoietic reconstitution, or for the treatment of ischemia or vascular injury, for example.

HSCs derived from the human hemangioblasts or non-engrafting hemangio cells obtained by the methods disclosed herein are grown further to expand the HSCs and/or to derive other hematopoietic lineage cell types. Certain aspects of the present invention relate to the use of HSCs derived from the hemangioblasts or non-engrafting hemangio cells in transplantation. In additional embodiments, differentiated hematopoietic cells (such as, for example, granulocytes, erythrocytes, myeloid cells, megakaryocytes, platelets, macrophages, mast cells and neutrophils (Wiles and Keller 1991 Development (111): 259)) are used in various treatments such as transfusion therapy or for the treatment of infections. Accordingly, other embodiments of the present invention relate to methods of treating a patient in need of hematopoietic reconstitution or treatment using the HSCs or hematopoietic lineage cells derived from hemangioblasts of the invention.

In certain aspects, therefore, the present invention relates to methods of treating a patient in need of hematopoietic cells or treatment comprising selecting a patient in need thereof, expanding or isolating and expanding human hemangioblasts or non-engrafting hemangio cells according to the methods of the present invention, differentiating said hemangioblast cells or non-engrafting hemangio cells into hematopoietic stem cells and/or mature hematopoietic cells, and administering the hematopoietic cells to the patient.

In other aspects of the invention, the hemangioblasts or non-engrafting hemangio cells are grown to give rise to endothelial cells according to the methods disclosed herein. The endothelial may subsequently be used to provide new blood vessels or to induce repair of damaged blood vessels at a site of injury in a patient. Thus in certain aspects, the present invention relates to methods of promoting new blood vessel growth or repairing injured vasculature in which endothelial cells derived from hemangioblasts or non-engrafting hemangio cells are used as a therapy. The endothelial cells may be used to treat endothelial injury, such as myocardium infarction and pulmonary ischemia, stroke and ischemic brain, ischemic limbs and skin wounds including ischemic limbs and wounds that occur in diabetic animals or patients, ischemic reperfusion injury in the retina, renal ischemia. The endothelial cells may also be used to help repair injured blood vessels following balloon angioplasty or deployment of an endovascular stent as well as in grafting, surgery and following radiation injury. Further, the endothelial cells may be used to treat and/or prevent progression of atherosclerosis as well as to repair endothelial cell damage that occurs in systemic sclerosis and Raynaud's phenomenon.

The endothelial cell may be further differentiated and those cells, as appropriate, may be used in treating one or more of the "endothelial cell" disease or conditions, such as those listed in the preceding paragraph.

Accordingly, certain aspects of the invention relate to methods of treating a patient with endothelial or vascular injury or in need of blood vessel growth or repair comprising selecting a patient in need thereof, expanding or isolating and expanding human hemangioblasts or non-engrafting hemangio cells according to the methods of the present invention, differentiating said hemangioblast cells or non-engrafting hemangio cells into endothelial cells, and administering the endothelial cells to the patient.

Blood Banking

Another aspect of the present invention provides methods of producing hematopoietic cells suitable for transfusion. Although such cells and methods have numerous uses, a particularly important use would be in improving the availability of blood for transfusions. In certain preferred embodiments, the invention provides red blood cells differentiated from hemangioblasts/hemangio-colony forming units or non-engrafting hemangio cells. Such differentiated red blood cells could be used for transfusions.

Further aspects of the invention relate to methods of generating differentiated hematopoietic cells from hemangioblasts/hemangio-colony forming units or non-engrafting hemangio cells for use in blood transfusions for those in need thereof. In certain embodiments, differentiated hematopoietic cells are transfused to treat trauma, blood loss during surgery, blood diseases such as anemia, Sickle cell anemia, or hemolytic diseases, or malignant disease. In certain embodiments, red blood cells are transfused to treat trauma, blood loss during surgery, or blood diseases such as anemia, Sickle cell anemia, or hemolytic disease. In certain embodiments, platelets are transfused to treat congenital platelet disorders or malignant disease. In certain embodiments, a mixed population of red blood cells and platelets are transfused.

It should be noted that many differentiated hematopoietic cell types, particularly red blood cells, typically exist in vivo as a mixed population. Specifically, circulating red blood cells of varying levels of age and differentiation are found in vivo. Additionally, red blood cells mature over time so as to express less fetal hemoglobulin and more adult hemoglobin. The present invention contemplates transfusion of either purified populations of red blood cells or of a mixed population of red blood cells having varying levels of age and levels of differentiation. In particular embodiments, the invention contemplates transfusion of red blood cells expressing fetal hemoglobin (hemoglobin F).

This invention provides a method for producing differentiated hematopoietic cells from human hemangio-colony forming cells and non-engrafting hemangio cells in vitro, said method comprising the steps of:

(a) providing human hemangio-colony forming cells or non-engrafting hemangio cells; and b) differentiating said hemangio-colony forming cells or non-engrafting hemangio cells into differentiated hematopoietic cells.

This invention also provides a method for performing blood transfusions using hematopoietic cells that were differentiated in vitro from human hemangio-colony forming cells or non-engrafting hemangio cells, said method comprising the steps of:

(a) providing human hemangio-colony forming cells or non-engrafting hemangio cells;

(b) differentiating said hemangio-colony forming cells or non-engrafting hemangio cells into differentiated hematopoietic cells; and (c) performing blood transfusions with said differentiated hematopoietic cells.

This invention also provides a method for performing blood transfusions using hematopoietic cells that had been differentiated in vitro from human hemangio-colony forming cells, said method comprising the steps of:

(a) culturing a cell culture comprising human embryonic stem cells in serum-free media in the presence of at least one growth factor in an amount sufficient to induce the differentiation of said embryonic stem cells into embryoid bodies;

(b) adding at least one growth factor to said culture comprising embryoid bodies and continuing to culture said culture in serum-free media, wherein said growth factor is in an amount sufficient to expand human hemangio-colony forming cells or non-engrafting hemangio cells in said embryoid bodies culture;

(c) differentiating said hemangio-colony forming cells or non-engrafting hemangio cells into differentiated hematopoietic cells; and (d) performing blood transfusions with said differentiated hematopoietic cells.

In certain embodiments, said stem cells, embryoid bodies and hemangio-colony forming are grown in serum-free media throughout steps (a) and (b) of said method.

This invention also provides a method for performing blood transfusions using hematopoietic cells that had been differentiated in vitro from human hemangio-colony forming cells, said method comprising the steps of:

(a) culturing a cell culture comprising human pluripotent stem cells in serum-free media in the presence of at least one growth factor in an amount sufficient to induce the differentiation of said pluripotent stem cells into embryoid bodies;

(b) adding at least one growth factor to said culture comprising embryoid bodies and continuing to culture said culture in serum-free media, wherein said growth factor is in an amount sufficient to expand human hemangio-colony forming cells or non-engrafting hemangio cells in said embryoid bodies culture;

(c) disaggregating said embryoid bodies into single cells;

(d) adding at least one growth factor to said culture comprising said single cells and continuing to culture said culture in serum-free media, wherein said growth factor is in an amount sufficient to expand human hemangio-colony forming cells or non-engrafting hemangio cells in said culture comprising said single cells;

(e) differentiating said hemangio-colony forming cells or non-engrafting hemangio cells into differentiated hematopoietic cells; and (f) performing blood transfusions with said differentiated hematopoietic cells.

In certain embodiments, said pluripotent stem cells, embryoid bodies, hemangio-colony forming cells, non-engrafting hemangio cells and single cells are grown in serum-free media throughout steps (a)-(d) of said method.

In certain embodiments, the pluripotent stem cell is an embryonic stem cell.

In certain embodiments, the growth factor is a protein that comprises a homeobox protein, or a functional variant or an active fragment thereof. In certain embodiments, the homeobox protein comprises a HOXB4 protein, or a functional variant or an active fragment thereof.

In certain embodiments, the differentiated hematopoietic cells are produced as a single cell type such as red blood cells, platelets, and phagocytes. Note, however, that when a single cell type is produced, the cell type may be heterogeneous in terms of the level of maturity or differentiation of the particular cell type. By way of example, differentiated red blood cells may be heterogeneous in terms of level of maturity and cellular age. Without being bound by theory, such heterogeneity of erythrocytic cells may be beneficial because it mimics the way in which red blood cells are found in vivo.

In certain embodiments, the single cell types are mixed to equal the proportion of differentiated cell types that is found in blood. In certain embodiments, multiple differentiated hematopoietic cell types are produced in the same step. In certain embodiments, the phagocyte is selected from: granulocytes, neutrophils, basophils, eosinophils, lymphocytes or monocytes. In certain embodiments, the hematopoietic cell types are produced in a proportion approximately equal to the proportion of differentiated hematopoietic cell types found in blood, 96% red blood cells, 1% platelets, and 3% phagocytes. In certain embodiments, plasma is added to the differentiated hematopoietic cells before transfusion. In certain embodiments, packed cells, for example packed red blood cells, are transfused in the absence or substantial absence of plasma.

In certain embodiments, the differentiated hematopoietic cells produced from the methods of the application are functional. In certain embodiments, the platelets produced from the methods of the application are functional. In certain embodiments, the phagocytes produced from the methods of the application are functional. In certain embodiments, the red blood cells produced from the methods of the application are functional. In certain embodiments, the red blood cells express hemoglobin F prior to transfusion. In certain embodiments, the red blood cells carry oxygen. In certain embodiments, the red blood cells have a lifespan equal to naturally derived red blood cells. In certain embodiments, the red blood cells have a lifespan that is 75% of that of naturally derived red blood cells. In certain embodiments, the red blood cells have a lifespan that is 50% of that of naturally derived red blood cells. In certain embodiments, the red blood cells have a lifespan that is 25% of that of naturally derived red blood cells.

In certain embodiments, the methods of the application produce $1 \times 10^6$ cells per 100 mm dish. In certain embodiments, $2 \times 10^6$ cells are produced per 100 mm dish. In certain embodiments, $3 \times 10^6$ cells are produced per 100 mm dish. In certain embodiments, $4 \times 10^6$ cells are produced per 100 mm dish. In certain embodiments, $5 \times 10^6$ cells are produced per 100 mm dish. In certain embodiments, $6 \times 10^6$ cells are produced per 100 mm dish. In certain embodiments, $7 \times 10^6$ cells are produced per 100 mm dish. In certain embodiments, $8 \times 10^6$ cells are produced per 100 mm dish. In certain embodiments, $9 \times 10^6$ cells are produced per 100 mm dish. In certain embodiments, $1 \times 10^7$ cells are produced per 100 mm dish. In certain embodiments, $5 \times 10^7$ cells are produced per 100 mm dish. In certain embodiments, $1 \times 10^8$ cells are produced per 100 mm dish.

In certain embodiments, the differentiation step is performed using conditions known to one of skill in the art as discussed above. In certain embodiments, the differentiation step is performed using methods specific to differentiate cells into red blood cells (see WO2005/118780, herein incorporated by reference). In certain embodiments, the differentiation step is performed using methods specific to differentiate cells into platelets. In certain embodiments, the differentiation step is performed using methods specific to differentiate cells into leukocytes.

Differentiation agents which can be used according to the present invention include cytokines such as interferon-alpha A, interferon-alpha A/D, interferon-.beta., interferon-gamma, interferon-gamma-inducible protein-10, interleukin-1, interleukin-2, interleukin-3, interleukin-4, interleukin-5, interleukin-6, interleukin-7, interleukin-8, interleukin-9, interleukin-10, interleukin-1, interleukin-12, interleukin-13, interleukin-15, interleukin-17, keratinocyte growth factor, leptin, leukemia inhibitory factor, macrophage colony-stimulating factor, and macrophage inflammatory protein-1 alpha.

Differentiation agents according to the invention also include growth factors such as 6Ckine (recombinant), activin A, AlphaA-interferon, alpha-interferon, amphiregulin, angiogenin, 8-endothelial cell growth factor, beta cellulin, B-interferon, brain derived neurotrophic factor, CI0 (recombinant), cardiotrophin-1, ciliary neurotrophic factor, cytokine-induced neutrophil chemoattractant-1, endothelial cell growth supplement, eotaxin, epidermal growth factor, epithelial neutrophil activating peptide-78, erythropoietin, estrogen receptor-alpha, estrogen receptor-B, fibroblast growth factor (acidic/basic, heparin stabilized, recombinant), FLT-3/FLK-2 ligand (FLT-3 ligand), gamma-interferon, glial cell line-derived neurotrophic factor, Gly-His-Lys, granulocyte colony-stimulating factor, granulocyte macrophage colony-stimulating factor, GRO-alpha/MGSA, GRO-B, GRO-gamma, HCC-1, heparin-binding epidermal growth factor like growth factor, hepatocyte growth factor, heregulin-alpha (EGF domain), insulin growth factor binding protein-1, insulin-like growth factor binding protein-1/IGF-1 complex, insulin-like growth factor, insulin-like growth factor II, 2.5S nerve growth factor (NGF), 7S-NGF, macrophage inflammatory protein-1B, macrophage inflammatory protein-2, macrophage inflammatory protein-3 alpha, macrophage inflammatory protein-3B, monocyte chemotactic protein-1, monocyte chemotactic protein-2, monocyte chemotactic protein-3, neurotrophin-3, neurotrophin-4, NGF-B (human or rat recombinant), oncostatin M (human or mouse recombinant), pituitary extract, placenta growth factor, platelet-derived endothelial cell growth factor, platelet-derived growth factor, pleiotrophin, rantes, stem cell factor, stromal cell-derived factor 1B/pre-B cell growth stimulating factor, thrombopoietin, transforming growth factor alpha, transforming growth factor-B1, transforming growth factor-B2, transforming growth factor-B3, transforming growth-factor-B5, tumor necrosis factor (alpha and B), and vascular endothelial growth factor.

Differentiation agents according to the invention also include hormones and hormone antagonists, such as 17B- estradiol, adrenocorticotropic hormone, adrenomedullin, alpha-melanocyte stimulating hormone, chorionic gonadotropin, corticosteroid-binding globulin, corticosterone, dexamethasone, estriol, follicle stimulating hormone, gastrin 1, glucagon, gonadotropin, hydrocortisone, insulin, insulin-like growth factor binding protein, L-3,3',5'-triiodothyronine, L-3,3',5-triiodothyronine, leptin, leutinizing hormone, L-thyroxine, melatonin, MZ-4, oxytocin, parathyroid hormone, PEC-60, pituitary growth hormone, progesterone, prolactin, secretin, sex hormone binding globulin, thyroid stimulating hormone, thyrotropin releasing factor, thyroxine-binding globulin, and vasopressin.

In addition, differentiation agents according to the invention include extracellular matrix components such as fibronectin, proteolytic fragments of fibronectin, laminin, thrombospondin, aggrecan, and syndecan.

Differentiation agents according to the invention also include antibodies to various factors, such as anti-low density lipoprotein receptor antibody, anti-progesterone receptor, internal antibody, anti-alpha interferon receptor chain 2 antibody, anti-c-c chemokine receptor 1 antibody, anti-CD 118 antibody, anti-CD 119 antibody, anti-colony stimulating factor-1 antibody, anti-CSF-1 receptor/c-fms antibody, anti-epidermal growth factor (AB-3) antibody, anti-epidermal growth factor receptor antibody, anti-epidermal growth factor receptor, phospho-specific antibody, anti-epidermal growth factor (AB-1) antibody, anti-erythropoietin receptor antibody, anti-estrogen receptor antibody, anti-estrogen receptor, C-terminal antibody, anti-estrogen receptor-B antibody, anti-fibroblast growth factor receptor antibody, anti-fibroblast growth factor, basic antibody, anti-gamma-interferon receptor chain antibody, anti-gamma-interferon human recombinant antibody, anti-GFR alpha-1 C-terminal antibody, anti-GFR alpha-2 C-terminal antibody, anti-granulocyte colony-stimulating factor (AB-1) antibody, anti-granulocyte colony-stimulating factor receptor antibody, anti-insulin receptor antibody, anti-insulin-like growth factor-1 receptor antibody, anti-interleukin-6 human recombinant antibody, anti-interleukin-1 human recombinant antibody, anti-interleukin-2 human recombinant antibody, anti-leptin mouse recombinant antibody, anti-nerve growth factor receptor antibody, anti-p60, chicken antibody, anti-parathyroid hormone-like protein antibody, anti-platelet-derived growth factor receptor antibody, anti-platelet-derived growth factor receptor-B antibody, anti-platelet-derived growth factor-alpha antibody, anti-progesterone receptor antibody, anti-retinoic acid receptor-alpha antibody, anti-thyroid hormone nuclear receptor antibody, anti-thyroid hormone nuclear receptor-alpha 1/Bi antibody, anti-transferrin receptor/CD71 antibody, anti-transforming growth factor-alpha antibody, anti-transforming growth factor-B3 antibody, anti-tumor necrosis factor-alpha antibody, and anti-vascular endothelial growth factor antibody.

This invention also provides a library of differentiated hematopoietic cells that can provide matched cells to potential patient recipients as described above. In certain embodiments, the cells are stored frozen. Accordingly, in one embodiment, the invention provides a method of conducting a pharmaceutical business, comprising the step of providing differentiated hematopoietic cell preparations that are homozygous for at least one histocompatibility antigen, wherein cells are chosen from a bank of such cells comprising a library of human hemangio-colony forming cells or non-engrafting hemangio cells that can be expanded by the methods disclosed herein, wherein each hemangio-colony forming cell or non-engrafting hemangio cells preparation is hemizygous or homozygous for at least one MHC allele present in the human population, and wherein said bank of hemangio-colony forming cells or non-engrafting hemangio cells comprises cells that are each hemizygous or homozygous for a different set of MHC alleles relative to the other members in the bank of cells. As mentioned above, gene targeting or loss of heterozygosity may be used to generate the hemizygous or homozygous MHC allele stem cells used to derive the hemangio-colony forming cells or non-engrafting hemangio cells. In certain embodiments, hemangio-colony forming cells or non-engrafting hemangio cells of all blood types are included in the bank. In certain embodiments, hemangio-colony forming cells or non-engrafting hemangio cells are matched to a patient to ensure that differentiated hematopoietic cells of the patient's own blood type are produced. In certain embodiments, hemangio-colony forming cells or non-engrafting hemangio cells are negative for antigenic factors A, B, Rh, or any combination thereof. In certain embodiments, the differentiated hematopoietic cells are universal donor cells. By way of example, hematopoietic cells that are type O and Rh negative can be universally used for blood transfusion. In certain embodiments, the invention provides methods for producing type O, Rh negative red blood cells for universal transfusion.

In certain embodiments, red blood cells differentiated from hemangio-colony forming cells or non-engrafting hemangio cells express fetal hemoglobin. Transfusion of red blood cells that express fetal hemoglobin may be especially useful in the treatment of Sickle cell anemia. As such, the present invention provides improved methods for treating Sickle cell anemia.

In one embodiment, after a particular hemangio-colony forming cell preparation or a non-engrafting hemangio cell preparation is chosen to be suitable for a patient, it is thereafter expanded to reach appropriate quantities for patient treatment and differentiated to obtain differentiated hematopoietic cells prior to administering cells to the recipient. Methods of conducting a pharmaceutical business may also comprise establishing a distribution system for distributing the preparation for sale or may include establishing a sales group for marketing the pharmaceutical preparation.

In any of the foregoing, hemangio-colony forming cells or non-engrafting hemangio cells can be directly differentiated or hemangio-colony forming cells or non-engrafting hemangio cells can be frozen for later use. In certain embodiments, the invention provides a frozen culture of hemangio-colony forming cells or non-engrafting hemangio cells suitable for later thawing and expansion, and also suitable for differentiation to hematopoietic or endothelial lineages.

Human hemangio-colony forming cells or non-engrafting hemangio cells can be used to generate substantial numbers of hematopoietic cell types that can be used in blood transfusions. For examples, substantial numbers of homogeneous or heterogeneous populations RBCs and/or platelets can be generated from human hemangio-colony forming cells. Hemangio-colony forming cells, non-engrafting hemangio cells and hematopoietic cell types differentiated therefrom can be banked, as is currently done with donated blood products, and used in transfusions and other treatments. Banking of these products will help alleviate the critical shortage of donated blood products. Additionally, hemangio-colony forming cells, non-engrafting hemangio cells and derivative products can be genetically manipulated in vitro to provide universal donor blood products.

As such, in certain aspects the invention provides a method of conducting a blood banking business. The subject banking business involves the derivation and storage (long or short term) of hemangio-colony forming cells, non-engrafting hemangio cells and/or hematopoietic cell types (e.g., RBCs, platelets, lymphocytes, etc.) generated therefrom. Cells can be cryopreserved for long term storage, or maintained in culture for relatively short term storage. Cells can be typed and cross-matched in much the same way the currently available blood products are typed, and the cells can be stored based on type. Additionally and in certain embodiments, cells can be modified to specifically generate cells that are A negative and/or B negative and/or Rh negative to produce cells that are universally or nearly universally suitable for transfusion into any patient.

Note that hemangio-colony forming cells, non-engrafting hemangio cells and/or differentiated hematopoietic cell types can be generated using any of the methods of the invention detailed through the specification.

In certain embodiments of a method of conducting a blood banking business, the cells (hemangio-colony forming cells, non-engrafting hemangio cells and/or differentiated hematopoietic cell types) are generated and stored at one or more central facilities. Cells can then be transferred to, for example, hospitals or treatment facilities for use in patient care. In certain other embodiments, cells are maintained in a cryopreserved state and specifically thawed and prepared for transfusion based on orders from hospitals or other treatment facilities. Such orders may be a standing order (e.g., generate and provide a certain quantity of cells of a certain number of units In certain embodiments, the method includes a system for billing hospitals or insurance companies for the costs associated with the banked products.

In certain embodiments of any of the foregoing, the cells can be allocated based on cell number, volume, or any unit that permits the user to quantify the dose being administered to patients and/or to compare these doses to that administered during a standard blood transfusion.

In certain embodiments, the cells are generated, stored, and administered as a mixed population of cells. For example, the preparation may include cells of varying developmental stages, as well as distinct cell types. In other embodiments, the cells are generated, stored, and/or administered as a substantially purified preparation of a single cell type.

In certain embodiments, the preparations of cells are screened for one or more infectious diseases. Screening may occur prior to or subsequent to generation or storage. For example, the preparations of cells may be screened to identify hepatitis, HIV, or other blood-borne infectious disease that could be transmitted to recipients of these products.

Induction of Tolerance in Graft Recipients

The human hemangioblast cells generated and expanded by the methods of this invention, or expanded by the methods of this invention, may be used to induce immunological tolerance. Immunological tolerance refers to the inhibition of a graft recipient's immune response which would otherwise occur, e.g., in response to the introduction of a nonself MHC antigen (e.g., an antigen shared with the graft and the tolerizing hemangioblasts) into the recipient. Thus, tolerance refers to inhibition of the immune response induced by a specific donor antigen as opposed to the broad spectrum immune inhibition that may be elicited using immunosuppressants. Tolerance may involve humoral, cellular, or both humoral and cellular responses. Tolerance may include the elimination and/or inactivation of preexisting mature donor-reactive T cells as well as long-term (e.g. lifelong) elimination and/or inactivation of newly developing donor-reactive T cells.

The methods described in the present invention of generating and expanding human hemangioblasts offer several advantages for inducing tolerance. The methods of the present invention result in the generation of large, previously unobtainable numbers of human hemangioblasts. Large numbers of human hemangioblasts allow induction of tolerance in graft recipients with less toxic preconditioning protocols. Furthermore, the methods of the present invention provide for the generation of a library of human hemangioblasts, each of which is hemizygous or homozygous for at least one MHC allele present in the human population, wherein each member of said library of hemangioblast cells is hemizygous or homozygous for a different set of MHC alleles relative to the other members in the library. Such a library of human hemangioblasts can be used in the selection of tolerizing human hemangioblast cells such that cells can be selected to match any available donor graft.

Bone marrow transplantation and subsequent establishment of hematopoietic or mixed chimerism have previously been shown to induce specific tolerance to new tissue types derived from hematopoietic stem cells in both murine and human models. Hematopoietic or mixed chimerism refers to the production in a recipient of hematopoietic cells derived from both donor and recipient stem cells. Hence, if a recipient achieves hematopoietic chimerism, the recipient will be tolerant to donor-specific antigens. In many protocols for inducing tolerance, the tolerizing donor cells that are administered to the recipient engraft into the bone marrow of the recipient. To create hematopoietic space in the recipient bone marrow for the donor cells, some protocols require a step of creating hematopoietic space (e.g., by whole body irradiation), and such a step is typically toxic or harmful to the recipient. However, if very large numbers of donor tolerizing cells are available, there is evidence from rodent models that irradiation can be completely eliminated, thereby achieving hematopoietic or mixed chimerism with the advantage of less toxic pre-conditioning regimens. Thus, mixed chimerism can be achieved, for example, with specific, non-myeloablative recipient conditioning.

Accordingly, as the novel methods described herein enable the production of large numbers of human hemangioblast cells, the present invention offers the advantage of inducing immune tolerance with less rigorous or less toxic conditioning protocols. For example, the hematopoietic space-creating step may be eliminated if a sufficient number of tolerizing donor cells are used.

Accordingly, in certain embodiments of the present invention, human hemangioblast cells generated and expanded or expanded by the methods described herein may be used to induce immunological tolerance. While not wishing to be bound by any theory on the mechanism, the human hemangioblast cells may induce immunological tolerance by homing to the recipient's bone marrow and engrafting into the recipient's bone marrow in order to produce mixed chimerism.

In certain embodiments, donor human hemangioblast cells are administered to a recipient patient (e.g., by intravenous injection) prior to implanting a graft or transplanting an organ, tissue, or cells from the donor into the recipient patient. In certain embodiments, human hemangioblasts are administered to induce tolerance in patients in need thereof (e.g., graft or transplant recipients). Accordingly, in certain embodiments the method of inducing tolerance in a human recipient patient comprises the steps of: (a) selecting a patient in need of a transplant or cellular therapy; (b) administering to said patient human hemangioblast cells derived from a donor or that are matched to the donor, wherein said hemangioblast cells are generated and expanded or expanded according to the methods of this invention, and (c) implanting a donor organ, tissue, or cell graft into the recipient patient, wherein said hemangioblast cells induce tolerance to donor antigens. In certain embodiments, the patient will receive an organ, tissue, or cell therapy, wherein the organ, tissue, or cells are obtained from the donor or a donor cell source. For example, hemangioblast cells from a donor can be (1) expanded according to the methods described herein to generate a large number of donor tolerizing cells, and (2) expanded and differentiated in vitro to obtain hematopoietic or endothelial cells or tissues, which can be subsequently implanted into the recipient patient. In other embodiments, the organ, tissue, or cell therapy is not derived from donor hemangioblast cells but is matched to the donor hemangioblasts.

As used herein, the term "matched" relates to how similar the HLA typing is between the donor and the recipient (e.g., graft). In one embodiment, the term "matched" with respect to donor hemangioblast cells and graft refers to a degree of match at the MHC class I and/or at the MHC class II alleles such that rejection does not occur. In another embodiment, the term "matched" with respect to donor hemangioblasts and graft refers to a degree of match at the MHC class I and/or at the MHC class II alleles such that the donor graft is tolerized by its matching donor hemangioblast cells. In another embodiment, the term "matched" with respect to donor hemangioblast and graft refers to a degree of match at the MHC class I and/or at the MHC class II alleles such that immunosuppression is not required.

The methods described herein for inducing tolerance to an allogeneic antigen or allogeneic graft may be used where, as between the donor and recipient, there is degree of mismatch at MHC loci or other loci, such that graft rejection results. Accordingly, for example, in certain embodiments, there may be a mismatch at least one MHC locus or at least one other locus that mediates recognition and rejection, e.g., a minor antigen locus. In some embodiments, for example, the HLA alleles of the recipient and donor are mismatched and result in one or more mismatched antigens. With respect to class I and class II MHC loci, the donor and recipient may be, for example: matched at class I and mismatched at class II; mismatched at class I and matched at class II; mismatched at class I and mismatched at class II; matched at class I, matched at class II. In any of these combinations other loci which control recognition and rejection, e.g., minor antigen loci, may be matched or mismatched. Mismatched at MHC class I means mismatched for one or more MHC class I loci, e.g., mismatched at one or more of HLA-A, HLA-B, or HLA-C. Mismatched at MHC class II means mismatched at one or more MHC class II loci, e.g., mismatched at one or more of a DPA, a DPB, a DQA, a DQB, a DRA, or a DRB. For example, the hemangioblasts and the graft may be matched at class II HLA-DRB1 and DQB1 alleles. The hemangioblasts and graft may further be matched at two or more class I HLA-A, B, or C, alleles (in addition to having matched DRB1 and DQB1 alleles).

In other embodiments, the tolerizing donor cells are cells derived from the hemangioblasts generated and expanded or expanded by the methods described herein. According to this embodiment, donor human hemangioblasts are differentiated in vitro to give rise to donor hematopoietic stem cells, and the donor hematopoietic stem cells are then administered to the recipient patient to induce tolerance. In any of the above methods, the donor hemangioblasts or hematopoietic stem cells derived therefrom and administered to said recipient prepare the recipient patient for the matched (with respect to the donor tolerizing cells) transplant or graft by inducing tolerance in said recipient.

In other embodiments, the method of inducing tolerance further comprises the step(s) of creating hematopoietic space (to promote engraftment of hemangioblasts or hematopoietic stem cells derived therefrom). In another embodiment, the method of inducing tolerance further comprises the step(s) of temporarily inhibiting rejection of donor hemangioblast cells or hematopoietic stem cells derived therefrom by, for example, eliminating and/or inactivating preexisting donor-reactive T cells. In order to create hematopoietic space, the method may include irradiation (e.g., whole body, lymphoid, or selective thymic irradiation). To prevent rejection of donor cells, the method may further comprise the administration of drugs or antibodies (e.g., inhibitors of cell proliferation, antimetabolites, or anti-T cell or anti-CD8 or anti-CD4 antibodies), and/or other treatments that promote survival and engraftment of the donor cells and the formation of mixed chimerism (e.g., the administration of stromal cells or growth factors, cytokines, etc. to said recipient, or other agents that deplete or inactive the recipient's natural antibodies). In certain embodiments, the irradiation, antibodies, drugs, and/or other agents administered to create hematopoietic space and/or promote survival of donor cells in the recipient, is sufficient to inactivate thymocytes and/or T cells in the recipient. Such a step of creating hematopoietic space and/or temporarily inhibiting rejection of donor cells may be performed, for example, before the introduction of the donor hemangioblast cells to said recipient. Alternatively, the patient may receive an agent or method for blocking, eliminating, or inactivating T cells concurrently with the administration of the donor tolerizing cells.

In certain embodiments, a combination of hematopoietic space-creating and immunosuppressive methods is used. For example, a recipient may receive an anti-T cell antibody in combination with low dose whole body irradiation and/or thymic irradiation. In one embodiment, the recipient may receive anti-CD4 and anti-CD8 antibodies, followed by a mild, nonmyeloablative dose of whole body irradiation (e.g., a dose that eliminates a fraction of the recipient's bone marrow without rendering the bone marrow unrecoverable) and selective thymic irradiation or alternatively, an additional dose of T cell-inactivating antibodies or costimulatory blocking reagents (e.g., CTLA4-Ig and/or anti-CD40L antibody). Following the irradiation, donor hemangioblast cells, or hematopoietic stem cells derived therefrom, may be administered to the recipient (e.g., by intravenous injection). In this embodiment, whole body irradiation to promote engraftment of donor cells may be replaced by administering a large number of donor human hemangioblasts or hematopoietic stem cells derived therefrom. Obtaining such large numbers of donor human cells can be achieved according to the methods described herein.

In another embodiment, treatments to deplete or inactivate recipient T cells may help to prevent inhibition of engraftment or promote survival of the administered donor tolerizing human hemangioblast cells. In another embodiment, the method may include clonal deletion of donor-reactive cells in the recipient patient. For example, a patient may receive a mild dose of whole body irradiation, followed by administration of donor human hemangioblasts and T cell costimulatory blockade. Alternatively, a patient may receive T cell costimulatory blockade and administration of large numbers of donor human hemangioblast cells without receiving irradiation.

In another embodiment, tolerance may be achieved without myeloablative conditioning of the recipient. In one embodiment, a recipient may receive donor human hemangioblasts in combination with anti-CD40L to facilitate engraftment of donor hemangioblasts. For example, a recipient may receive large numbers of donor hemangioblasts, along with anti-CD40L monoclonal antibody, followed within a few days by a dose of CTLA4-Ig. Such a protocol may delete donor-reactive T cells and block the CD40-CD40L interaction. The novel methods described herein for generating and expanding human hemangioblasts in vitro render such a mild tolerance protocol feasible.

Following recipient conditioning and/or depletion or blocking of donor-reactive T cells, donor tolerizing human hemangioblasts generated by the methods of the present invention are administered to the recipient. Donor human hemangioblasts may be derived from hemangioblasts obtained from a tissue or cell source from the donor. Alternatively, donor human hemangioblasts may be obtained from a different non-donor source that is matched to the donor.

In certain embodiments, tolerance is induced in a recipient patient by administering donor human hemangioblasts in multiple administrations (e.g., by two, three, four, or more administrations of the donor cells). Accordingly, tolerance may be induced by a method comprising multiple administrations of donor tolerizing cells, wherein the multiple administrations are given to the recipient within a timeframe of a week or less.

In certain embodiments, the ability of the human hemangioblast cells of this invention to induce immunological tolerance may be evaluated using different experimental model systems. For example, the ability to establish a human immune system in a SCID mouse has been used to study the human immune response in an experimental model. It has been previously shown that human fetal liver and thymus tissue may be used to reconstitute a functional human immune system in an immuno-incompetent mouse recipient. Similarly, the functional capacity of the human hemangioblast cells of this invention can be assessed using a similar experimental model system. For example, the ability of human hemangioblasts to replace human fetal liver in establishing a functional human immune system in the mouse can be evaluated using the above-described experimental model. Further, in a mouse with a functional human immune system (e.g., where a human fetal liver and thymus tissue is used to establish a human immune system in a SCID mouse to produce a hu-SCID mouse), human "donor" hemangioblasts (mismatched with respect to the fetal liver and thymic tissue used to establish the hu-SCID mouse) may be administered to the hu-SCID mouse, according to any of the methods described above, in order to achieve mixed chimerism. Tolerance to donor antigen can be subsequently tested upon implantation of an allograft matched with respect to the donor hemangioblasts into these animals.

In certain embodiments, the present invention relates to cell combinations. Effective cell combinations comprise two components: a first cell type to induce immunological tolerance, and a second cell type that regenerates the needed function. Both cell types may be produced by the methods of the present invention and obtained from the same donor. For example, human hemangioblast cells from a donor may be used as the tolerizing donor cells. Cells from the donor (e.g., embryonic stem cells, pluripotent stem cells or early progenitor cells, or hemangioblasts) may also be used to generate, for example, hematopoietic cells or endothelial cells (as described herein), neural cells such as oligodendrocytes, hepatocytes, cardiomyocytes or cardiomyocyte precursors, or osteoblasts and their progenitors. Accordingly, the donor human hemangioblasts may be used to induce tolerance in a recipient such that the recipient is tolerant to cells or tissues derived from said donor hemangioblast cells or from said donor embryonic or pluripotent stem cells.

In another embodiment, the two cell components of the cell combinations of the present invention may be obtained from different sources or donors, wherein the two sources or donors are matched. For example, hemangioblasts may be generated from an embryonic stem cell source, whereas the graft cells or tissues may be obtained from a source that is different from the embryonic stem cell source used to generate the human hemangioblasts. In such embodiments, the two sources are matched.

For any of the therapeutic purposes described herein, human hemangioblast or hematopoietic cells derived therefrom for immunotolerance may be supplied in the form of a pharmaceutical composition, comprising an isotonic excipient prepared under sufficiently sterile conditions for human administration.

Hemangioblasts in Gene Therapy

Other aspects of the invention relate to the use of hemangioblast cells, non-engrafting hemangio cells, or hematopoietic or endothelial cells differentiated therefrom, or in turn cells further differentiated from these cells, in gene therapy. The preparation of mammalian hemangioblast cells or non-engrafting hemangio cells of the invention may be used to deliver a therapeutic gene to a patient that has a condition that is amenable to treatment by the gene product of the therapeutic gene. The hemangioblasts and non-engrafting hemangio cells are particularly useful to deliver therapeutic genes that are involved in or influence angiogenesis (e.g. VEGF to induce formation of collaterals in ischemic tissue), hematopoiesis (e.g. erythropoietin to induce red cell production), blood vessel function (e.g. growth factors to induce proliferation of vascular smooth muscles to repair aneurysm) or blood cell function (e.g. clotting factors to reduce bleeding) or code for secreted proteins e.g. growth hormone. Methods for gene therapy are known in the art. See for example, U.S. Pat. No. 5,399,346 by Anderson et al. A biocompatible capsule for delivering genetic material is described in PCT Publication WO 95/05452 by Baetge et al. Methods of gene transfer into bone-marrow derived cells have also previously been reported (see U.S. Pat. No. 6,410,015 by Gordon et al.). The therapeutic gene can be any gene having clinical usefulness, such as a gene encoding a gene product or protein that is involved in disease prevention or treatment, or a gene having a cell regulatory effect that is involved in disease prevention or treatment. The gene products may substitute a defective or missing gene product, protein, or cell regulatory effect in the patient, thereby enabling prevention or treatment of a disease or condition in the patient.

Accordingly, the invention further provides a method of delivering a therapeutic gene to a patient having a condition amenable to gene therapy comprising, selecting the patient in need thereof, modifying the preparation of hemangioblasts or non-engrafting hemangio cells so that the cells carry a therapeutic gene, and administering the modified preparation to the patient. The preparation may be modified by techniques that are generally known in the art. The modification may involve inserting a DNA or RNA segment encoding a gene product into the mammalian hemangioblast cells, where the gene enhances the therapeutic effects of the hemangioblast cells or the non-engrafting hemangio cells. The genes are inserted in such a manner that the modified hemangioblast cell will produce the therapeutic gene product or have the desired therapeutic effect in the patient's body. In one embodiment, the hemangioblasts or non-engrafting hemangio cells are prepared from a cell source originally acquired from the patient, such as bone marrow. The gene may be inserted into the hemangioblast cells or non-engrafting hemangio cells using any gene transfer procedure, for example, naked DNA incorporation, direct injection of DNA, receptor-mediated DNA uptake, retroviral-mediated transfection, viral-mediated transfection, non-viral transfection, lipid-mediated transfection, electrotransfer, electroporation, calcium phosphate-mediated transfection, microinjection or proteoliposomes, all of which may involve the use of gene therapy vectors. Other vectors can be used besides retroviral vectors, including those derived from DNA viruses and other RNA viruses. As should be apparent when using an RNA virus, such virus includes RNA that encodes the desired agent so that the hemangioblast cells that are transfected with such RNA virus are therefore provided with DNA encoding a therapeutic gene product. Methods for accomplishing introduction of genes into cells are well known in the art (see, for example, Ausubel, id.).

In accordance with another aspect of the invention, a purified preparation of human hemangioblast cells or non-engrafting hemangio cells, in which the cells have been modified to carry a therapeutic gene, may be provided in containers or commercial packages that further comprise instructions for use of the preparation in gene therapy to prevent and/or treat a disease by delivery of the therapeutic gene. Accordingly, the invention further provides a commercial package (i.e., a kit) comprising a preparation of mammalian hemangioblast cells or non-engrafting hemangio cells of the invention, wherein the preparation has been modified so that the cells of the preparation carry a therapeutic gene, and instructions for treating a patient having a condition amenable to treatment with gene therapy.

Other Commercial Applications and Methods

Certain aspects of the present invention pertain to the expansion of human hemangioblasts and non-engrafting hemangio cells to reach commercial quantities. In particular embodiments, human hemangioblasts and non-engrafting hemangio cells are produced on a large scale, stored if necessary, and supplied to hospitals, clinicians or other healthcare facilities. Once a patient presents with an indication such as, for example, ischemic or vascular injury, or is in need of hematopoietic reconstitution, human hemangioblasts or non-engrafting hemangio cells can be ordered and provided in a timely manner. Accordingly, the present invention relates to methods of generating and expanding human hemangioblasts and non-engrafting hemangio cells to attain cells on a commercial scale, cell preparations comprising human hemangioblasts or non-engrafting hemangio cells derived from said methods, as well as methods of providing (i.e., producing, optionally storing, and selling) human hemangioblasts or non-engrafting hemangio cells to hospitals and clinicians. Further, hemangioblast lineage cells or non-engrafting hemangio lineage cells may be produced in vitro and optionally stored and sold to hospitals and clinicians.

Accordingly certain aspects of the present invention relate to methods of production, storage, and distribution of hemangioblasts or non-engrafting hemangio cells expanded by the methods disclosed herein. Following human hemangioblast or non-engrafting hemangio cells generation and expansion in vitro, human hemangioblasts or non-engrafting hemangio cells may be harvested, purified and optionally stored prior to a patient's treatment. Alternatively, in situations in which hemangioblast or non-engrafting hemangio lineage cells are desired, human hemangioblasts or non-engrafting hemangio cells may be differentiated further in vitro prior to a patient's treatment. Thus, in particular embodiments, the present invention provides methods of supplying hemangioblasts or non-engrafting hemangio cells to hospitals, healthcare centers, and clinicians, whereby hemangioblasts, non-engrafting hemangio cells, hemangioblast lineage cells, or non-engrafting hemangio lineage cells produced by the methods disclosed herein are stored, ordered on demand by a hospital, healthcare center, or clinician, and administered to a patient in need of hemangioblast, non-engrafting hemangio cells, hemangioblast lineage, or non-engrafting hemangio lineage therapy. In alternative embodiments, a hospital, healthcare center, or clinician orders human hemangioblasts or non-engrafting hemangio cells based on patient specific data, human hemangioblasts or non-engrafting hemangio cells are produced according to the patient's specifications and subsequently supplied to the hospital or clinician placing the order.

Further aspects of the invention relate to a library of hemangioblasts, non-engrafting hemangio cells, hemangioblast lineage cells, and/or non-engrafting hemangio lineage cells that can provide matched cells to potential patient recipients. Accordingly, in one embodiment, the invention provides a method of conducting a pharmaceutical business, comprising the step of providing hemangioblast or non-engrafting hemangio cell preparations that are homozygous for at least one histocompatibility antigen, wherein cells are chosen from a bank of such cells comprising a library of human hemangioblasts or non-engrafting hemangio cells that can be expanded by the methods disclosed herein, wherein each hemangioblast or non-engrafting hemangio cell preparation is hemizygous or homozygous for at least one MHC allele present in the human population, and wherein said bank of hemangioblast cells or non-engrafting hemangio cells comprises cells that are each hemizygous or homozygous for a different set of MHC alleles relative to the other members in the bank of cells. As mentioned above, gene targeting or loss of heterozygosity may be used to generate the hemizygous or homozygous MHC allele stem cells used to derive the hemangioblasts. In one embodiment, after a particular hemangioblast or non-engrafting hemangio cell preparation is chosen to be suitable for a patient, it is thereafter expanded to reach appropriate quantities for patient treatment. Such methods may further comprise the step of differentiating the hemangioblasts or non-engrafting hemangio cells to obtain hematopoietic and/or endothelial cells prior to administering cells to the recipient. Methods of conducting a pharmaceutical business may also comprise establishing a distribution system for distributing the preparation for sale or may include establishing a sales group for marketing the pharmaceutical preparation.

Other aspects of the invention relate to the use of the human hemangioblasts and non-engrafting hemangio cells of the present invention as a research tool in settings such as a pharmaceutical, chemical, or biotechnology company, a hospital, or an academic or research institution. For example, human hemangioblasts, non-engrafting hemangio cells and derivative cells thereof (e.g., endothelial cells) may be used to screen and evaluate angiogenic and anti-angiogenic factors or may be used in tissue engineering. In addition, because the hemangioblasts and non-engrafting hemangio cells obtained and expanded by the methods disclosed herein have dual potential to differentiate into hematopoietic and endothelial cells, they may be used for the cellular and molecular biology of hematopoiesis and vasculogenesis. Further, the human hemangioblasts and non-engrafting hemangio cells may be used for the discovery of novel markers of these cells, genes, growth factors, and differentiation factors that play a role in hematopoiesis and vasculogenesis, or for drug discovery and the development of screening assays for potentially toxic or protective agents.

In other embodiments of the present invention, hemangioblast and non-engrafting hemangio lineage cells (such as blood cells) are also used commercially. Hematopoietic cells may be used to generate blood products, such as hemoglobin and growth factors, that may be used for clinical and research applications.

The present invention also includes methods of obtaining human ES cells from a patient and then generating and expanding human hemangioblasts or non-engrafting hemangio cells derived from the ES cells. These hemangioblasts and non-engrafting hemangio cells may be stored. In addition, these hemangioblasts and non-engrafting hemangio cells may be used to treat the patient from which the ES were obtained or a relative of that patient.

As the methods and applications described above relate to treatments, pharmaceutical preparations, and the storing of hemangioblasts or non-engrafting hemangio cells, the present invention also relates to solutions of hemangioblasts and non-engrafting hemangio cells that are suitable for such applications. The present invention accordingly relates to solutions of hemangioblasts and non-engrafting hemangio cells that are suitable for injection into a patient. Such solutions may comprise cells formulated in a physiologically acceptable liquid (e.g., normal saline, buffered saline, or a balanced salt solution). A solution may optionally comprise factors that facilitate cell differentiation in vivo. A solution may be administered to a patient by vascular administration (e.g., intravenous infusion), in accordance with art accepted methods utilized for bone marrow transplantation. In some embodiments, the cell solution is administered into a peripheral vein, a superficial peripheral vein, or alternatively, by central venous administration (e.g., through a central venous catheter). The number of cells in the solution may be at least about $10^2$ and less than about $10^9$ cells. In other embodiments, the number of cells in the solution may range from about $10^1$, $10^2$, $5\times10^2$, $10^3$, $5\times10^3$, $10^4$, $10^5$, $10^6$, $10^7$, or $10^8$ to about $5\times10^2$, $10^3$, $5\times10^3$, $10^4$, $10^5$, $10^6$, $10^7$, $10^8$, or $10^9$, where the upper and lower limits are selected independently, except that the lower limit is always less than the upper limit. Further, the cells may be administered in a single or in multiple administrations.

Generation of Hemangioblast from Human iPSCs

Based on the method to efficiently and reproducibly generate large numbers of hemangioblasts from multiple hESC lines described herein (see also Lu et al. Nat Methods 2007; 4:501-509; Lu et al. Regen Med 2008; 3:693-704), the inventors further used the hemangioblast platform to differentiate hESCs through hemangioblastic progenitors into erythroid cells on a large scale (approximately $10^{10}$ to $10^{11}$ cells/six-well plate hESCs), which is over a thousand-fold more efficient than previously reported.

Little has been reported about the capacity of iPSCs to undergo directed differentiation, especially, toward hemangioblasts. A recent report by Choi et al (STEM CELLS 2009; 27(3):559-567) describes studies with human iPSCs utilizing an OP9 feeder-based culture system that yielded hematopoietic and endothelial differentiation, demonstrating the potential of human iPSCs. Similarly, Zhang et al., (Circ Res 2009; 104:e30-e41.) reports the derivation of functional cardiomyocytes from human iPSCs, albeit with low efficiency compared to hESCs, using EB method. Efficient generation of hemangioblasts from human iPSCs is described herein. The inventors describe conditions for efficient generation of hemangioblasts from human iPSCs, using their experiences with the hESC system.

The present invention will now be more fully described with reference to the following examples, which are illustrative only and should not be considered as limiting the invention described above.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Materials and Methods

Culture of hESCs hESC lines WA01(H1), HUES3, and MA01 were used and maintained as previously described[6]. Briefly, hESCs were grown on mitomycin C-treated mouse embryonic fibroblast (MEF) in complete hESC media. The hESCs were passaged every 3-5 days before reaching confluence using 0.05% trypsin-0.53 mM EDTA. For feeder-free culture, the cells were then grown on hESC-qualified Matrigel matrix (BD Biosciences) in complete Modified TeSR™1 (m TeSR™1) medium (Stem Cell Technologies, Inc), which is based on the formulation of Ludwig et al[7,8]. Cells were maintained according to manufacture's suggested instructions. Briefly, cells were passaged when they reached approximately 90% confluence, usually every 5-7 days with split ratios ranging from 1:3 to 1:6. Cells were treated with dispase (1 mg/ml BD, Biosciences) and incubated for 3-5 minutes at 37° C. to begin dislodging the colonies. Colonies were washed with DMEM/F12 (Mediatech) to remove dispase solution. To extricate the colonies from the tissue culture plastic, the wells were coated with DMEM/F12 and gently scraped until all of the colonies had been displaced. The colonies were transferred to conical tubes, the wells were washed with DMEM/F12 and the cells pooled to collect any remaining in the wells. They were centrifuged for 5 minutes at 1000 rpm. The cell pellets were resuspended in mTeSR™1 media and transferred to Matrigel coated 6 well plates, in 2 ml of mTeSR™1 media per well. Cells were maintained at 37° C. under 5% CO2 and the mTeSR™1 medium was replenished daily.

Immunofluorescent Cytochemistry Analysis

Feeder-free hESC colonies were assayed for Oct-4 and Tra-1-60 expression using immunofluorescence. The cells were fixed with 4% paraformaldehyde (PFA), washed with PBS, and blocked with 5% Normal Goat Serum (Vector Labs), 1% BSA (Sigma) and 0.2% Triton-X-100 (Sigma) in PBS for 30 minutes at room temperature. Cells were incubated with primary antibodies against Oct-4 (Santa Cruz Biotechnology) or Tra-1-60 (Millipore/Chemicon), in blocking solution, overnight at 4° C., washed with PBS and incubated with a biotin conjugated secondary antibody (Jackson ImmunoResearch Labs), in blocking solution, for 45 minutes at room temp. After further washing, cells were incubated with Alexa 954 conjugated streptavidin (Invitrogen/Molecular probes), for 15 minutes at room temp followed by an extended final wash in PBS. Cells were mounted in Prolong Gold with DAPI (Invitrogen/Molecular Probes).

Differentiation of Hemangioblasts from hESCs

To induce hESCs cultured on MEFs into hemangioblasts, 80-90% confluent plates were dissociated by 0.05% trypsin digestion. To differentiate feeder-free hESCs into hemangioblasts, 85-90% confluent cells were dislodged from the Matrigel matrix using the protocol described above. Cells from both conditions were plated on Ultra-Low dishes (Corning, N.Y.) in Stemline II (Sigma) medium with different doses of BMP-4, VEGF and bFGF as described previously[2]. Half of the medium was replaced after 48 hours with fresh medium containing the same cytokines or the same medium plus SCF, FLT3 ligand (FL) and Tpo (20 ng/ml, R&D System) which depend on different experiment conditions. After 3.5 days, EBs were collected and dissociated by 0.05% trypsin. Single-cell suspensions were obtained by passing the cells through 22-gauge needle and through a 40-μm cell strainer, collected by centrifugation, and resuspended in 50-100 μl of Stemline II media. Cells ($0.75 \times 10^5$ to $1 \times 10^5$) were mixed with 2.5 ml of blast colony growth medium (BGM) as previously described[2], plated in Ultra-Low dishes and incubated at 37° C. Blast colonies derived from both MEF and feeder-free hESCs were observed 3-4 days after plating, followed shortly thereafter by rapid expansion. Blast cells (BC) are defined in the current study as cells obtained from day-6 blast colonies.

Enrichment of Hemangioblast Precursors

Potential BC precursor surface markers CD31, CD34, KDR, CXCR-4, CD133, ACE, PCLP1, PDGFRα, Tie-2, Nrp-2, Tpo-R and bFGFR-1 were selected for cell enrichment. All antibodies are mouse monoclonal IgG isotype and they are: CD31 and CD34 (Dako Cytomation), KDR and Tpo-R (R&D Systems, Inc.), CXCR-4 (Abcam Inc.), Nrp-2, ACE, PCLP1 and PDGFRα (Santa Cruz Biotechnology), Tie-2 (Cell Signaling Technology, Inc.), bFGFR-1 (Zymed Laboratories), and CD133 (Miltenyi Biotech). Antibody cocktail assembly was performed by EasySep "Do-it-Yourself" Selection Kit (Stem Cell Technologies). Cell suspensions derived from EBs were centrifuged at 1200 rpm for 4 min and resuspended in PBS with 2% FBS/1 mM EDTA buffer at a concentration of $1-2 \times 10^6$ cells/100 μl. The cells were mixed with different antibody cocktails for 15 min at RT and then incubated with EasySep Nanoparticle at RT for 10 additional minutes. Positive selected cells were separated after pouring off supernatant when placing tube with cells in a Magnet holder. Antibody selected positive cells ($1 \times 10^5$) were mix with 2.5 ml of BGM and plated for blast colony development.

Real Time RT-PCR and Data Analysis

Total RNA was extracted from EBs or undifferentiated hESCs using RNeasy Micro Kits (Qiagen) according to manufacture's protocol. cDNAs were synthesized using BD SMART PCR cDNA Synthesis Kit (BD Biosciences) per manual instructions. Real time RT-PCR (qRT-PCR) was performed using FullVelocity SYBR Green QPCR Master Mix (Stratagene). The reactions were set up in triplicate with the following components per reaction: 50 ng of template, 0.2 micromoles of each primer and 1× Master mix. Gene specific sequences of the primers used are listed in Table 1, and annealing temperature for all primers is 55° C. Amplification and real-time data acquisition were performed in a Stratagene Mx3005P with MxPro version 3.0 software. The following cycle conditions were used: one cycle of 95° C. for ten minutes followed by forty cycles of 95° C. for 30 seconds, 55° C. for 1 minute, 72° C. for 30 seconds followed by a final cycle of 95° C. for 1 minute, 55° C. for 30 seconds and 95° C. for 30 seconds. Relative quantification of each target gene was performed based on cycle threshold ($C_T$) normalization to β-actin ($\Delta C_T$) using the $\Delta\Delta C_T$ method[9]. Analysis of relative gene expression data using real-time quantitative PCR and the 2(−delta deltaC(T)) method[9], where the $\Delta C_T$ of each examined gene in the experimental samples was compared to average $\Delta C_T$ of each gene in an undifferentiated hESC control sample ($\Delta\Delta C_T$). Then the fold change in expression was calculated as $2^{-\Delta\Delta C_T}$. The negative fold difference data was convert to a linear "Fold change in expression" value using the following formula: Linear Fold Change in expression=−(1/fold change in expression).

Statistical Analysis

All data were presented as mean±SEM. Intergroup comparisons were performed by unpaired Student's t-test using GraphPad Prism, version 4, software (GraphPad Software, Inc., San Diego, Calif.). $p<0.05$ was interpreted as statistically significant.

Example 2

Both BMP-4 and VEGFs are Required for Hemangioblast Development

Figure 1B:
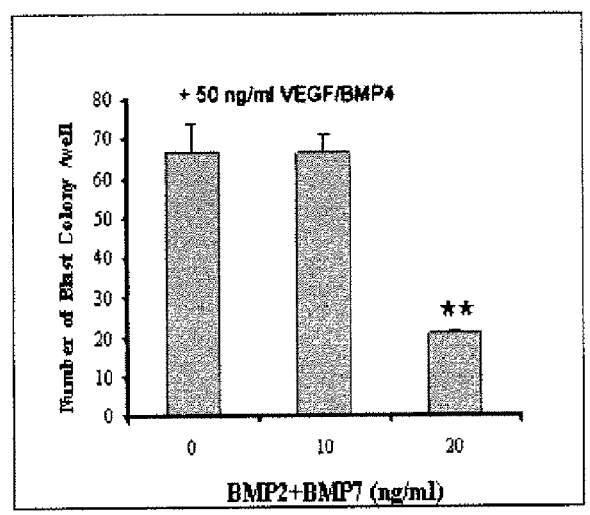
Figure 1C:
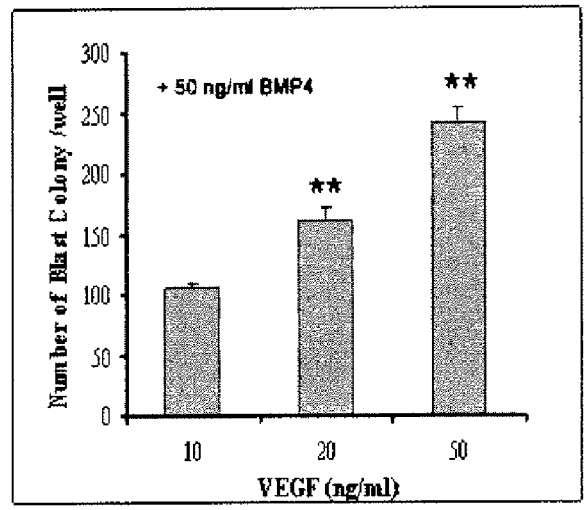

A serum free system to induce hESC differentiation toward the hemangioblastic and hematopoietic lineages was previously described[2,10]. Although BMP-4, VEGF, and a cocktail of early hematopoietic cytokines were used, the absolute requirement and optimal concentrations of the individual factors were not examined. In order to reduce the expense and effort necessary to generate hemangioblasts for future research and clinical applications, the inventors specifically examined the minimal requirements and effects of VEGFs, BMPs, and three early hematopoietic cytokines (TPO, FL and SCF) on the efficient development of blast colonies from hESCs. It was found that BMP-4 is absolutely required for the development of blast colonies under serum-free conditions. No blast colonies were obtained without the supplement of BMP-4 in the medium during EB formation and a clear dose-response effect of BMP-4 was observed for the formation of blast colonies from hESCs (FIG. 1A). Furthermore, BMP-4 could not be substituted by other members of the BMP family. BMP-2 and BMP-7 alone, or a combination of the two, failed to promote BC development. Furthermore, supplementation of BMP-2 and BMP-7 in EB medium containing BMP-4, either showed no effect (10 ng/ml) or inhibited (20 ng/ml) blast colony development (FIG. 1B). However, addition of BMP-4, and BMP-2 and/or BMP-7 in blast colony growth medium (BGM) did not have any effect on the development of blast colonies, suggesting that BMP-4 only promotes the mesoderm/hemangioblastic specification stage, but not the growth and expansion of BCs. Similarly, no blast colonies developed when $VEGF_{165}$ was eliminated from the EB formation medium. $VEGF_{165}$ was found to promote the development of blast colonies in a dose dependent manner (FIG. 1C). $VEGF_{121}$, an isoform of VEGF members that can only bind to KDR and FLT1 receptors[11], can be used as a substitute of $VEGF_{165}$ in promoting the development of blast colonies from hESCs; almost identical numbers of blast colonies (68±5 vs. 67±12) were developed when 50 ng/ml of either $VEGF_{165}$ or $VEGF_{121}$, which is the optimal dose under serum-free condition, was added in EB medium. However, in contrast to BMP-4, no blast colonies were obtained if VEGF was absent in BGM, demonstrating that VEGF plays a critical role both in early stage of mesoderm/hemangioblastic specification and in the growth and expansion of BCs.

In the inventors' original report[2], TPO, FL and SCF were added 48 hours after plating hESCs in EB medium in an effort to further promote early hematopoietic progenitor growth and expansion. Here it was examined whether TPO, FL, and SCF played any role in the specification of hESCs toward the mesoderm/hemangioblast lineage. EBs were formed by plating hESCs in Stemline II medium with 50 ng/ml of BMP-4 and VEGF, and divided into two wells after 48 hours: to one well, 20 ng/ml of TPO, FL and SCF was added, to the other well, no additional factor was added, and the EBs were incubated for another 36 hours. EBs were then collected and single cell suspension was obtained and plated for blast colony formation. Our results show that supplement of TPO, FL and SCF during EB formation has no effect on the development of blast colonies, 242±16 vs. 287±33 blast colonies developed per 1×10$^5$ cells derived from EBs treated with and without TPO, FL and SCF, respectively.

Example 3 bFGf Promotes the Growth, but not Commitment, of Hemangioblasts from hESCs

Figure 2A:
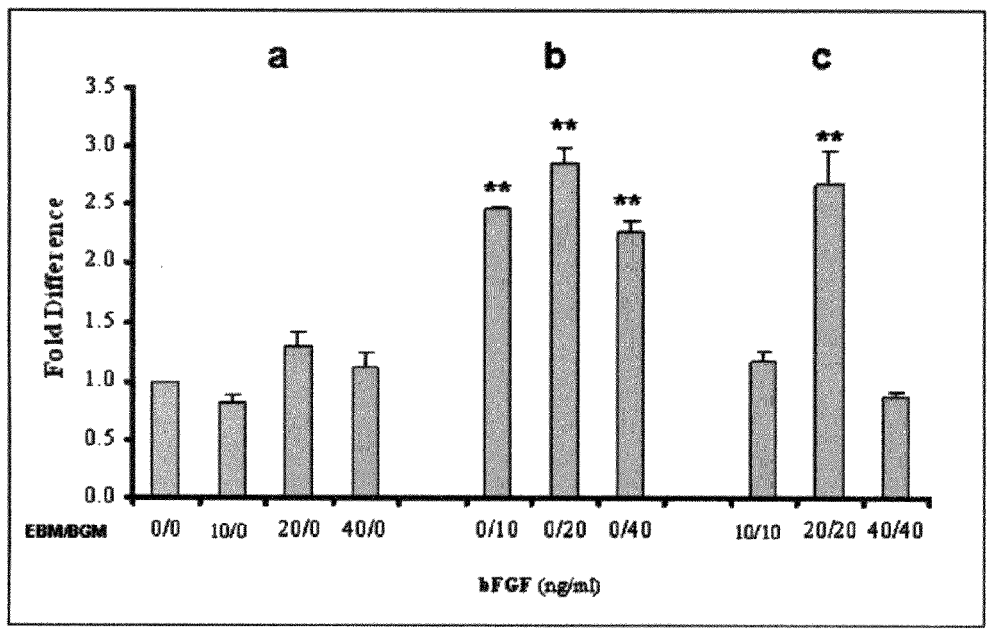
FIG. 2 depicts the effect of bFGF on the development of blast colonies added during different stages in accordance with an embodiment of the present invention. (a) Different doses of bFGF were added in EB medium; (b) Different doses of bFGF were supplemented in blast colony growth medium (BGM); (c) Different doses of bFGF were added in both EB medium and BGM. **$P<0.01$, n=3. B and C. Net-work like structure formation of endothelial cells derived from BCs developed in BGM with (B) and without (C) bFGF. Endothelial cells from both sources formed net-work like structures with no obvious difference.
Figure 3A:
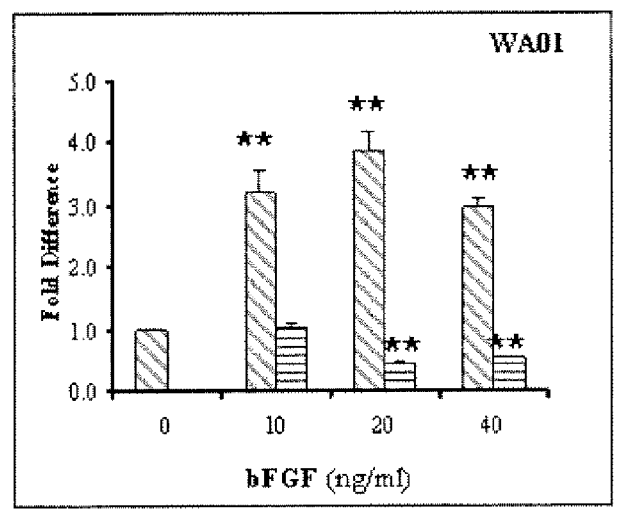
FIG. 3 depicts the effect of bFGF on the development of blast colonies from three hESC lines in accordance with an embodiment of the present invention. Diagonal strips: Different doses of bFGF were added in BGM. Horizontal: Various doses of bFGF were added in EB medium. *$P<0.05$; **$P<0.01$, n=3.
Figure 3B:
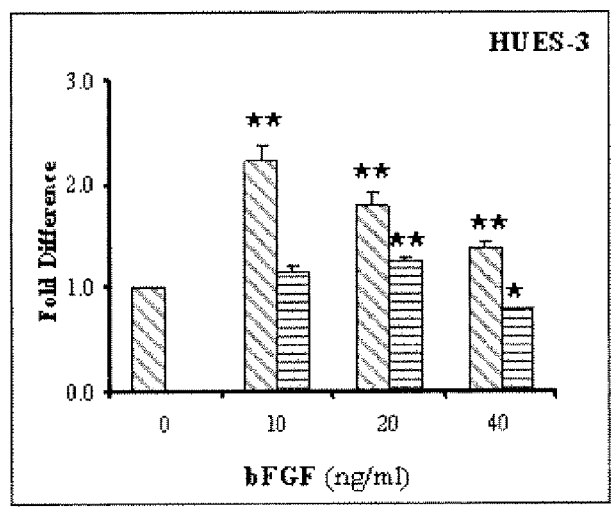
Figure 3C:
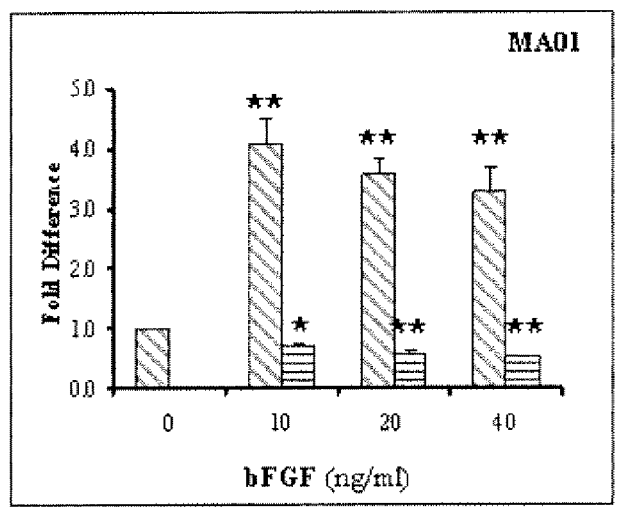

Previous studies have shown that supplement of bFGF during early differentiation promotes murine and human ESC hematopoietic development[12,13,14,5]. Thus, we investigated whether the addition of bFGF during the EB differentiation stage would enhance blast colony formation from hESCs. Addition of bFGF during EB formation had no effect on the development of blast colonies, and, in fact, at a higher dose (40 ng/ml) inhibited the formation of blast colonies from multiple hESC lines (FIG. 2A and FIG. 3). In contrast, the addition of bFGF in BGM significantly enhanced the development of blast colonies (FIG. 2A, FIG. 3). Both the number of blast colonies (p<0.001) and total number of BCs increased significantly compared to BGM without bFGF supplementation. With bFGF at optimal dose (20 ng/ml) in BGM, the blast colonies are larger and healthier, and we consistently harvest approximately 1×10$^8$ BCs from one six-well plate of high quality WA01 hESCs (approximately 1.2×10$^7$ cells) after 6 days growth, which is 8±1 fold higher than that obtained from BGM without the supplement of bFGF.

Figure 2B:
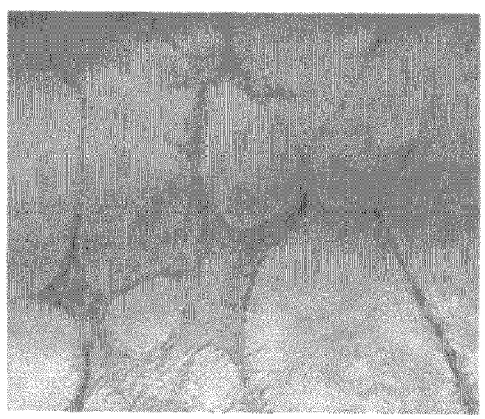
Figure 2C:

To investigate the lineage differentiation potentials of BCs generated with and without supplementation of bFGF, equal numbers of pooled BCs were plated for hematopoietic and endothelial lineage differentiation as previously described[2]. For hematopoietic CFU formation, 129±9 and 86±22 CFUs/10$^4$ BCs were formed from BCs derived from BGMs supplemented with and without bFGF (20 ng/ml), respectively. Furthermore, no difference was observed for the development of different CFUs (CFU-mix, CFU-G, CFU-M and CFU-E) between the two groups (data not shown). For endothelial lineage differentiation, more BCs (62±3%) from BGM with bFGF (20 ng/ml) differentiated into endothelial cells than BCs (55±3%) derived from BGM without bFGF supplement. Endothelial cells from both sources formed capillary-vascular like structures efficiently after plating on Matrigel (FIGS. 2B and 2C). These results suggest that bFGF promotes the growth of BCs, but does not cause preferential lineage differentiation.

Example 4

Robust Generation of Hemangioblasts from hESCs Maintained without Feeder Cells

Figure 4:
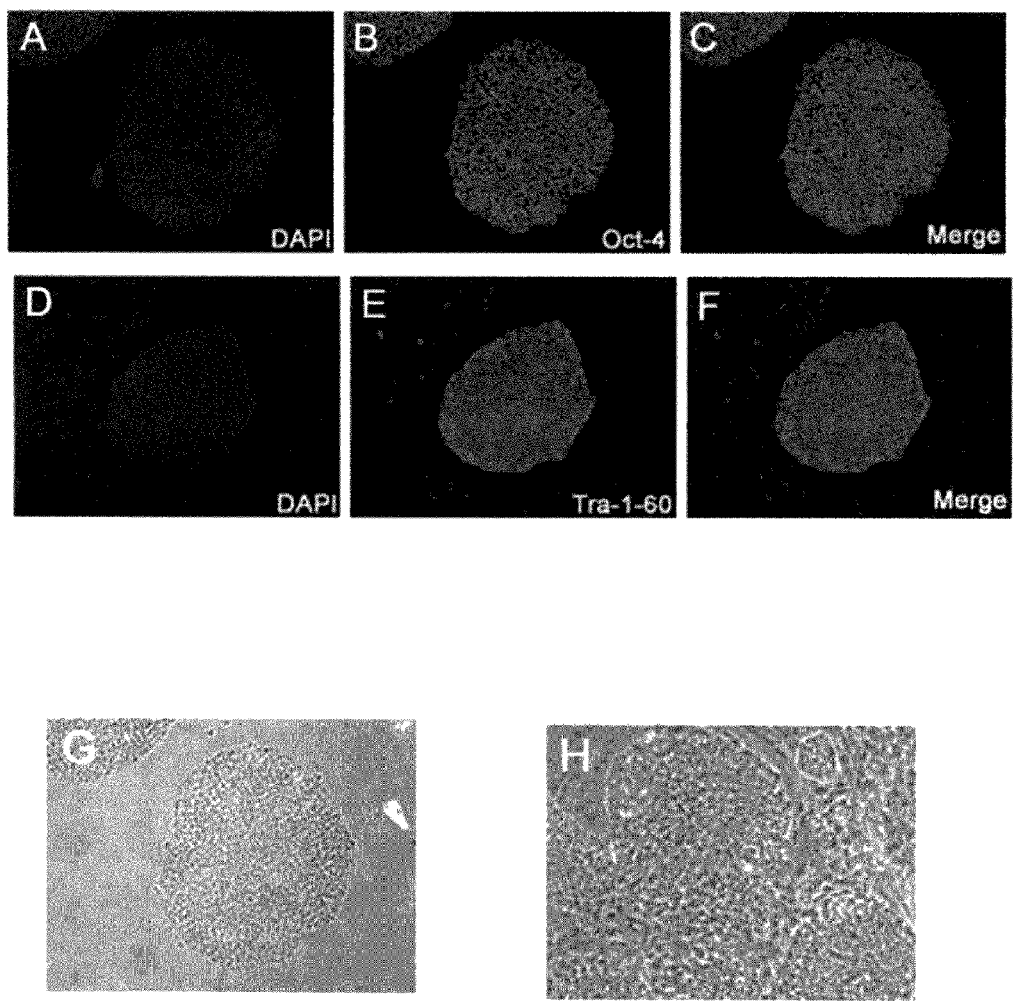
FIG. 4 depicts hESC grown under feeder-free conditions retain pluripotency markers and are capable of robust hemangioblast differentiation in accordance with an embodiment of the present invention. After 4-5 passages under feeder-free conditions WA01 cells were stained for expression of the hESC markers Oct-4 (A-C: DAPI, Oct-4 and merged respectively) and Tra-1-60 (D-F DAPI, TRA-1-60, and merged respectively) Panels G and H demonstrate differences in colony morphology when hESCs are cultured on Matrigel (G) verses MEFs (H). Magnification: originally ×100. In panel I, hESCs were grown either on MEFs or Matrigel and then differentiated under the optimized conditions described herein. Considerably more hemangioblast expansion was observed in Matrigel cultured cells as compared to MEF cultured hESCs. *$P<0.03$, n=3.
Figure 4I:
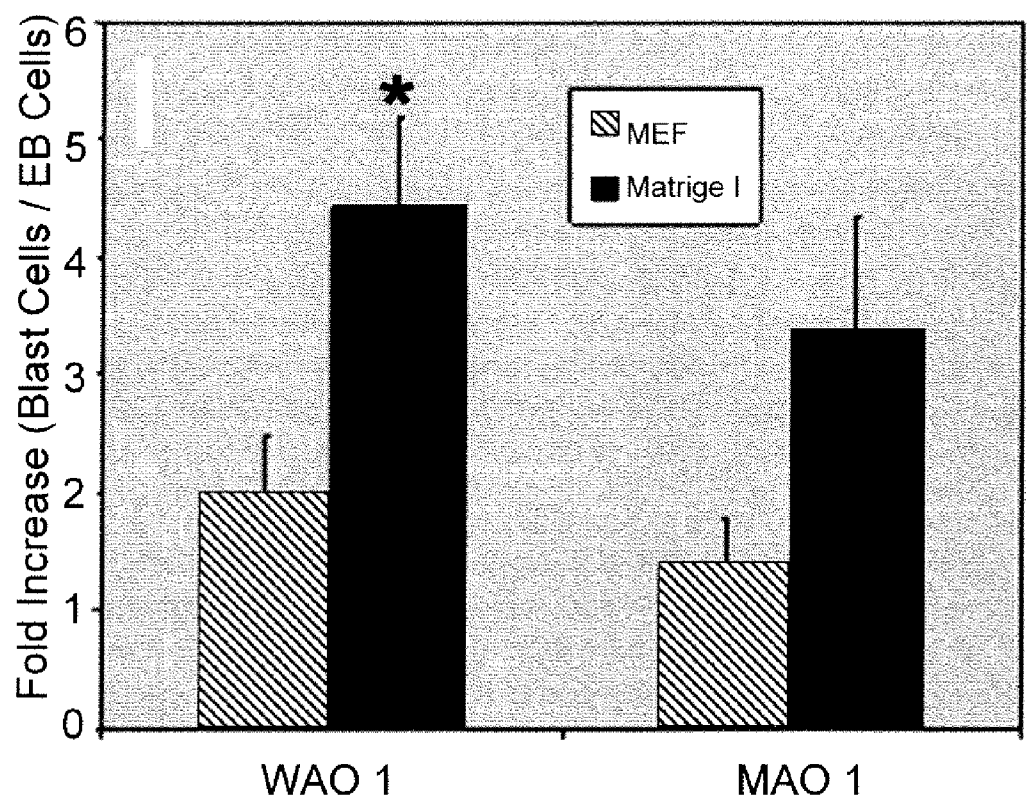

It has been reported that hESCs maintained on MEF feeders contain the nonhuman sialic acid N-glycolylneuraminic acid (Neu5Gc)[15,7,8], and that animal sources of Neu5Gc can cause a potential immunogenic reaction with human complement. The culturing of hESCs on MEF feeder layers prevents complete elimination of animal Neu5Gc, and raises concerns for the potential clinical applications of hemangioblasts generated from hESC lines maintained under these conditions. Therefore, we have taken steps to determine whether hemangioblasts can be generated from hESCs maintained without MEF feeders. Three hESC lines were passaged with dispase onto plates coated with hESC-qualified Matrigel matrix, and maintained in mTeSR medium as described in Materials and Methods. Their undifferentiated state was confirmed with immunofluorescence staining for the expression of Oct-4 and Tra-1-60 antigens and colony morphology (FIG. 4A-4H), These cells were collected and utilized for the development of BCs using the optimized conditions described above. Interestingly, a significantly higher number of BCs were observed with feeder-free hESCs as compared to hESCs cultured on MEF feeders when identical numbers of EB cells were plated (FIG. 4I, p<0.05). These results were observed for all three tested hESC lines WA01, MA01 and HUES-3 (data not shown).

Example 5

Mechanism Underlying the Effects of BMP-4 and VEGF on Hemangioblast Development

Figure 5:
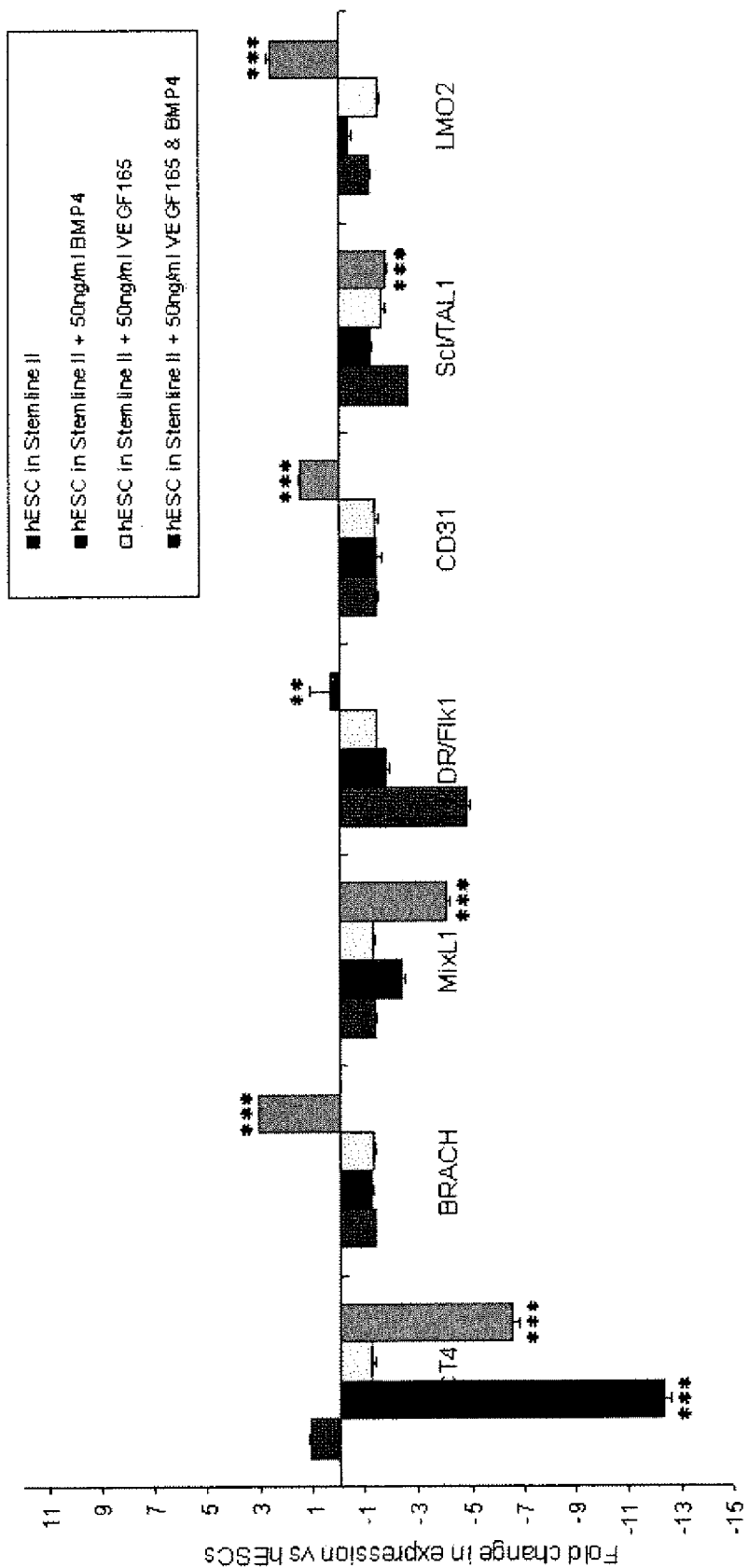
FIG. 5 depicts qRT-PCR analysis of gene expression in EBs cultured under different conditions in accordance with an embodiment of the present invention. Expression levels of various genes associated with development of hemangioblasts were analyzed in EBs derived in the presence or absence of either or a combination of both BMP-4 and VEGF$_{165}$. β-Actin was used as an internal control to normalize gene expression. Relative gene expression is presented as a fold difference compared to average expression levels observed in undifferentiated hESCs. $P<0.002$; *$P<0.0004$, n=3.

In order to dissect the molecular mechanism underlying the effects of BMP-4 and VEGF on hemangioblast development from hESCs, the inventors compared the expression of genes associated with the development of hemangioblasts in 3.5 day-old EBs that were formed in Stemline II medium both with and without each factor, as well as with a combination of BMP-4 and VEGF. Gene expression was analyzed by real-time RT-PCR (qRT-PCR) and compared with their levels in undifferentiated hESCs. EBs formed without any factor expressed higher levels of OCT-4, a marker for hESCs, than undifferentiated hESCs. Supplementation of VEGF in EB medium led to a moderate down regulation of OCT-4 expression; whereas the addition of BMP-4 or BMP-4 plus VEGF resulted in a significant decrease in OCT-4 expression (p<0.0005, FIG. 5). There was no additive effect of BMP-4 and VEGF on OCT-4 expression. The expression of T-brachyury gene, the earliest marker expressed in mesoderm cells, was downregulated in all samples except EBs derived from cultures containing both BMP-4 and VEGF (the latter showing a significant increase in its expression (p<0.0005). Similar expression patterns were observed for CD31 and LMO2; significantly increased levels of expression were only detected in EBs exposed to a combination of BMP-4 and VEGF (p<0.0005). KDR, one of the most studied VEGF receptor, has been shown to be expressed in all hESC lines[4,5]; its expression was dramatically down regulated in EBs derived from media with no addition of exogenous factor, and with supplement of BMP-4 or VEGF alone. However, a moderate but significant increase in KDR expression was observed in EBs formed in the presence of BMP-4 and VEGF (p<0.002), a condition that promoted efficient development of hemangioblasts from hESCs. Surprisingly, in contrast to a recent report[14], substantial decreases in the expression of MixL and SCL/TAL-1 genes were detected in EBs formed in all conditions. One possible explanation is that growth in different serum-free media caused a different expression pattern in these genes. Nevertheless, these results suggest that the commitment and development of mesoderm/hemangioblast from hESCs requires both BMP-4 and VEGF, consistent with the results of blast colony development (FIG. 1).

Example 6

Identification of Surface Markers for Progenitors of Blast Cells

Figure 6:
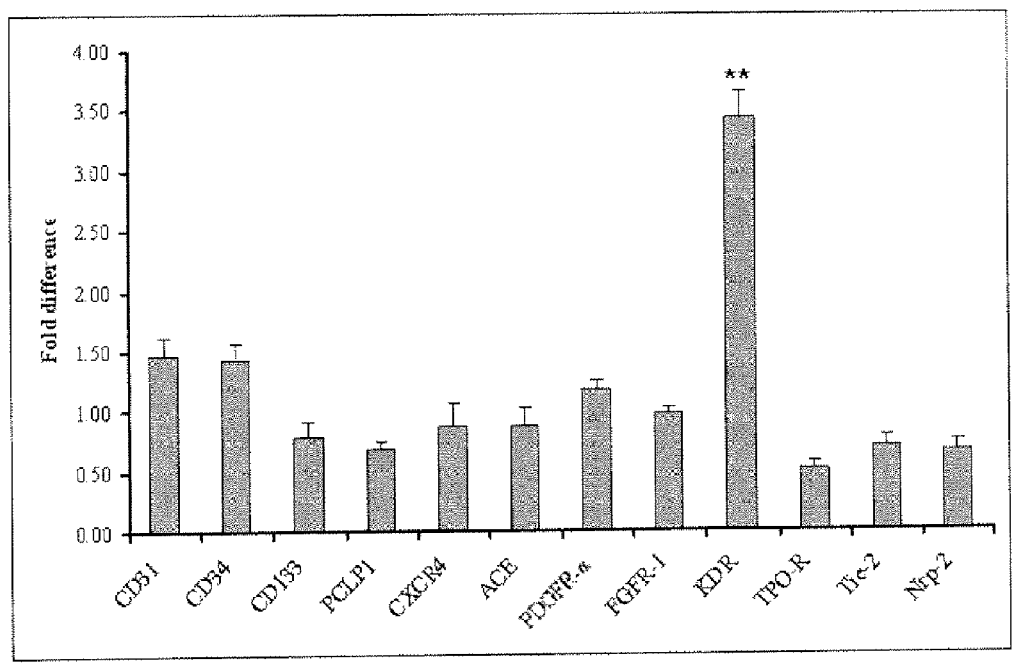
FIG. 6 depicts identification of surface markers for hemangioblast progenitors in accordance with an embodiment of the present invention. EB cells were enriched with different antibodies using EasySep Kit, then plated for the development of blast colonies. **$P<0.01$, n=3.

In our original method[2], BCs were generated by replating day 3.5 EBs cells in 1% methylcellulose supplemented with defined factors. This strategy is important when identifying BCs that possess the potential to form hematopoietic and endothelial cells, and it is also reproducible when generating BCs from hESCs. However, this approach utilizes dishes in standard tissue culture incubators, and thus cannot be adapted to rotary bioreactors for scale-up. This limitation is mainly due to the fact that cells from day 3.5 EBs are heterogeneous and include undifferentiated hESCs (only a portion of the cells are BC progenitors), Replating this heterogeneous population in liquid culture would therefore lead to the growth of all cells including the formation of secondary EBs from undifferentiated hESCs, excluding their possible use in clinical applications. However, if a marker(s) for the progenitor of BCs can be identified, the purified progenitor can be seeded in liquid culture adapted with a rotary bioreactor for scaled-up production of BCs. We therefore selected 12 cell surface molecules that are associated with the development of mesoderm derivatives. The corresponding antibodies were used to enrich cells from day 3.5 EBs, and the enriched cells assayed for blast colony forming ability. As shown in FIG. 6, KDR+ cells from 3.5 day EBs generated three times more blast colonies than the unfractioned control cells (p<0.01), which is consistent with previous studies[5]. Although we also found a moderate increase in blast colonies (≈1.5 fold) after plating CD31+ and CD34+ enriched populations, the increase did not reach statistical significance. All other enriched populations produced equal or less blast colonies as compared with unfractioned control cells, indicating that the BC progenitor does not express these molecules. The unbound (flow through) cells of all antibodies tested also formed similar numbers of blast colonies as the unfractioned cells, suggesting that even KDR+, CD34+ and CD31+ cells represent a very limited portion of the cells that are capable of forming blast colonies.

and four lines (MA01, MA03, MA40, and MA09) derived at Advanced Cell Technology. Undifferentiated human ES cells were cultured on inactivated (mitomycin C-treated) mouse embryonic fibroblast (MEF) cells in complete hES media until they reach 80% confluence (Klimanskaya & McMahon; Approaches of derivation and maintenance of human ES cells: Detailed procedures and alternatives, in Handbook of Stem Cells. Volume 1: Embryonic Stem Cells, ed. Lanza, R. et al., (Elsevier/Academic Press, San Diego, 2004). Then the undifferentiated hES cells were dissociated by 0.05% trypsin-0.53 mM EDTA (Invitrogen) for 2-5 min and collected by centrifugation at 1,000 rpm for 5 minutes.

ES Formation.

To induce hemangioblast precursor (mesoderm) formation, hES cells (2 to $5 \times 10^5$ cells/ml) were plated on ultra-low attachment dishes (Corning) in serum-free Stemline media (for e.g., Stemline I or II, Sigma™) with the addition of BMP-4 and VEGF$_{165}$ (50 ng/ml, R&D Systems) and cultured in 5% CO2. Approximately 48 hours later, the EB medium was replenished and supplemented with a cocktail of early hematopoietic/endothelial growth factors. For example, half the media were removed and fresh media were added with the same final concentrations of BMP-4 and VEGF, plus SCF, TPO and FLT3 ligand (20 ng/ml, R&D Systems). The triple protein transduction domain (tPTD)-HoxB4 fusion protein (1.5 µg/ml) was added to the culture media between 48-72 hr to expand hemangioblast and its precursor.

Hemangioblast Expansion.

After 3.5-5 days, EBs were collected and dissociated by 0.05% trypsin-0.53 mM EDTA (Invitrogen) for 2-5 min, and a single cell suspension was prepared by passing through 22G needle 3-5 times. Cells were collected by centrifugation at 1,000 rpm for 5 minutes and counted. Cell pellets were resuspended in 50-200 µl of serum-free Stemline media. To expand

TABLE 1

Sequences of gene-specific primers used in qRT-PCR

| Gene | Forward Primer, 5'-3' | SEQ ID NO | Reverse Primer, 5'-3' | SEQ ID NO | Ref |
|---|---|---|---|---|---|
| OCT-4 | GAAGGTATTCAGCCAAACGC | 16 | GTTACAGAACCACACTCGGA | 17 | NA |
| BRACH | TGCTTCCCTGAGACCCAGTT | 18 | GATCACTTCTTTCCTTTGCATCAAG | 19 | (33) |
| MixL1 | CCGAGTCCAGGATCCAGGTA | 20 | CTCTGACGCCGAGACTTGG | 21 | (33) |
| KDR/Flk1 | CCAGCCAAGCTGTCTCAGT | 22 | CTGCATGTCAGGTTGCAAAG | 23 | (4) |
| CD31 | GAGTCCTGCTGACCCTTCTG | 24 | ATTTTGCACCGTCCAGTCC | 25 | (4) |
| Scl/TAL1 | ATGAGATGGAGATTACTGATG | 26 | GCCCCGTTCACATTCTGCT | 27 | (4) |
| LMO2 | AACTGGGCCGGAAGCTCT | 28 | CTTGAAACATTCCAGGTGATACA | 29 | (4) |
| GAPDH | CGATGCTGGCGCTGAGTAC | 30 | CCACCACTGACACGTTGGC | 31 | NA |
| β-Actin | GCGGGAAATCGTGCGTGACA | 32 | GATGGAGTTGAAGGTAGTTTCG | 33 | NA |

Example 7

Generation of Human Hemangio-Colony Forming Cells from Human ES Cells

Human ES Cell Culture.

The hES cell lines used in this study were previously described HI and H9 (NIH-registered as WA01 and WA09)

hemangioblasts, single cell suspensions from EBs derived from differentiation of 2 to $5 \times 10^5$ hES cells were mixed with 2 ml BL-CFC/hemangioblast expansion media (BGM) containing 1.0% methylcellulose in Iscove's MDM, 1-2% Bovine serum albumin, 0.1 mM 2-mercaptoethanol and a cocktail of growth factors. For example, 10 µg/ml rh-Insulin, 200 µg/ml iron saturated human transferrin, 20 ng/ml rh-GM-CSF, 20 ng/ml rh-IL-3, 20 ng/ml rh-IL-6, 20 ng/ml rh-G-CSF, 3 to 6 units/ml rh-EPO, 50 ng/ml rh-SCF, 50 ng/ml rh-FLt3 ligand, 50 ng/ml rh-VEGF and 50 ng/ml rh-BMP-4) ("rh" stands for "recombinant human") and 1.5 µg/ml of tPTD-HoxB4 fusion protein, with/without 50 ng/ml of TPO and FL was added. The cell mixtures were plated on ultra-low attachment dishes and incubated at 37° C. in 5% $CO_2$ for 4-7 days. After 4-6 days, grape-like hemangioblast blast colonies (referred to as BL-CFCs or BCs) were visible by microscopy. Cytospin preparation and Wright-Giemsa staining of the hES-derived blast colonies confirmed morphologic features of immature blast cells. To extend these results to other hES cell lines (WA09 [H9], MA01, MA03, MA40 and MA09, supplements of FL and Tpo were necessary for sustained growth of the BC colonies (without FL and Tpo, small (10-20 cell hES-BCs were obtained which died after 4-8 days). Epo was also essential for BC formation and growth in all hES cell lines tested. These cells could be readily expanded (one 6-well plate of hES generated approximately 6.1±0.66 [mean±SD] million hemangioblasts) under the well-defined and reproducible conditions described above.

For BL-CFC immunocytochemical analysis, purified BL-CFCs were cytospun onto polylysine treated glass slides and fixed in 4% paraformaldehyde. For examining the expression of most genes, primary antibodies were incubated at 4° C. overnight, followed by fluorescent dye labeled secondary antibodies, and finally examined under fluorescent microscope. Normal human BM cells, K562 cells and HUVEC were used as controls.

Immunocytochemical analysis revealed that the hES cell-derived BL-CFCs or BCs expressed GATA-1 and GATA-2 proteins, LMO2 proteins, CXCR-4, TPO and EPO receptors, and readily reacted with antibody specific for CD71, the transferrin receptor (Table 1 and FIG. 16d-v). The cells expressed little or no CD31, CD34 and KDR, or other adhesion molecules. As described more fully in Ser. No. 11/787,262, the cells are hemangio-colony forming cells.

Example 8

Expansion of a Distinct Cell Type: Non-Engrafting Hemangio Cell

As detailed above and in Ser. No. 11/787,262, hemangio-colony forming cells were generated following expansion for approximately 4-7 days. Under certain conditions, further culture of EBs beyond 7 days produced large numbers of a distinct cell type. As described throughout, this distinct progenitor cell type is referred to as a non-engrafting hemangio cell.

EBs were cultured as described above. On day 7 of the expansion protocol, following formation of grape-like clusters indicative of hemangio-colony forming cells, 5 ml of BL-medium was added on top of the these cultures of grape-like clusters of cells. The cultures are semi-solid and contain 10 mL of methylcellulose medium. Following addition of fresh medium, the cells are cultured an additional 3-6 days, for a total of 10-13 days in culture post-EB formation.

The addition of fresh medium greatly enhanced continued cell proliferation and survival during these prolonged culture periods. After 10-13 days in culture, cells were purified from the cluster. Similar to hemangio-colony forming cells, these non-engrafting hemangio cells formed grape-like clusters and were loosely adherent to each other. However, as detailed below, these cells were not identical to the previously identified hemangio-colony forming cells.

When the cells were separated from the clusters on day 10, and the yield of cells compared to the yield of hemangio-colony forming cells generally observed when collected on day 7, we observed a dramatic increase in the number of cells obtained. Specifically, greater than 5 fold more cells were purified on day 10 versus day 7. As such, larger quantities of non-engrafting hemangio cells can be readily produced and used, for example, to produce larger quantities of differentiated cell types.

The cells identified after 10-13 days of expansion culture are similar, in many respects, to the previously identified hemangio-colony forming cells. For example, the cells are typically loosely adherent to each other (like hemangio-colony forming cells). Additionally, cells identified after 10-13 days of expansion culture differentiated in vitro to produce hematopoietic cell types. Specifically, non-engrafting hemangio cells retain the capacity to form hematopoietic CFUs. Cells were separated from the grape-like clusters after 10-13 days in culture and plated in semi-solid methylcellulose medium containing cytokines that support growth of hematopoietic CFUs. After 10-12 days in culture, erythrocyte CFUs, granulocyte CFUs, macrophage CFUs, and mixed hematopoietic CFUs were observed, thus demonstrating the potential to produce hematopoietic cell types.

Despite the similarities between hemangio-colony forming cells and the non-engrafting hemangio cells described herein, these cells do not have the same differentiation potential. Without wishing to be bound by any particular theory, the non-engrafting hemangio cells may represent a developmentally distinct cell type that, in contrast to hemangio-colony forming cells, are no longer capable of engrafting into the bone marrow upon in vivo delivery to an immunodeficient animal. Specifically, 1-5 million human non-engrafting hemangio cells (e.g., cells cultured for 10-13 days post-EB formation) were administered to NOD/SCID mice. Examination of 24 mice failed to reveal engraftment of human cells into the bone marrow or spleen. In contrast, when similar numbers of human hemangio-colony forming cells (e.g., cells cultured for 6-8 days) were administered to NOD/SCID mice, human cells engrafted in the bone marrow of all 12 animals examined.

Other illustrative methods, compositions, preparations, and features of the invention are described in the following documents: U.S. application Ser. No. 11/787,262, filed Apr. 13, 2007, and entitled "Hemangio-Colony Forming Cells." The teachings of this application are hereby incorporated by reference in their entirety.

It should be noted that Applicants consider all operable combinations of the disclosed illustrative embodiments to be patentable subject matter including combinations of the subject matter disclosed in U.S. application Ser. No. 11/787,262. For example, the non-engrafting hemangio cells provided herein (i) may have one or more of the properties of the cells described in U.S. application Ser. No. 11/787,262, (ii) may be formulated as compositions, preparations, cryopreserved preparations, or purified or mixed solutions as described in U.S. application Ser. No. 11/787,262, (iii) may be used therapeutically and in blood banking as described in U.S. application Ser. No. 11/787,262, and (iv) may be used to generate partially and terminally differentiated cell types for in vitro or in vivo use as described in U.S. application Ser. No. 11/787, 262. Furthermore, the non-engrafting hemangio cells can be derived from ES cells, ED cells, pluripotent stem cells (including iPS cells) etc. using any of the methodologies described herein and in U.S. application Ser. No. 11/787,262.

Example 9

Efficient Generation of Hemangioblasts from Human iPSCs

Generation of High Quality iPSCs

In several of the inventors' preliminary studies, they are able to generate hemangioblast colonies from human IMR90 (FIG. 12c) and Adult4-3 iPSCs (data not shown), using the optimized hESC differentiation conditions. Although their efficiency was much lower compared to hESCs, they clearly demonstrate the hemangioblast differentiation potential of human iPSCs. The observed low efficiency may be due to multiple factors, one of them being the quality of the iPSCs. The inventors observed this to be one of the most important factors for high-efficient generation of hemangioblasts. High quality hESC cultures are composed of colonies with tight borders with minimal signs of differentiation as seen under microscope, at about 80% confluence, but not touching each other. They grow at a moderate rate: 1:3 split passaged hESCs will reach confluence in 3-5 days with positive staining of pluripotency markers in almost every cell. High quality hESCs usually generate a high number of EB cells (e.g. $2 \times 10^6$ high quality hESCs will generate $\approx 2-3 \times 10^6$ EB cells after 3.5 days). The critical steps for obtaining high quality iPSCs include: (1) passaging with trypsin vs. collagenase: The inventors have demonstrated that hESCs can be routinely passaged by trypsin/EDTA after the initial adaptation from mechanically passaged cultures has been performed (Klimanskaya et al. Approaches of derivation and maintenance of human ES cells: Detailed procedures and alternatives. In: Lanza Rea, ed. Handbook of Stem Cells. Volume 1: Embryonic Stem Cells. New York, USA: Elsevier/Academic Press, 2004:437-449.). In the inventors' experience, trypsin works better than widely used collagenase IV because it produces smaller cell clumps (2-5 cells) and single cells that form more uniformly distributed and similarly sized colonies, which will eliminate premature contact between colonies and limit spontaneous differentiation, whereas collagenase passaging results in larger colonies that show more extensive differentiation and have to be passed either at a lower splitting ratio or before the desired density of the culture is reached. Overall, trypsin/EDTA passaging allows the ability to scale up the culture 3-4 times faster than collagenase and to get a homogenous cell population. These observations may also be valid for human iPSCs. The inventors experiments showed that human iPSCs can be adapted to trypsin digestion, and these cells maintain undifferentiated status after more than 20 passages; (2) Maintaining with mouse embryonic fibroblasts (MEF feeder) or feeder-free: long term maintenance of hESCs and iPSCs required MEF feeders. The culturing of hESCs and iPSCs on MEF feeder layers prevents complete elimination of animal components, and raises concerns for the potential clinical applications of derivatives generated from hESCs and iPSCs maintained under these conditions. Therefore, the first step has been taken to determine whether hemangioblasts can be generated from hESCs maintained on Matrigel matrix in mTeSR medium. The inventors have demonstrated that a significantly higher number (3-fold increase) of hemangioblasts were generated with feeder-free hESCs as compared to hESCs cultured on MEF feeders when identical numbers of EB cells were plated ($p<0.05$) for all three tested hESC lines WA01, MA01 and HuES-3 (Lu et al. Regen Med 2008:3:693-704.). The inventors then initiated the experiments of culturing human iPSCs in the above feeder-free system, and human iPSCs maintained in feeder-free condition expressed the pluripotency markers of Nanog, Oct-4, SSEA-4, and Tra-1-60 (FIG. 11). Whether human iPSCs from feeder-free condition will differentiate to hemangioblasts with high efficiency will be tested.

Optimization of Embryoid Body (EB) Formation and Differentiation: Human iPSCs show poor survival ability after cell dissociation and during EB formation, a phenomenon also observed for hESCs. It has been shown that addition of a selective Rho-associated kinase (ROCK) inhibitor. Y-27632, to serum-free EB formation medium prevents hESCs from apoptosis, enhances EB formation, and promotes differentiation (Watanabe et al. Nat Biotechnol 2007; 25:681-686). The experiments showed that supplement of Y-27632 in the serum-free EB formation and differentiation medium resulted in better formation of EBs from human iPS(IMR90)-1 cells than control medium: EBs in StemLine II medium plus cytokines only are usually smaller with many dead cells after 24 hrs; whereas EBs in medium added with Y-27632 are smooth and large with many fewer dead cells surrounding them (FIGS. 12a and 12b), indicating healthier EBs were formed. After plating for blast colony formation, cells from EBs treated with Y-27632 developed substantial more and healthier blast colonies than that derived from EBs without Y-27632 treatment (FIGS. 12c and 12d), generating >2 fold more hemangioblasts. Previous studies also suggest that insulin, a component in almost all cell culture media including StemLine II medium used in the EB formation system described herein, is a potent inhibitor of hESC mesoderm differentiation, possibly through PI3K/Akt signaling pathway. Inhibition of PI3K/Akt signaling pathway enhanced mesoderm differentiation of hESCs in serum-free conditions (Freund et al. Stem Cells signaling pathway inhibitor in EB formation and differentiation medium substantially increased the formation of hemangioblasts from MA09 hESCs. A >2.5 fold increase of hemangioblasts was obtained from dishes treated with PI3K/Akt inhibitor as compared with dishes from controls. Similarly, supplementation with the PI3K/Akt signaling pathway inhibitor alone or plus Y-27632 during EB formation also resulted in more and healthier blast colonies from iPS(IMR90)-1 cells than controls (FIG. 12e), producing 2.1-fold and 2.6 fold more hemangioblasts for PI3K/Art inhibitor treated EBs and PI3K/Art inhibitor plus ROCK inhibitor treated EBs, respectively. The hemangioblasts were then purified and plated under conditions for hematopoietic or endothelial cell differentiation. As shown in FIG. 12f-12j, these cells differentiated into both hematopoietic and endothelial cells after replating under appropriate conditions.

REFERENCES

1. Wagner R C: Endothelial cell embryology and growth. *Adv. Microcirc.* 9, 45-75 (1980).
2. Lu S J, Feng Q, Caballero S et al: Generation of functional hemangioblasts from human embryonic stem cells. *Nat. Methods* 4(6), 501-509 (2007).
3. Wang L, Li L, Shojaei F et al: Endothelial and hematopoietic cell fate of human embryonic stem cells originates from primitive endothelium with hemangioblastic properties. *Immunity.* 21(1), 31-41 (2004).
4. Zambidis E T, Peault B, Park T S, Bunz F, Civin C I: Hematopoietic differentiation of human embryonic stem cells progresses through sequential hematoendothelial, primitive, and definitive stages resembling human yolk sac development. *Blood* 106(3), 860-870 (2005).
5. Kennedy M, D'Souza S L, Lynch-Kattman M, Schwantz S, Keller G: Development of the hemangioblast defines the onset of hematopoiesis in human ES cell differentiation cultures. *Blood* 109(7), 2679-2687 (2007).
6. Klimanskaya I, McMahon J. Approaches of derivation and maintenance of human ES cells: Detailed procedures and alternatives. In: *Handbook of Stem Cells. Volume 1: Embryonic Stem Cells.* Lanza Rea (Eds.). Elsevier/Academic Press, 2004)
7. Ludwig T E, Bergendahl V, Levenstein M E, Yu J, Probasco M D, Thomson J A: Feeder-independent culture of human embryonic stem cells. *Nat. Methods* 3(8), 637-646 (2006).
8. Ludwig T E, Levenstein M E, Jones J M et al: Derivation of human embryonic stem cells in defined conditions. *Nat. Biotechnol.* 24(2), 185-187 (2006).
9. Livak K J, Schmittgen T D: Analysis of relative gene expression data using real-time quantitative PCR and the 2(−Delta Delta C(T)) Method. *Methods* 25(4), 402-408 (2001).
10. Lu S J, Feng Q, Ivanova Y et al: Recombinant HoxB4 Fusion Proteins Enhance Hematopoietic Differentiation of Human Embryonic Stem Cells. *Stem Cells Dev.* 16(4), 547-560 (2007).
11. Soker S, Takashima S, Miao H Q, Neufeld G, Klagsbrun M: Neuropilin-1 is expressed by endothelial and tumor cells as an isoform-specific receptor for vascular endothelial growth factor. *Cell* 92(6), 735-745 (1998).
12. Faloon P, Arentson E, Kazarov A et al: Basic fibroblast growth factor positively regulates hematopoietic development. *Development* 127(9), 1931-1941 (2000).
13. Pearson S, Sroczynska P, Lacaud G, Kouskoff V: The stepwise specification of embryonic stem cells to hematopoietic fate is driven by sequential exposure to Bmp4, activin A, bFGF and VEGF. *Development* 135(8), 1525-1535 (2008),
14. Pick M, Azzola L, Mossman A, Stanley E G, Elefanty A G: Differentiation of human embryonic stem cells in serum-free medium reveals distinct roles for bone morphogenetic protein 4, vascular endothelial growth factor, stem cell factor, and fibroblast growth factor 2 in hematopoiesis. *Stem Cells* 25(9), 2206-2214 (2007).
15. Martin M J, Muotri A, Gage F, Varki A: Human embryonic stem cells express an immunogenic nonhuman sialic acid. *Nat. Med.* 11(2), 228-232 (2005).
16. Huber T L, Zhou Y, Mead P E, Zon L I: Cooperative effects of growth factors involved in the induction of hematopoietic mesoderm. *Blood* 92(11), 4128-4137 (1998).
17. Winnier G, Blessing M, Labosky P A, Hogan B L: Bone morphogenetic protein-4 is required for mesoderm formation and patterning in the mouse. *Genes Dev.* 9(17), 2105-2116 (1995).
18. Johansson B M, Wiles M V: Evidence for involvement of activin A and bone morphogenetic protein 4 in mammalian mesoderm and hematopoietic development. *Mol. Cell Biol.* 15(1), 141-151 (1995).
19. Wiles M V, Johansson B M: Embryonic stem cell development in a chemically defined medium. *Exp. Cell Res.* 247(1), 241-248 (1999).
20. Nakayama N, Lee J, Chiu L: Vascular endothelial growth factor synergistically enhances bone morphogenetic protein-4-dependent lymphohematopoietic cell generation from embryonic stem cells in vitro. *Blood* 95(7), 2275-2283 (2000).
21. Li F, Lu S-J, Vida L, Thomson J A, Honig G R: Bone morphogenetic protein-4 induces efficient hematopoietic differentiation of rhesus monkey embryonic stem cells in vitro. *Blood* 98(2), 335-342 (2001).
22. Tian X, Morris J K, Linehan J L, Kaufman D S: Cytokine requirements differ for stroma and embryoid body-mediated hematopoiesis from human embryonic stem cells. *Exp. Hematol.* 32(10), 1000-1009 (2004).
23. Chadwick K, Wang L, Li L et al: Cytokines and BMP-4 promote hematopoietic differentiation of human embryonic stem cells. *Blood* 2003 102(3), 906-915 (2003).
24. Cerdan C, Rouleau A, Bhatia M: VEGF-A165 augments erythropoietic development from human embryonic stem cells. *Blood* 103(7), 2504-2512 (2004).
25. Park C, Afrikanova I, Chung Y S et al: A hierarchical order of factors in the generation of FLK- and SCL-expressing hematopoietic and endothelial progenitors from embryonic stem cells. *Development* 131(11), 2749-2762 (2004).
26. Xu C, Rosier E, Jiang J et al: Basic fibroblast growth factor supports undifferentiated human embryonic stem cell growth without conditioned medium. *Stem Cells* 23(3), 315-323 (2005).
27. Xu R H, Peck R M, Li D S, Feng X, Ludwig T, Thomson J A: Basic FGF and suppression of BMP signaling sustain undifferentiated proliferation of human ES cells. *Nat. Methods* 2(3), 185-190 (2005).
28. Levenstein M E, Ludwig T E, Xu R H et al: Basic fibroblast growth factor support of human embryonic stem cell self-renewal. *Stem Cells* 24(3), 568-574 (2006).
29. Yeoh J S, van O R, Weersing E et al: Fibroblast growth factor-1 and -2 preserve long-term repopulating ability of hematopoietic stem cells in serum-free cultures. *Stem Cells* 24(6), 1564-1572 (2006).
30. Dell'Era P, Ronca R, Coco L, Nicoll S, Metra M, Presta M: Fibroblast growth factor receptor-1 is essential for in vitro cardiomyocyte development. *Circ. Res.* 93(5), 414-420 (2003).
31. de H G, Weersing E, Dontje B et al: In vitro generation of long-term repopulating hematopoietic stem cells by fibroblast growth factor-1. *Dev. Cell* 4(2), 241-251 (2003).
32. Ginis I, Luo Y, Miura T et al: Differences between human and mouse embryonic stem cells. *Dev. Biol.* 269(2), 360-380 (2004).
33. D'Amour K A, Agulnick A D, Eliazer S, Kelly O G, Kroon E, Baetge E E: Efficient differentiation of human embryonic stem cells to definitive endoderm. *Nat. Biotechnol.* 23(12), 1534-1541 (2005).

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method for expanding hemangioblasts comprising growing mammalian hemangioblasts in serum-free media comprising BMP4 protein and VEGF protein or functional equivalents or active fragments thereof in an amount sufficient to support the proliferation of said hemangioblasts.

2. The method according to claim 1, wherein said hemangioblasts are enriched, purified, or isolated from cord blood, peripheral blood, or bone marrow.

3. The method according to claim 1, wherein said hemangioblasts are human hemangioblasts.

4. The method according to claim 1, wherein said hemangioblasts are grown in vitro to achieve at least $1 \times 10^6$ hemangioblasts.

5. The method according to claim 1, wherein said serum-free media further comprises a homeobox protein, a functional equivalent or an active fragment thereof.

6. The method according to claim 5, wherein the homeobox protein, functional equivalent or active fragment thereof is a HOXB4 protein or a functional equivalent or an active fragment thereof.

7. The method according to claim 6, wherein said HOXB4 is mouse or human HOXB4.

8. The method according to claim 7, wherein said HOXB4 is human HOXB4.

9. The method according to claim 6, wherein said HOXB4 comprises a full-length protein.

10. The method according to claim 6, wherein said HOXB4 comprises the amino acid sequence of SEQ ID NO: 1 or SEQ ID NO: 3.

11. The method according to claim 1, wherein said serum-free media further comprises a fusion protein comprising HOXB4 and a protein transduction domain (PTD).

12. The method according to claim 11, wherein said protein transduction domain (PTD) is TAT protein, a functional variant or an active fragment thereof.

13. The method according to claim 12, wherein said TAT protein comprises the amino acid sequence of SEQ ID NO: 14.

14. The method according to claim 11, wherein said PTD comprises one or more copies of a TAT polypeptide with the amino acid sequence of SEQ ID NO: 14.

* * * * *